US011993773B2

(12) United States Patent
Godron et al.

(10) Patent No.: US 11,993,773 B2
(45) Date of Patent: May 28, 2024

(54) METHODS FOR EXTENDING POLYNUCLEOTIDES

(71) Applicant: DNA Script SAS, Le Kremlin-Bicêtre (FR)

(72) Inventors: Xavier Godron, Paris (FR); Adrian Horgan, Paris (FR); Sylvain Gariel, Paris (FR); Jeffrey Jeddeloh, Verona, WI (US); Robert Nicol, Cambridge, MA (US); Thomas Ybert, Paris (FR)

(73) Assignee: DNA Script SAS, Le Kremlin-Bicêtre (FR)

( * ) Notice: Subject to any disclaimer, the term of this patent is extended or adjusted under 35 U.S.C. 154(b) by 349 days.

(21) Appl. No.: 17/192,578

(22) Filed: Mar. 4, 2021

(65) Prior Publication Data

US 2021/0198661 A1  Jul. 1, 2021

Related U.S. Application Data

(62) Division of application No. 16/970,590, filed as application No. PCT/EP2019/084347 on Dec. 10, 2019, now Pat. No. 11,268,091.

(30) Foreign Application Priority Data

Dec. 13, 2018  (EP) ..................................... 18306687
Feb. 25, 2019  (EP) ..................................... 19305219

(51) Int. Cl.
*C12N 15/10* (2006.01)
*C12N 15/11* (2006.01)
(Continued)

(52) U.S. Cl.
CPC ........ *C12N 15/1096* (2013.01); *C12N 15/111* (2013.01); *C12Q 1/44* (2013.01); *C40B 50/06* (2013.01); *C40B 50/08* (2013.01); *C40B 50/14* (2013.01); *C40B 70/00* (2013.01); *C12N 2310/319* (2013.01); *C12N 2310/3515* (2013.01); *C12N 2330/31* (2013.01)

(58) Field of Classification Search
None
See application file for complete search history.

(56) References Cited

U.S. PATENT DOCUMENTS 4,683,195 A   7/1987   Mullis et al.
4,683,202 A   7/1987   Mullis
(Continued)

FOREIGN PATENT DOCUMENTS

EP   0303459   2/1989
EP   0799897   10/1997
(Continued)

OTHER PUBLICATIONS

Macosko et al., "Highly Parallel Genome-wide Expression Profiling of Individual Cells Using Nanoliter Droplets," Cell 2015, 161: 1202-1214. (Year: 2015).*

(Continued)

*Primary Examiner* — Kaijiang Zhang
(74) *Attorney, Agent, or Firm* — Gardella Grace P.A.

(57) ABSTRACT

The invention is directed to methods for synthesizing oligonucleotides directly on biomolecules or cells living or fixed. In some embodiments, template-free enzymatic synthesis is implemented under biological conditions with successive cycles of (i) enzymatic addition of a 3'-O-blocked nucleoside triphosphate and (ii) enzymatic deblocking of the incorporated nucleotide to regenerate a free 3' hydroxyl. The invention has applications in single-cell cDNA library construction and analysis.

7 Claims, 19 Drawing Sheets

Specification includes a Sequence Listing.

(51) Int. Cl.
  *C12Q 1/44* (2006.01)
  *C40B 50/06* (2006.01)
  *C40B 50/08* (2006.01)
  *C40B 50/14* (2006.01)
  *C40B 70/00* (2006.01)

(56) References Cited

U.S. PATENT DOCUMENTS

| | | |
|---|---|---|
| 4,772,691 A | 9/1988 | Herman |
| 4,800,159 A | 1/1989 | Mullis et al. |
| 4,965,188 A | 10/1990 | Mullis et al. |
| 5,047,524 A | 9/1991 | Andrus |
| 5,126,022 A | 6/1992 | Soane et al. |
| 5,210,015 A | 5/1993 | Gelfand et al. |
| 5,262,530 A | 11/1993 | Andrus |
| 5,399,491 A | 3/1995 | Kacian et al. |
| 5,436,143 A | 7/1995 | Hyman |
| 5,498,392 A | 3/1996 | Wilding et al. |
| 5,516,664 A | 5/1996 | Hyman |
| 5,587,128 A | 12/1996 | Wilding et al. |
| 5,602,000 A | 2/1997 | Hyman |
| 5,635,400 A | 6/1997 | Brenner |
| 5,656,745 A | 8/1997 | Bischofberger |
| 5,665,539 A | 9/1997 | Sano et al. |
| 5,744,595 A | 4/1998 | Srivastava |
| 5,763,594 A | 6/1998 | Hiatt |
| 5,798,210 A | 8/1998 | Canard |
| 5,808,045 A | 9/1998 | Hiatt |
| 5,854,033 A | 12/1998 | Lizardi |
| 5,858,195 A | 1/1999 | Ramsey |
| 5,872,244 A | 2/1999 | Hiatt |
| 5,917,031 A | 6/1999 | Miura |
| 5,935,527 A | 8/1999 | Andrus |
| 5,981,179 A | 11/1999 | Lorinez et al. |
| 5,990,300 A | 11/1999 | Hiatt |
| 6,001,229 A | 12/1999 | Ramsey |
| 6,010,607 A | 1/2000 | Ramsey |
| 6,033,546 A | 3/2000 | Ramsey |
| 6,054,034 A | 4/2000 | Soane et al. |
| 6,093,302 A | 7/2000 | Montgomery |
| 6,174,670 B1 | 1/2001 | Wittwer et al. |
| 6,214,987 B1 | 4/2001 | Hiatt |
| 6,232,465 B1 | 5/2001 | Hiatt |
| 6,251,595 B1 | 6/2001 | Gordon et al. |
| 6,280,595 B1 | 8/2001 | Montgomery |
| 6,306,599 B1 | 10/2001 | Perbost |
| 6,323,043 B1 | 11/2001 | Caren et al. |
| 6,399,952 B1 | 6/2002 | Maher et al. |
| 6,444,111 B1 | 9/2002 | Montgomery |
| 6,489,103 B1 | 12/2002 | Griffiths et al. |
| 6,613,525 B2 | 9/2003 | Nelson et al. |
| 6,623,929 B1 | 9/2003 | Densham |
| 6,664,079 B2 | 12/2003 | Ju |
| 6,777,189 B2 | 8/2004 | Wei |
| 6,960,437 B2 | 11/2005 | Enzelberger et al. |
| 7,057,026 B2 | 1/2006 | Barnes |
| 7,078,499 B2 | 7/2006 | Odedra |
| 7,125,671 B2 | 10/2006 | Sood |
| 7,270,951 B1 | 9/2007 | Stemple |
| 7,276,336 B1 | 10/2007 | Webb et al. |
| 7,345,159 B2 | 3/2008 | Ju |
| 7,407,757 B2 | 8/2008 | Brenner |
| 7,494,797 B2 | 2/2009 | Mueller |
| 7,534,561 B2 | 5/2009 | Sana et al. |
| 7,537,897 B2 | 5/2009 | Brenner et al. |
| 7,544,794 B1 | 6/2009 | Brenner |
| 7,566,537 B2 | 7/2009 | Balasubramanian |
| 7,635,578 B2 | 12/2009 | Ju |
| 7,713,698 B2 | 5/2010 | Ju |
| 7,790,869 B2 | 9/2010 | Balasubramanian |
| 7,842,457 B2 | 11/2010 | Berka et al. |
| 7,932,025 B2 | 4/2011 | Carr |
| 7,939,259 B2 | 5/2011 | Kokoris |
| 8,003,312 B2 | 8/2011 | Krutzik |
| 8,012,690 B2 | 9/2011 | Berka et al. |
| 8,034,923 B1 | 10/2011 | Benner |
| 8,048,627 B2 | 11/2011 | Dressman et al. |
| 8,212,020 B2 | 7/2012 | Benner |
| 8,263,335 B2 | 9/2012 | Carr |
| 8,394,586 B2 | 3/2013 | Balasubramanian |
| 8,476,018 B2 | 7/2013 | Brenner |
| 8,507,205 B2 | 8/2013 | Faham |
| 8,674,086 B2 | 8/2014 | Liu |
| 8,808,988 B2 | 8/2014 | Zhao |
| 8,808,989 B1 | 8/2014 | Efcavitch |
| 9,056,289 B2 | 6/2015 | Weitz |
| 9,075,041 B2 | 7/2015 | Kavusi et al. |
| 9,121,062 B2 | 9/2015 | Balasubramanian |
| 9,267,213 B1 | 2/2016 | Maurer et al. |
| 9,339,782 B1 | 5/2016 | Gindilis |
| 9,388,463 B2 | 7/2016 | Balasubramanian |
| 9,410,197 B2 | 8/2016 | Bergmann |
| 9,593,365 B2 | 3/2017 | Frisen et al. |
| 9,874,538 B2 | 1/2018 | Johnson et al. |
| 9,896,709 B2 | 2/2018 | Makarov |
| 9,902,950 B2 | 2/2018 | Church |
| 9,910,008 B2 | 3/2018 | Johnson et al. |
| 10,030,261 B2 | 7/2018 | Frisen et al. |
| 10,246,703 B2 | 4/2019 | Church |
| 10,329,557 B2 | 6/2019 | Johnson |
| 10,392,614 B2 | 8/2019 | Vigneault |
| 10,435,676 B2 | 10/2019 | Champion et al. |
| 10,655,173 B2 | 5/2020 | Zhang |
| 2003/0170698 A1 | 9/2003 | Gascoyne et al. |
| 2005/0037991 A1 | 2/2005 | Bodepudi et al. |
| 2007/0020640 A1 | 1/2007 | McCloskey et al. |
| 2008/0014589 A1 | 1/2008 | Link et al. |
| 2009/0181859 A1 | 7/2009 | Muraguchi et al. |
| 2010/0021984 A1 | 1/2010 | Edd et al. |
| 2010/0173394 A1 | 7/2010 | Colston, Jr. et al. |
| 2010/0255471 A1 | 10/2010 | Clarke et al. |
| 2010/0285975 A1 | 11/2010 | Mathies et al. |
| 2012/0309002 A1 | 12/2012 | Link |
| 2013/0274117 A1 | 10/2013 | Church |
| 2014/0363851 A1 | 12/2014 | Efcavitch |
| 2014/0363852 A1 | 12/2014 | Efcavitch |
| 2015/0247182 A1 | 9/2015 | Faham |
| 2015/0307874 A1 | 10/2015 | Jaitin |
| 2016/0122753 A1 | 5/2016 | Mikkelsen |
| 2016/0138086 A1 | 5/2016 | Seelig et al. |
| 2016/0251697 A1 | 9/2016 | Nolan |
| 2017/0009274 A1 | 1/2017 | Abate |
| 2017/0017436 A1 | 1/2017 | Church |
| 2017/0137806 A1 | 5/2017 | Jaitin |
| 2018/0016609 A1 | 1/2018 | Chen |
| 2018/0023108 A1 | 1/2018 | Chen |
| 2018/0030515 A1 | 2/2018 | Regev |
| 2018/0201968 A1 | 7/2018 | Chen |
| 2018/0340939 A1 | 11/2018 | Gaublomme |
| 2018/0341744 A1 | 11/2018 | Regev |
| 2018/0362969 A1 | 12/2018 | Banal |
| 2019/0040459 A1 | 2/2019 | Efcavitch |
| 2019/0078065 A1 | 3/2019 | Baiga et al. |
| 2019/0078126 A1 | 3/2019 | Baiga et al. |
| 2019/0144905 A1 | 5/2019 | Chen |
| 2019/0194739 A1 | 6/2019 | Efcavitch |
| 2019/0218276 A1 | 7/2019 | Regev |
| 2019/0218594 A1 | 7/2019 | Abate |
| 2019/0285644 A1 | 9/2019 | Regev |
| 2019/0300923 A1 | 10/2019 | Ybert et al. |
| 2019/0338331 A1 | 11/2019 | Chen |
| 2019/0344239 A1 | 11/2019 | Efcavitch |
| 2020/0002690 A1 | 1/2020 | Ybert et al. |
| 2020/0248255 A1 | 8/2020 | Buenrostro |
| 2021/0009994 A1 | 1/2021 | Godron et al. |

FOREIGN PATENT DOCUMENTS

| | | |
|---|---|---|
| EP | 1165786 | 7/2008 |
| EP | 2876166 | 5/2015 |
| EP | 3299469 | 3/2018 |
| JP | 04262799 | 9/1992 |
| WO | 199106678 | 5/1991 |
| WO | 199607669 | 3/1996 |

(56) References Cited

FOREIGN PATENT DOCUMENTS

| | | |
|---|---|---|
| WO | 1999019717 | 4/1999 |
| WO | 2000060072 | 10/2000 |
| WO | 2002024322 | 3/2002 |
| WO | 2004018497 | 3/2004 |
| WO | 2005005667 | 1/2005 |
| WO | 2005059096 | 6/2005 |
| WO | 2007147079 | 12/2007 |
| WO | 2008111990 | 9/2008 |
| WO | 2009145925 | 12/2009 |
| WO | 2014108850 | 7/2014 |
| WO | 2015159023 | 10/2015 |
| WO | 2016034807 | 3/2016 |
| WO | 2016040476 | 3/2016 |
| WO | 2016040594 | 3/2016 |
| WO | 2016168584 | 10/2016 |
| WO | 2017009663 | 1/2017 |
| WO | 2017075265 | 5/2017 |
| WO | 2017075292 | 5/2017 |
| WO | 2017216472 | 12/2017 |
| WO | 2018031631 | 2/2018 |
| WO | 2018031691 | 2/2018 |
| WO | 2018222853 | 12/2018 |
| WO | 2018236889 | 12/2018 |
| WO | 2019079802 | 4/2019 |
| WO | 2019084046 | 5/2019 |
| WO | 2019113506 | 6/2019 |
| WO | 2019135007 | 7/2019 |
| WO | 2019139650 | 7/2019 |
| WO | 2020118200 | 6/2020 |
| WO | 2020120442 | 6/2020 |
| WO | 2020123305 | 6/2020 |
| WO | 2020160044 | 8/2020 |

OTHER PUBLICATIONS

Zhu et al., "Reverse Transcriptase Template Switching: A SMART Approach for Full-Length cDNA Library Construction," BioTechniques 2001, 30:892-897. (Year: 2001).*
Gentile et al., "Click Chemistry-Based DNA Labeling of Cells for Barcoding Applications," Bioconjugate Chem. 2018, 29:2846-2854. (Year: 2018).
Non-Final Office Action dated Jul. 8, 2021 in related U.S. Appl. No. 16/970,590.
Notice of Allowance dated Oct. 28, 2021 mailed in related U.S. Appl. No. 16/970,590.
Thornhill et al., "A comparison of different lysis buffers to assess allele dropout from single cells for preimplantation genetic diagnosis," Prenatal Diagnosis, 21: 490-497 (2001). (Submitted in related U.S. Appl. No. 16/970,590).
Trombetta et al., "Preparation of single-cell RNA-seq libraries for next generation sequencing," Curr. Protocols Molecular Biol., 107: 4.22.1-4.22.17 (2015). (Submitted in related U.S. Appl. No. 16/970,590).
Ud-Dean, "A theoretical model for template-free synthesis of long DNA sequence," Syst. Synth. Biol., 2: 67-73 (2008). (Submitted in related U.S. Appl. No. 16/970,590).
Uemura et al., "Regioselective deprotection of 3', 5'-O-acylated pyrimidine nucleosides by lipase and esterase," Tetrahedron Lett., 30(29): 3819-3820 (1989). (Submitted in related U.S. Appl. No. 16/970,590).
Unger et al., "Monolithic Microfabricated Valves and Pumps by Multilayer Soft Lithography," Science, 288 (5463):113-116 (2000). (Submitted in related U.S. Appl. No. 16/970,590).
Uttamapinant et al., "Fast, cell-compatible click chemistry with copper-chelating azides for biomolecular labeling," Angew. Chem. Int. Ed., 51: 1-6 (2012). (Submitted in related U.S. Appl. No. 16/970,590).
Weber et al., "Efficient targeting of fatty acid modified oligonucleotides to live cell membranes through stepwise assembly," Biomacromolecules, 15: 4621-4626 (2014). (Submitted in related U.S. Appl. No. 16/970,590).

Williams et al., "Amplification of complex gene libraries by emulsion PCR," Nature Methods, 3(7): 545-550 (2006). (Submitted in related U.S. Appl. No. 16/970,590).
Wu et al., "3'-O-modified nucleotides as reversible terminators for pyrosequencing," Proc. Natl. Acad. Sci., 104(42): 16462-16467 (2007). (Submitted in related U.S. Appl. No. 16/970,590).
Wu, Thesis, "Molecular engineering of novel nucleotide analogues for DNA sequencing by synthesis," Columbia University, 2008. (Submitted in related U.S. Appl. No. 16/970,590).
Xiong et al., "Non-polymerase-cycling-assembly-based chemical gene synthesis: strategies, methods, and progress," Biotechnology Advances, 26: 121-134 (2008). (Submitted in related U.S. Appl. No. 16/970,590).
Xiong et al., "Chemical gene synthesis: strategies, softwares, error corrections, and applications," FEMS Microbiol. Rev., 32: 522-540 (2008). (Submitted in related U.S. Appl. No. 16/970,590).
Yang et al., "Mutational Analysis of Residues in the Nucleotide Binding Domain of Human Terminal Deoxynucleotidyl Transferase," The Journal of Biological Chemistry, 269(16): 11859-11868 (1994). (Submitted in related U.S. Appl. No. 16/970,590).
Yang et al., "T-cell specific avian TdT: characterization of the cDNA and recombinant enzyme," Nucleic Acids Research, 23(11): 2041-2048 (1995). (Submitted in related U.S. Appl. No. 16/970,590).
Yon et al., "Precise gene fusion by PCR," Nucleic Acids Res., 17(12): 4895 (1989). (Submitted in related U.S. Appl. No. 16/970,590).
Zagnoni et al., "Droplet microfluidics for high-throughput analysis of cells and particles," Methods in Cell Biology, 102: 25-48 (2011). (Submitted in related U.S. Appl. No. 16/970,590).
Zare et al., "Microfluidic Platforms for Single-Cell Analysis," Annual Review of Biomedical Engineering, 12:187-201 (2010). (Submitted in related U.S. Appl. No. 16/970,590).
Zeng et al., "High-performance single cell genetic analysis using microfluidic emulsion generator arrays," Anal. Chem., 82(8): 3183-3190 (2010). (Submitted in related U.S. Appl. No. 16/970,590).
Zheng et al., "Massively parallel digital transcriptional profiling of single cells," Nat Commun., 8:14049 (2017). (Submitted in related U.S. Appl. No. 16/970,590).
Zhu et al., "Reverse Transcriptase Template Switching: A SMART™ Approach for Full-Length cDNA Library Construction," BioTechniques, 30(4):892-897 (2018). (Submitted in related U.S. Appl. No. 16/970,590).
Zilionis et al., "Single-cell barcoding and sequencing using droplet microfluidics," Nature Protocols, 12(1): 44-73 (2017) (Submitted in related U.S. Appl. No. 16/970,590).
Zovgorodny et al., "1-Alkylthioalkylation of nucleoside hydroxyl functions and its synthetic applications: A new versatile method in nucleoside chemistry," Tetrahedron Lett., 32(51): 7593-7596 (1991). (Submitted in related U.S. Appl. No. 16/970,590).
Altschul et al., "Protein database searches using compositionally adjusted substitution matrices," FEBS Journal, 272: 5101-5109 (2005). (Submitted in related U.S. Appl. No. 16/970,590).
Altschul et al., "Gapped BLAST and PSI-BLAST: a new generation of protein database search programs," Nucleic Acids Research, 25(17): 3389-3402 (1997). (Submitted in related U.S. Appl. No. 16/970,590).
Grantham, "Amino acid difference formula to help explain protein evolution," Science, 185: 862-864 (1974). (Submitted in related U.S. Appl. No. 16/970,590).
Meng et al., "Design and Synthesis of a Photocleavable Fluorescent Nucleotide 3'-O-Allyl-dGTP-PC-Bodipy-FL-510 as a Reversible Terminator for DNA Sequencing by Synthesis," J. Org. Chem., 71: 3248-3252 (2006). (Submitted in related U.S. Appl. No. 16/970,590).
Needleman et al., "A general method applicable to the search for similarities in the amino acid sequence of two proteins," J. Mol. Biol., 48: 443-453 (1970). (Submitted in related U.S. Appl. No. 16/970,590).
Smith et al., "Identification of common molecular subsequences," J. Mol. Biol., 147:195-197 (1981). (Submitted in related U.S. Appl. No. 16/970,590).
Mali et al., "Barcoding cells using cell-surface programmable DNA-binding domains," Nat Methods 10, 403-406 (2013). https://doi.org/10.1038/nmeth.2407 (Year: 2013). (Submitted in related U.S. Appl. No. 16/970,590).

(56) References Cited

OTHER PUBLICATIONS

International Search Report dated Jun. 23, 2020 for International Application No. PCT/EP2019/084347. (Submitted in related U.S. Appl. No. 16/970,590).
Written Opinion dated Jun. 23, 2020 for International Application No. PCT/EP2019/084347. (Submitted in related U.S. Appl. No. 16/970,590).
Hinton, Deborah M., Catherine A. Brennan, and Richard I. Gumport. "The preparative synthesis of oligodeoxyribonucleotides using RNA ligase." Nucleic Acids Research 10.6 (1982): 1877-1894. (Submitted in related U.S. Appl. No. 16/970,590).
Dorkins, Huw R., and Kay E. Davies. "Recombinant DNA technology in the clinical sciences." Trends in Biotechnology 3.8 (1985): 195-199. (Submitted in related U.S. Appl. No. 16/970,590).
Chang, Lucy MS, F. J. Bollum, and Robert C. Gallo. "Molecular biology of terminal transferas." Critical Reviews in Biochemistry 21.1 (1986): 27-52. (Submitted in related U.S. Appl. No. 16/970,590).
Baskin et al., "Copper-free click chemistry for dynamic in vivo imaging," Proc. Natl. Acad. Sci., 104(43): 16793-16797 (2007). (Submitted in related U.S. Appl. No. 16/970,590).
Beabealashvilli et al., "Nucleoside 5'-triphosphates modified at sugar residues as substrates for calf thymus terminal deoxynucleotidyl transferase and for AMV reverse transcriptase," Biochim. Biophys. Acta., 868(2-3): 136-144 (1986). (Submitted in related U.S. Appl. No. 16/970,590).
Becker et al., "The Enzymatic Cleavage of Phosphate Termini from Polynucleotides," J. Biol. Chem., 242(5): 935-950 (1967). (Submitted in related U.S. Appl. No. 16/970,590).
Behbehani et al., "Transient Partial Permeabilization with Saponin Enables Cellular Barcoding Prior to Surface Marker Staining," Cytometry, 85A: 1011-1019 (2014). (Submitted in related U.S. Appl. No. 16/970,590).
Berdis et al., "The Use of Non-natural Nucleotides to Probe Template-Independent DNA Synthesis," ChemBioChem 2007, 8(12): 1399-1408. (Submitted in related U.S. Appl. No. 16/970,590).
Borisenko et al., "DNA modification of live cell surface," Nucleic Acids Research, 37(4): e28 (2009). (Submitted in related U.S. Appl. No. 16/970,590).
Borjesson et al., "Membrane-Anchored DNA assembly for Energy and Electron Transfer," J. Amer. Chem. Soc., 131: 2831-2839 (2009). (Submitted in related U.S. Appl. No. 16/970,590).
Brenner et al., "In vitro cloning of complex mixtures of DNA on microbeads: Physical separation of differentially expressed cDNAs," Proc. Natl. Acad. Sci., Feb. 15, 2000, 97 (4) 1665-1670. (Submitted in related U.S. Appl. No. 16/970,590).
Brouzes et al., "Droplet microfluidic technology for single-cell high-throughput screening," Proc. Natl. Acad. Sci., 106 (34): 14195-14200 (2009). (Submitted in related U.S. Appl. No. 16/970,590).
Brown et al., "Current techniques for single-cell lysis," J. R. Soc. Interface, 5: S131-S138 (2008). (Submitted in related U.S. Appl. No. 16/970,590).
Bunge et al., "Lipophilic oligonucleotides spontaneously insert into lipid membranes, bind complementary DNA strands, and sequester into lipid-disordered domains," Langmuir, 23: 4455-4464 (2007). (Submitted in related U.S. Appl. No. 16/970,590).
Bunge et al., "Lipid membranes carrying lipophilic cholesterol-based oligonucleotides—characterization and application on layer-by-layer coated particles," J. Phys. Chem. B, 113: 16425-16434 (2009). (Submitted in related U.S. Appl. No. 16/970,590).
Cameron et al., "3'-phosphatase activity in T4 polynucleotide kinase," Biochemistry, 16(23): 5120-5126 (1977). (Submitted in related U.S. Appl. No. 16/970,590).
Canard et al., "DNA polymerase fluorescent substrates with reversible 3'-tags," Gene, 148: 1-6 (1994). (Submitted in related U.S. Appl. No. 16/970,590).
Canard et al., "Catalytic editing properties of DNA polymerases," Proc. Natl. Acad. Sci., 92: 10859-10863 (1995). (Submitted in related U.S. Appl. No. 16/970,590).

Cao et al., "Comprehensive single cell transcriptional profiling of a multicellular organism by combinatorial indexing," bioRxiv, http://dx.doi.org/10.1101/104844 (Feb. 2, 2017). (Submitted in related U.S. Appl. No. 16/970,590).
Chang et al., "Copper-free click chemisty in living animals," Proc. Natl. Acad. Sci., 107(5): 1821-1826 (2010). (Submitted in related U.S. Appl. No. 16/970,590).
Chen et al., "Total gene synthesis: novel single-step and convergent strategies applied to the construction of a 779 base pair bacteriorhodopsin gene," J. Amer. Chem. Soc., 116: 8799-8800 (1994). (Submitted in related U.S. Appl. No. 16/970,590).
Chen et al., "Microfluidic cell sorter with integrated piezoelectric actuator," Biomed Microdevices, 11: 1223-1231 (2009). (Submitted in related U.S. Appl. No. 16/970,590).
Chen et al., "The history and advances of reversible terminators used in new generations of sequencing technology," Genomics Proteomics Bioinformatics, 11: 34-40 (2013). (Submitted in related U.S. Appl. No. 16/970,590).
Delarue et al., "Crystal structures of a template-independent DNA polymerase: murine terminal deoxynucleotidyltransferase," EMBO J., 21(3): 427-439 (2002). (Submitted in related U.S. Appl. No. 16/970,590).
Delort et al., ",Excision of uracil residues in DNA: mechanism of action of *Escherichia coli* and *Micrococcus luteus* uracil-DNA glycosylases," Nucleic Acids Research, 13(2):319-335 (1985). (Submitted in related U.S. Appl. No. 16/970,590).
Diehl et al., "BEAMING: single-molecule PCR on microparticles in water-in-oil emulsions," Nature Methods, 3(7): 551-559 (2006). (Submitted in related U.S. Appl. No. 16/970,590).
Edd et al., "Controlled encapsulation of single-cells into monodisperse picoliter droplets," Twelfth International Conference on Miniaturized Systems for Chemistry and Life Sciences, Oct. 12-16, 2008, San Diego, California. (Submitted in related U.S. Appl. No. 16/970,590).
EURx, Micellula DNA emulsion & purification kit instructions (2019). (Submitted in related U.S. Appl. No. 16/970,590).
Di Carlo et al., "Introduction: why analyze single cells?" Methods in Molecular Biology, 853: 1-10 (2012). (Submitted in related U.S. Appl. No. 16/970,590).
Dolomite Bio, "High Throughput Single Cell RNA-Seq," Application Note (Jul. 2017). (Submitted in related U.S. Appl. No. 16/970,590).
Dressman et al., "Transforming single DNA molecules into fluorescent magnetic particles for detection and enumeration of genetic variations," Proc. Natl. Acad. Sci., 100(15): 8817-8822 (2003). (Submitted in related U.S. Appl. No. 16/970,590).
Fan et al., "Combinatorial labeling of single cells for gene expression cytometry," Science, 347 (6222): 1258367-1 (2015) (Submitted in related U.S. Appl. No. 16/970,590).
Ferrero et al., "Chemoenzymatic transformations in nucleoside chemistry," Monatshefte fur Chemie, 131: 585-616 (2000). (Submitted in related U.S. Appl. No. 16/970,590).
Flickinger et al., "Differential incorporation of biotinylated nucleotides by terminal deoxynucleotidyl transferase," Nucleic Acids Research, 20(9): 2382 (1992). (Submitted in related U.S. Appl. No. 16/970,590).
Fomina et al., "An electrochemical platform for localized pH control on demand," Lab on a Chip, 16:2236-2244 (2016). (Submitted in related U.S. Appl. No. 16/970,590).
Fu et al., "Counting individual DNA mol.ecules by the stochastic attachment of diverse labels," Proc. Natl. Acad. Sci., May 31, 2011, 108 (22):9026-9031. (Submitted in related U.S. Appl. No. 16/970,590).
Fu et al., "Digital encoding of cellular mRNAs enabling precise and absolute gene expression measurement by single-molecule counting," Analytical Chemistry, 86: 2867-2870 (2014). (Submitted in related U.S. Appl. No. 16/970,590).
Gebeyehu et al., "Novel biotinylated nucleotide-analogs for labeling and colorimetric detection of DNA," Nucleic Acids Research, 15(11): 4513-4534 (1987). (Submitted in related U.S. Appl. No. 16/970,590).
Gong et al., "Simple Method to Prepare Oligonucleotide-Conjugated Antibodies and Its Application in Multiplex Protein Detection in Single Cells," Bioconjugate Chem. 2016, 27:217-225 (2016). (Submitted in related U.S. Appl. No. 16/970,590).
Guo et al., "Four-color DNA sequencing with 3'-O-modified nucleotide reversible terminators and chemically cleavable fluorescent

(56) References Cited

OTHER PUBLICATIONS dideoxynucleotides," Proc. Natl. Acad. Sci., 105(27): 9145-9150 (2008). (Submitted in related U.S. Appl. No. 16/970,590).
Guo et al., "An integrated system for DNA sequencing by synthesis using novel nucleotide analogues," Acc. Chem. Res., 43(4): 551-563 (2010). (Submitted in related U.S. Appl. No. 16/970,590).
Haeberle et al., "Microfluidic platforms for lab-on-a-chip applications," Lab on a Chip, 7:1094-1110 (2007). (Submitted in related U.S. Appl. No. 16/970,590).
Hoover et al., "DNAWorks: an automated method for designing oligonucleotides for PCR-based gene synthesis," Nucleic Acids Research, 30(10):e43 (2002). (Submitted in related U.S. Appl. No. 16/970,590).
Horisawa, "Specific and quantitative labeling of biomolecules using click chemistry," Front. Physiol., 5:1-6 (2014). (Submitted in related U.S. Appl. No. 16/970,590).
Hutter et al., "Labeled nucleoside triphosphates with reversibly terminating aminoalkoxyl groups," Nucleosides, Nucleotides & Nucleic Acids, 29(11): 879-895 (2010). (Submitted in related U.S. Appl. No. 16/970,590).
IPR2013-00128 re U.S. Pat. No. 7,057,026 Final Written Decision (Jul. 25, 2014). (Submitted in related U.S. Appl. No. 16/970,590).
IPR2013-00266 re U.S. Pat. No. 8,158,346 Final Written Decision (Oct. 28, 2014). (Submitted in related U.S. Appl. No. 16/970,590).
IPR2017-02172 re U.S. Pat. No. 7,566,537 Decision Denying Institution (Apr. 20, 2018). (Submitted in related U.S. Appl. No. 16/970,590).
Islam et al., "Quantitative single-cell RNA-seq with unique molecular identifiers," Nature Methods, 11(2): 163-166 (2014). (Submitted in related U.S. Appl. No. 16/970,590).
Jawalekar et al., "Oligonucleotide tagging for copper-free click conjugation," Molecules, 18: 7346-7363 (2013). (Submitted in related U.S. Appl. No. 16/970,590).
Jensen et al., "Template-independent enzymatic oligonucleotide synthesis (TiEOS): Its history, prospects, and challenges," Biochemistry, 57: 1821-1832 (2018). (Submitted in related U.S. Appl. No. 16/970,590).
Jewett et al., "Cu-free click cycloaddition reactions in chemical biology," Chem. Soc. Rev., 39(4): 1272-1279 (2010). (Submitted in related U.S. Appl. No. 16/970,590).
Ju et al., "Four-color DNA sequencing by synthesis using cleavable fluorescent nucleotide reversible terminators," Proc. Natl. Acad. Sci., 103(52): 19635-19640 (2006). (Submitted in related U.S. Appl. No. 16/970,590).
Kazane et al., "Site-specific DNA-antibody conjugates for specific and sensitive immuno-PCR," Proc. Natl. Acad. Sci., 109(10):3731-3736 (2012). (Submitted in related U.S. Appl. No. 16/970,590).
Kebschull et al., "Cellular barcoding: lineage tracing, screening and beyond," Nature Methods, 15: 871-879 (2018). (Submitted in related U.S. Appl. No. 16/970,590).
Kim et al., "An efficient and reliable DNA extraction method for preimplantation genetic diagnosis: a comparison of allele drop out and amplification rates using different single cell lysis methods," Fertility and Sterility, 92(2), Aug. 2009. (Submitted in related U.S. Appl. No. 16/970,590).
Kim et al., "Single-cell RT-PCR in microfluidic droplets with integrated chemical lysis," Analytical Chemistry, 90: 1273-1279 (2018). (Submitted in related U.S. Appl. No. 16/970,590).
Kinde et al., "Detection and quantification of rare mutations with massively parallel sequencing," Proc. Natl. Acad. Sci., Jun. 7, 2011, 108(23):9530-9535. (Submitted in related U.S. Appl. No. 16/970,590).
Klein et al., "Droplet barcoding for single-cell transcriptomics applied to embryonic stem cells," Cell, 161: 1187-1201 (2015). (Submitted in related U.S. Appl. No. 16/970,590).
Knapp et al., "Fluoride-Cleavable, Fluorescently Labelled Reversible Terminators: Synthesis and Use in Primer Extension," Chem. Eur. J., 17: 2903-2915 (2011). (Submitted in related U.S. Appl. No. 16/970,590).

Kobayashi et al., "A microfluidic device for conducting gas-liquid-solid hydrogenation reactions," Science, 304: 1305-1308 (2004). (Submitted in related U.S. Appl. No. 16/970,590).
Kolodziejczyk et al., "The Technology and Biology of Single-Cell RNA Sequencing," Molecular Cell, 58(4): 610-620 (2015). (Submitted in related U.S. Appl. No. 16/970,590).
Kore et al., "Synthesis and activity of modified cytidine 5'-monophosphate probes for T4 RNA ligase 1," Nucleosides Nucleotides Nucleic Acids, 28(4): 292-302 (2009). (Submitted in related U.S. Appl. No. 16/970,590).
Koster et al., "Drop-based microfluidic devices for encapsulation of single cells," Lab on a Chip 8:1110-1115 (2008). (Submitted in related U.S. Appl. No. 16/970,590).
Lee et al., "Terminator-free template independent enzymatic DNA synthesis for digital information storage," Nature Comm., 10:2383 (2019). (Submitted in related U.S. Appl. No. 16/970,590).
Le Gac et al., "Single cell electroporation using microfluidic devices," chapter 7, Methods in Molecular Biology, 853: 65-82 (2011). (Submitted in related U.S. Appl. No. 16/970,590).
Leone et al., "Molecular beacon probes combined with amplification by NASBA enable homogeneous, real-time detection of RNA," Nucleic Acids Research, 26(9): 2150-2155 (1998). (Submitted in related U.S. Appl. No. 16/970,590).
Levine et al., "Active CMOS Sensor Array for Electrochemical Biomolecular Detection," IEEE Journal of Solid-State Circuits, 43(8):1859-1871 (2008). (Submitted in related U.S. Appl. No. 16/970,590).
Li et al., "A photocleavable fluorescent nucleotide for DNA sequencing and analysis," Proc. Natl. Acad. Sci., 100(2): 414-419 (2003). (Submitted in related U.S. Appl. No. 16/970,590).
Li et al., "Copper-catalyzed click reaction on/in live cells," Chemical Science, 8: 2107 (2017). (Submitted in related U.S. Appl. No. 16/970,590).
Lin et al., "Recent patents and advances in the next-generation sequencing technologies," Recent Patents in Biomedical Engineering, 2008(1): 60-67 (2008). (Submitted in related U.S. Appl. No. 16/970,590).
Macosko et al., "Highly parallel genome-wide expression profiling of individual cells using nanoliter droplets," Cell, 161: 1202-1214 (2015). (Submitted in related U.S. Appl. No. 16/970,590).
Mathews et al., "Photo-cleavable nucleotides for primer free enzyme mediated DNA synthesis," Organic & Biomolecular Chemistry, 14: 8278 (2016). (Submitted in related U.S. Appl. No. 16/970,590).
Maurer et al., "Electrochemically Generated Acid and Its Containment to 100 Micron Reaction Areas for the Production of DNA Microarrays," PLosOne, Issue 1:e34 (2006). (Submitted in related U.S. Appl. No. 16/970,590).
Metzker et al., "Termination of DNA synthesis by novel 3'-modified-deoxyribonucleoside 5'-triphosphates," Nucleic Acids Research, Oct. 11, 1994, 22(20):4259-4267. (Submitted in related U.S. Appl. No. 16/970,590).
Michelson et al., "Characterization of the homopolymer tailing reaction catalyzed by terminal deoxynucleotidyl transferase," J. Biol. Chem., 257(24): 14773-14782 (1982). (Submitted in related U.S. Appl. No. 16/970,590).
Motea et al., "Terminal deoxynucleotidyl transferase: The story of a misguided DNA polymerase," Biochim Biophys Acta, 1804(5): 1151-1166 (2010). (Submitted in related U.S. Appl. No. 16/970,590).
Nagarajan et al., "Spatially resolved and multiplexed microRNA quantification from tissue using nanoliter well arrays," Microsystems & Nanoengineering, 6: 51 (2020). (Submitted in related U.S. Appl. No. 16/970,590).
Nakano et al., "Single-molecule PCR using water-in-oil emulsion," J. Biotechnology, 102: 117-124 (2003). (Submitted in related U.S. Appl. No. 16/970,590).
Nikic et al., "Labeling proteins on live mammalian cells using click chemistry," Nature Protocols, 10(5): 780-791 (2015). (Submitted in related U.S. Appl. No. 16/970,590).
Novak et al., "Single-cell multiplex gene detection and sequencing with microfluidically generated agarose emulsions," Angew. Chemie Int. Ed., 50: 390-395 (2011). (Submitted in related U.S. Appl. No. 16/970,590).

(56) References Cited

OTHER PUBLICATIONS

Olejnik et al., "Photocleavable biotin derivatives: A versatile approach for the isolation of biomolecules," Proc. Natl. Acad. Sci., 92: 7590-7594 (1995). (Submitted in related U.S. Appl. No. 16/970,590).

Palla et al., "DNA sequencing by synthesis using 3'-O-azidomethyl nucleotide reversible terminators and surface-enhanced Raman spectroscopic detection," RCS Adv. 4: 49342 (2014). (Submitted in related U.S. Appl. No. 16/970,590).

Petrie et al., "A novel biotinylated adenylate analogue derived from pyrazolo[3,4-d] pyrimidine for labeling DNA probes," Bioconjug. Chem., 2(6): 441-446 (1991). (Submitted in related U.S. Appl. No. 16/970,590).

Rasolonjatovo et al., "Development of a new sequencing method: 3'-ester cleavage catalyzed by Taq DNA polymerase," Nucleosides & Nucleotides, 18(4&5): 1021-1022 (1999). (Submitted in related U.S. Appl. No. 16/970,590).

Saliba et al., "Single-cell RNA-seq: advances and future challenges," Nucleic Acids Research, 42(14): 8845-8860 (2014). (Submitted in related U.S. Appl. No. 16/970,590).

Sano et al., "Immuno-PCR: very sensitive antigen detection by means of specific antibody-DNA conjugates," Science 258: 120-122 (1992). (Submitted in related U.S. Appl. No. 16/970,590).

Saxon et al., "Cell surface engineering by a modified Staudinger reaction," Science, 287: 2007-2010 (2000). (Submitted in related U.S. Appl. No. 16/970,590).

Schmitz et al., "Solid-phase enzymatic synthesis of oligonucleotides," Organic Lett., 1(11): 1729-1731 (1999). (Submitted in related U.S. Appl. No. 16/970,590).

Schott et al., "Single-step elongation of oligodeoxynucleotides using terminal deoxynucleotidyl transferase," Eur. J. Biochem., 143: 613-620 (1984). (Submitted in related U.S. Appl. No. 16/970,590).

Shapiro et al., "Single-cell sequencing-based technologies will revolutionize whole-organism science," Nature Reviews Genetics, 14: 618-630 (2013). (Submitted in related U.S. Appl. No. 16/970,590).

Shoemaker et al., "Quantitative phenotypic analysis of yeast deletion mutants using a highly parallel molecular bar-coding strategy," Nature Genetics, 14:450-456 (1996). (Submitted in related U.S. Appl. No. 16/970,590).

Sia et al., "Microfluidic devices fabricated in poly(dimethylsiloxane) for biological studies," Electrophoresis, 24: 3563-3576 (2003). (Submitted in related U.S. Appl. No. 16/970,590).

Stahl et al., "Visualization and analysis of gene expression in tissue sections by spatial transcriptomics," Science, 353 (6294): 78-82 (2016). (Submitted in related U.S. Appl. No. 16/970,590).

Stemmer et al., "Single-step assembly of a gene and entire plasmid from large numbers of oligodeoxyribonucleotides," Gene, 164: 49-53 (1995). (Submitted in related U.S. Appl. No. 16/970,590).

Tang et al., "RNA-seq analysis to capture the transcriptome landscape of a single cell," Nature Protocols, 5(3): doi:10.1038/nprot. 2009.236 (2010). (Submitted in related U.S. Appl. No. 16/970,590).

Taunton-Rigby, "Oligonucleotide synthesis. III. Enzymatically removable acyl protecting groups," J. Org. Chem., 38(5): 977-985 (1973). (Submitted in related U.S. Appl. No. 16/970,590).

Tawfik et al., "Man-made cell-like compartments for molecular evolution," Nature Biotechnology, 16: 652-656 (1998). (Submitted in related U.S. Appl. No. 16/970,590).

\* cited by examiner

Viable Cell

Fixed and Permeabilized Cell

SEQUENCE LISTING

<160> NUMBER OF SEQ ID NOS: 18

<210> SEQ ID NO 1
<211> LENGTH: 510
<212> TYPE: PRT
<213> ORGANISM: ARTIFICIAL SEQUENCE
<220> FEATURE:
<223> OTHER INFORMATION: TDT enzyme

<400> SEQUENCE: 1

Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365

Trp Lys Gln Gln Gly Leu Leu Leu Tyr Cys Asp Ile Leu Glu Ser Thr
    370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His

```
            405                 410                 415
Ser Glu Lys Ser Gly Gln Gln Glu Gly Lys Gly Trp Lys Ala Ile Arg
            420                 425                 430

Val Asp Leu Val Met Cys Pro Tyr Asp Arg Arg Ala Phe Ala Leu Leu
            435                 440                 445

Gly Trp Thr Gly Ser Arg Gln Phe Glu Arg Asp Leu Arg Arg Tyr Ala
            450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Glu Ile Phe Ala
                485                 490                 495

His Leu Gly Leu Asp Tyr Ile Glu Pro Trp Glu Arg Asn Ala
            500                 505                 510

<210> SEQ ID NO 2
<211> LENGTH: 381
<212> TYPE: PRT
<213> ORGANISM: ARTIFICIAL SEQUENCE
<220> FEATURE:
<223> OTHER INFORMATION: truncated mouse sequence

<400> SEQUENCE: 2

Asn Ser Ser Pro Ser Pro Val Pro Gly Ser Gln Asn Val Pro Ala Pro
1               5                   10                  15

Ala Val Lys Lys Ile Ser Gln Tyr Ala Cys Gln Arg Arg Thr Thr Leu
                20                  25                  30

Asn Asn Tyr Asn Gln Leu Phe Thr Asp Ala Leu Asp Ile Leu Ala Glu
            35                  40                  45

Asn Asp Glu Leu Arg Glu Asn Glu Gly Ser Cys Leu Ala Phe Met Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Ala Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Cys Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Arg Gly
        195                 200                 205

Lys Met Thr Gly His Asp Val Asp Phe Leu Ile Thr Ser Pro Glu Ala
    210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
```

```
                 260                 265                 270
Gln Lys Cys Phe Leu Ile Leu Lys Leu Asp His Gly Arg Val His Ser
            275                 280                 285

Glu Lys Ser Gly Gln Gln Glu Gly Lys Gly Trp Lys Ala Ile Arg Val
        290                 295                 300

Asp Leu Val Met Cys Pro Tyr Asp Arg Arg Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Arg Thr
            340                 345                 350

Lys Arg Val Phe Leu Glu Ala Glu Ser Glu Glu Ile Phe Ala His
        355                 360                 365

Leu Gly Leu Asp Tyr Ile Glu Pro Trp Glu Arg Asn Ala
    370                 375                 380

<210> SEQ ID NO 3
<211> LENGTH: 380
<212> TYPE: PRT
<213> ORGANISM: ARTIFICIAL SEQUENCE
<220> FEATURE:
<223> OTHER INFORMATION: Bovine truncated (catalytic domain):

<400> SEQUENCE: 3

Asp Tyr Ser Ala Thr Pro Asn Pro Gly Phe Gln Lys Thr Pro Pro Leu
1               5                   10                  15

Ala Val Lys Lys Ile Ser Gln Tyr Ala Cys Gln Arg Lys Thr Thr Leu
            20                  25                  30

Asn Asn Tyr Asn His Ile Phe Thr Asp Ala Phe Glu Ile Leu Ala Glu
        35                  40                  45

Asn Ser Glu Phe Lys Glu Asn Glu Val Ser Tyr Val Thr Phe Met Arg
    50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Asp Lys Val Lys Cys Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Ser
    130                 135                 140

Leu Ser Lys Ile Met Ser Asp Lys Thr Leu Lys Phe Thr Lys Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Trp Ala
            180                 185                 190

Phe Leu Pro Asp Ala Phe Val Thr Met Thr Gly Gly Phe Arg Arg Gly
        195                 200                 205

Lys Lys Ile Gly His Asp Val Asp Phe Leu Ile Thr Ser Pro Gly Ser
    210                 215                 220

Ala Glu Asp Glu Glu Gln Leu Leu Pro Lys Val Ile Asn Leu Trp Glu
225                 230                 235                 240

Lys Lys Gly Leu Leu Leu Tyr Tyr Asp Leu Val Glu Ser Thr Phe Glu
```

```
                         245                 250                 255
Lys Phe Lys Leu Pro Ser Arg Gln Val Asp Thr Leu Asp His Phe Gln
            260                 265                 270

Lys Cys Phe Leu Ile Leu Lys Leu His His Gln Arg Val Asp Ser Ser
            275                 280                 285

Lys Ser Asn Gln Gln Glu Gly Lys Thr Trp Lys Ala Ile Arg Val Asp
            290                 295                 300

Leu Val Met Cys Pro Tyr Glu Asn Arg Ala Phe Ala Leu Leu Gly Trp
305                 310                 315                 320

Thr Gly Ser Arg Gln Phe Glu Arg Asp Ile Arg Arg Tyr Ala Thr His
                325                 330                 335

Glu Arg Lys Met Met Leu Asp Asn His Ala Leu Tyr Asp Lys Thr Lys
                340                 345                 350

Arg Val Phe Leu Lys Ala Glu Ser Glu Glu Ile Phe Ala His Leu
                355                 360                 365

Gly Leu Asp Tyr Ile Glu Pro Trp Glu Arg Asn Ala
            370                 375                 380

<210> SEQ ID NO 4
<211> LENGTH: 380
<212> TYPE: PRT
<213> ORGANISM: ARTIFICIAL SEQUENCE
<220> FEATURE:
<223> OTHER INFORMATION: Human truncated

<400> SEQUENCE: 4

Asp Tyr Ser Asp Ser Thr Asn Pro Gly Pro Pro Lys Thr Pro Pro Ile
1               5                   10                  15

Ala Val Gln Lys Ile Ser Gln Tyr Ala Cys Gln Arg Arg Thr Thr Leu
                20                  25                  30

Asn Asn Cys Asn Gln Ile Phe Thr Asp Ala Phe Asp Ile Leu Ala Glu
            35                  40                  45

Asn Cys Glu Phe Arg Glu Asn Glu Asp Ser Cys Val Thr Phe Met Arg
        50                  55                  60

Ala Ala Ser Val Leu Lys Ser Leu Pro Phe Thr Ile Ile Ser Met Lys
65                  70                  75                  80

Asp Thr Glu Gly Ile Pro Cys Leu Gly Ser Lys Val Lys Gly Ile Ile
                85                  90                  95

Glu Glu Ile Ile Glu Asp Gly Glu Ser Ser Glu Val Lys Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ser Glu Lys Trp Phe Arg Met Gly Phe Arg Thr
130                 135                 140

Leu Ser Lys Val Arg Ser Asp Lys Ser Leu Lys Phe Thr Arg Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Ser Val Leu Val Lys Glu Ala Val Trp Ala
            180                 185                 190

Phe Leu Pro Asp Ala Phe Val Thr Met Thr Gly Gly Phe Arg Arg Gly
        195                 200                 205

Lys Lys Met Gly His Asp Val Asp Phe Leu Ile Thr Ser Pro Gly Ser
    210                 215                 220

Thr Glu Asp Glu Glu Gln Leu Leu Gln Lys Val Met Asn Leu Trp Glu
```

```
            225                 230                 235                 240
        Lys Lys Gly Leu Leu Leu Tyr Tyr Asp Leu Val Glu Ser Thr Phe Glu
                        245                 250                 255

Lys Leu Arg Leu Pro Ser Arg Lys Val Asp Ala Leu Asp His Phe Gln
                        260                 265                 270

Lys Cys Phe Leu Ile Phe Lys Leu Pro Arg Gln Arg Val Asp Ser Asp
                        275                 280                 285

Gln Ser Ser Trp Gln Glu Gly Lys Thr Trp Lys Ala Ile Arg Val Asp
                290                 295                 300

Leu Val Leu Cys Pro Tyr Glu Arg Arg Ala Phe Ala Leu Leu Gly Trp
        305                 310                 315                 320

Thr Gly Ser Arg Gln Phe Glu Arg Asp Leu Arg Arg Tyr Ala Thr His
                        325                 330                 335

Glu Arg Lys Met Ile Leu Asp Asn His Ala Leu Tyr Asp Lys Thr Lys
                        340                 345                 350

Arg Ile Phe Leu Lys Ala Glu Ser Glu Glu Ile Phe Ala His Leu
                        355                 360                 365

Gly Leu Asp Tyr Ile Glu Pro Trp Glu Arg Asn Ala
                370                 375                 380

<210> SEQ ID NO 5
<211> LENGTH: 376
<212> TYPE: PRT
<213> ORGANISM: ARTIFICIAL SEQUENCE
<220> FEATURE:
<223> OTHER INFORMATION: Chicken 1 truncated

<400> SEQUENCE: 5

Gln Tyr Pro Thr Leu Lys Thr Pro Glu Ser Glu Val Ser Ser Phe Thr
        1               5                   10                  15

Ala Ser Lys Val Ser Gln Tyr Ser Cys Gln Arg Lys Thr Thr Leu Asn
                        20                  25                  30

Asn Cys Asn Lys Lys Phe Thr Asp Ala Phe Glu Ile Met Ala Glu Asn
                        35                  40                  45

Tyr Glu Phe Lys Glu Asn Glu Ile Phe Cys Leu Glu Phe Leu Arg Ala
                50                  55                  60

Ala Ser Val Leu Lys Ser Leu Pro Phe Pro Val Thr Arg Met Lys Asp
        65                  70                  75                  80

Ile Gln Gly Leu Pro Cys Met Gly Asp Arg Val Arg Asp Val Ile Glu
                        85                  90                  95

Glu Ile Ile Glu Glu Gly Glu Ser Ser Arg Ala Lys Val Leu Asn
                        100                 105                 110

Asp Glu Arg Tyr Lys Ser Phe Lys Glu Phe Thr Ser Val Phe Gly Val
                        115                 120                 125

Gly Val Lys Thr Ser Glu Lys Trp Phe Arg Met Gly Leu Arg Thr Val
                130                 135                 140

Glu Glu Val Lys Ala Asp Lys Thr Leu Lys Leu Ser Lys Met Gln Arg
        145                 150                 155                 160

Ala Gly Phe Leu Tyr Tyr Glu Asp Leu Val Ser Cys Val Ser Lys Ala
                        165                 170                 175

Glu Ala Asp Ala Val Ser Ser Ile Val Lys Asn Thr Val Cys Thr Phe
                        180                 185                 190

Leu Pro Asp Ala Leu Val Thr Ile Thr Gly Gly Phe Arg Arg Gly Lys
                        195                 200                 205

Lys Ile Gly His Asp Ile Asp Phe Leu Ile Thr Ser Pro Gly Gln Arg
```

```
            210                 215                 220
Glu Asp Asp Glu Leu Leu His Lys Gly Leu Leu Leu Tyr Cys Asp Ile
225                 230                 235                 240

Ile Glu Ser Thr Phe Val Lys Glu Gln Ile Pro Ser Arg His Val Asp
                245                 250                 255

Ala Met Asp His Phe Gln Lys Cys Phe Ala Ile Leu Lys Leu Tyr Gln
                260                 265                 270

Pro Arg Val Asp Asn Ser Ser Tyr Asn Met Ser Lys Lys Cys Asp Met
            275                 280                 285

Ala Glu Val Lys Asp Trp Lys Ala Ile Arg Val Asp Leu Val Ile Thr
        290                 295                 300

Pro Phe Glu Gln Tyr Ala Tyr Ala Leu Leu Gly Trp Thr Gly Ser Arg
305                 310                 315                 320

Gln Phe Gly Arg Asp Leu Arg Arg Tyr Ala Thr His Glu Arg Lys Met
                325                 330                 335

Met Leu Asp Asn His Ala Leu Tyr Asp Lys Arg Lys Val Phe Leu
                340                 345                 350

Lys Ala Gly Ser Glu Glu Ile Phe Ala His Leu Gly Leu Asp Tyr
            355                 360                 365

Val Glu Pro Trp Glu Arg Asn Ala
    370                 375

<210> SEQ ID NO 6
<211> LENGTH: 387
<212> TYPE: PRT
<213> ORGANISM: ARTIFICIAL SEQUENCE
<220> FEATURE:
<223> OTHER INFORMATION: Possum truncated

<400> SEQUENCE: 6

Ser Ala Asn Pro Asp Pro Thr Ala Gly Thr Leu Asn Ile Leu Pro Pro
1               5                   10                  15

Thr Thr Lys Thr Ile Ser Gln Tyr Ala Cys Gln Arg Arg Thr Thr Ile
            20                  25                  30

Asn Asn His Asn Gln Arg Phe Thr Asp Ala Phe Glu Ile Leu Ala Lys
        35                  40                  45

Asn Tyr Glu Phe Lys Glu Asn Asp Asp Thr Cys Leu Thr Phe Met Arg
50                  55                  60

Ala Ile Ser Val Leu Lys Cys Leu Pro Phe Glu Val Val Ser Leu Lys
65                  70                  75                  80

Asp Thr Glu Gly Leu Pro Trp Ile Gly Asp Glu Val Lys Gly Ile Met
                85                  90                  95

Glu Glu Ile Ile Glu Asp Gly Glu Ser Leu Glu Val Gln Ala Val Leu
            100                 105                 110

Asn Asp Glu Arg Tyr Gln Ser Phe Lys Leu Phe Thr Ser Val Phe Gly
        115                 120                 125

Val Gly Leu Lys Thr Ala Asp Lys Trp Tyr Arg Met Gly Phe Arg Thr
130                 135                 140

Leu Asn Lys Ile Arg Ser Asp Lys Thr Leu Lys Leu Thr Lys Met Gln
145                 150                 155                 160

Lys Ala Gly Leu Cys Tyr Tyr Glu Asp Leu Ile Asp Cys Val Ser Lys
                165                 170                 175

Ala Glu Ala Asp Ala Val Ser Leu Leu Val Gln Asp Ala Val Trp Thr
            180                 185                 190

Phe Leu Pro Asp Ala Leu Val Thr Ile Thr Gly Gly Phe Arg Arg Gly
```

```
            195                 200                 205
Lys Glu Phe Gly His Asp Val Asp Phe Leu Ile Thr Ser Pro Gly Ala
210                 215                 220

Glu Lys Glu Gln Glu Asp Gln Leu Leu Gln Lys Val Thr Asn Leu Trp
225                 230                 235                 240

Lys Lys Gln Gly Leu Leu Tyr Cys Asp Leu Ile Glu Ser Thr Phe
            245                 250                 255

Glu Asp Leu Lys Leu Pro Ser Arg Lys Ile Asp Ala Leu Asp His Phe
                260                 265                 270

Gln Lys Cys Phe Leu Ile Leu Lys Leu Tyr His His Lys Glu Asp Lys
            275                 280                 285

Arg Lys Trp Glu Met Pro Thr Gly Ser Asn Glu Ser Glu Ala Lys Ser
290                 295                 300

Trp Lys Ala Ile Arg Val Asp Leu Val Val Cys Pro Tyr Asp Arg Tyr
305                 310                 315                 320

Ala Phe Ala Leu Leu Gly Trp Ser Gly Ser Arg Gln Phe Glu Arg Asp
                325                 330                 335

Leu Arg Arg Tyr Ala Thr His Glu Lys Lys Met Met Leu Asp Asn His
            340                 345                 350

Ala Leu Tyr Asp Lys Thr Lys Lys Ile Phe Leu Lys Ala Lys Ser Glu
            355                 360                 365

Glu Glu Ile Phe Ala His Leu Gly Leu Glu Tyr Ile Gln Pro Ser Glu
370                 375                 380

Arg Asn Ala
385

<210> SEQ ID NO 7
<211> LENGTH: 381
<212> TYPE: PRT
<213> ORGANISM: ARTIFICIAL SEQUENCE
<220> FEATURE:
<223> OTHER INFORMATION: New truncated shrew

<400> SEQUENCE: 7

Asp Cys Pro Ala Ser His Asp Ser Pro Gln Lys Thr Glu Ser Ala
1               5                   10                  15

Ala Val Gln Lys Ile Ser Gln Tyr Ala Cys Gln Arg Arg Thr Thr Leu
                20                  25                  30

Asn Asn His Asn His Ile Phe Thr Asp Ala Phe Glu Ile Leu Ala Glu
            35                  40                  45

Asn Cys Glu Phe Arg Glu Asn Glu Gly Ser Tyr Val Thr Tyr Met Arg
    50                  55                  60

Ala Ala Ser Val Leu Lys Ser Leu Pro Phe Ser Ile Ile Ser Met Lys
65                  70                  75                  80

Asp Thr Glu Gly Ile Pro Cys Leu Ala Asp Lys Val Lys Cys Val Ile
                85                  90                  95

Glu Glu Ile Ile Glu Asp Gly Glu Ser Ser Val Lys Ala Val Leu
            100                 105                 110

Asn Asp Glu Arg Tyr Lys Ser Phe Lys Leu Phe Thr Ser Val Phe Gly
            115                 120                 125

Val Gly Leu Lys Thr Ala Glu Lys Trp Phe Arg Gly Phe Arg Thr
            130                 135                 140

Leu Ser Gly Ile Met Asn Asp Lys Thr Leu Lys Leu Thr His Met Gln
145                 150                 155                 160

Lys Ala Gly Phe Leu Tyr Tyr Glu Asp Leu Val Ser Cys Val Thr Arg
```

```
                165                 170                 175
Ala Glu Ala Glu Ala Val Gly Val Leu Val Lys Glu Ala Val Trp Ala
            180                 185                 190

Phe Leu Pro Asp Ala Ile Val Thr Met Thr Gly Gly Phe Arg Arg Gly
        195                 200                 205

Lys Lys Val Gly His Asp Val Asp Phe Leu Ile Thr Ser Pro Glu Ala
    210                 215                 220

Thr Glu Glu Gln Glu Gln Gln Leu Leu His Lys Val Ile Thr Phe Trp
225                 230                 235                 240

Glu Lys Glu Gly Leu Leu Leu Tyr Cys Asp Leu Tyr Glu Ser Thr Phe
                245                 250                 255

Glu Lys Leu Lys Met Pro Ser Arg Lys Val Asp Ala Leu Asp His Phe
            260                 265                 270

Gln Lys Cys Phe Leu Ile Leu Lys Leu His Arg Glu Cys Val Asp Asp
        275                 280                 285

Gly Thr Ser Ser Gln Leu Gln Gly Lys Thr Trp Lys Ala Ile Arg Val
    290                 295                 300

Asp Leu Val Val Cys Pro Tyr Glu Cys Arg Ala Phe Ala Leu Leu Gly
305                 310                 315                 320

Trp Thr Gly Ser Pro Gln Phe Glu Arg Asp Leu Arg Arg Tyr Ala Thr
                325                 330                 335

His Glu Arg Lys Met Met Leu Asp Asn His Ala Leu Tyr Asp Lys Thr
            340                 345                 350

Lys Arg Lys Phe Leu Ser Ala Asp Ser Glu Glu Asp Ile Phe Ala His
        355                 360                 365

Leu Gly Leu Asp Tyr Ile Glu Pro Trp Glu Arg Asn Ala
    370                 375                 380

<210> SEQ ID NO 8
<211> LENGTH: 387
<212> TYPE: PRT
<213> ORGANISM: ARTIFICIAL SEQUENCE
<220> FEATURE:
<223> OTHER INFORMATION: Python truncated

<400> SEQUENCE: 8

Glu Lys Tyr Gln Leu Pro Glu Asp Glu Asp Arg Ser Val Thr Ser Asp
1               5                   10                  15

Leu Asp Arg Asp Ser Ile Ser Glu Tyr Ala Cys Gln Arg Arg Thr Thr
            20                  25                  30

Leu Lys Asn Tyr Asn Gln Lys Phe Thr Asp Ala Phe Glu Ile Leu Ala
        35                  40                  45

Glu Asn Tyr Glu Phe Asn Glu Asn Lys Gly Phe Cys Thr Ala Phe Arg
    50                  55                  60

Arg Ala Ala Ser Val Leu Lys Cys Leu Pro Phe Thr Ile Val Gln Val
65                  70                  75                  80

His Asp Ile Glu Gly Val Pro Trp Met Gly Lys Gln Val Lys Gly Ile
                85                  90                  95

Ile Glu Asp Ile Ile Glu Glu Gly Ser Ser Lys Val Lys Ala Val
            100                 105                 110

Leu Asp Asn Glu Asn Tyr Arg Ser Val Lys Leu Phe Thr Ser Val Phe
        115                 120                 125

Gly Val Gly Leu Lys Thr Ser Asp Lys Trp Tyr Arg Met Gly Leu Arg
    130                 135                 140

Thr Leu Glu Glu Val Lys Arg Asp Lys Asn Leu Lys Leu Thr Arg Met
```

```
                145                 150                 155                 160
        Gln Lys Ala Gly Phe Leu His Tyr Asp Asp Leu Thr Ser Cys Val Ser
                        165                 170                 175

Lys Ala Glu Ala Asp Ala Ala Ser Leu Ile Val Gln Asp Val Val Trp
                        180                 185                 190

Lys Ile Val Pro Asn Ala Ile Val Thr Ile Ala Gly Phe Arg Arg
                        195                 200                 205

Gly Lys Gln Thr Gly His Asp Val Asp Phe Leu Ile Thr Val Pro Gly
                        210                 215                 220

Ser Lys Gln Glu Glu Glu Leu Leu His Thr Val Ile Asp Ile Trp
        225                 230                 235                 240

Lys Lys Gln Glu Leu Leu Leu Tyr Tyr Asp Leu Ile Glu Ser Thr Phe
                        245                 250                 255

Glu Asp Thr Lys Leu Pro Ser Arg Lys Val Asp Ala Leu Asp His Phe
                        260                 265                 270

Gln Lys Cys Phe Ala Ile Leu Lys Val His Lys Glu Arg Glu Asp Lys
                        275                 280                 285

Gly Asn Ser Ile Arg Ser Lys Ala Phe Ser Glu Glu Ile Lys Asp
                        290                 295                 300

Trp Lys Ala Ile Arg Val Asp Leu Val Val Val Pro Phe Glu Gln Tyr
        305                 310                 315                 320

Ala Phe Ala Leu Leu Gly Trp Thr Gly Ser Thr Gln Phe Glu Arg Asp
                        325                 330                 335

Leu Arg Arg Tyr Ala Thr His Glu Lys Lys Met Met Leu Asp Asn His
                        340                 345                 350

Ala Leu Tyr Asp Lys Thr Lys Lys Ile Phe Leu Asn Ala Ala Ser Glu
                        355                 360                 365

Glu Glu Ile Phe Ala His Leu Gly Leu Asp Tyr Leu Glu Pro Trp Glu
                        370                 375                 380

Arg Asn Ala
        385

<210> SEQ ID NO 9
<211> LENGTH: 381
<212> TYPE: PRT
<213> ORGANISM: ARTIFICIAL SEQUENCE
<220> FEATURE:
<223> OTHER INFORMATION: truncated dog

<400> SEQUENCE: 9

Asp Tyr Thr Ala Ser Pro Asn Pro Glu Leu Gln Lys Thr Leu Pro Val
        1               5                   10                  15

Ala Val Lys Lys Ile Ser Gln Tyr Ala Cys Gln Arg Arg Thr Thr Leu
                        20                  25                  30

Asn Asn Tyr Asn Asn Val Phe Thr Asp Ala Phe Glu Val Leu Ala Glu
                        35                  40                  45

Asn Tyr Glu Phe Arg Glu Asn Glu Val Phe Ser Leu Thr Phe Met Arg
                        50                  55                  60

Ala Ala Ser Val Leu Lys Ser Leu Pro Phe Thr Ile Ile Ser Met Lys
        65                  70                  75                  80

Asp Thr Glu Gly Ile Pro Cys Leu Gly Asp Gln Val Lys Cys Ile Ile
                        85                  90                  95

Glu Glu Ile Ile Glu Asp Gly Glu Ser Ser Glu Val Lys Ala Val Leu
                        100                 105                 110

Asn Asp Glu Arg Tyr Gln Ser Phe Lys Leu Phe Thr Ser Val Phe Gly
```

```
            115                 120                 125
Val Gly Leu Lys Thr Ser Glu Lys Trp Phe Arg Met Gly Phe Arg Thr
130                 135                 140

Leu Ser Lys Ile Lys Ser Asp Lys Ser Leu Lys Phe Thr Pro Met Gln
145                 150                 155                 160

Lys Ala Gly Phe Leu Tyr Tyr Glu Asp Leu Val Ser Cys Val Thr Arg
                165                 170                 175

Ala Glu Ala Glu Ala Val Gly Val Leu Val Lys Glu Ala Val Gly Ala
                180                 185                 190

Phe Leu Pro Asp Ala Phe Val Thr Met Thr Gly Gly Phe Arg Arg Gly
            195                 200                 205

Lys Lys Met Gly His Asp Val Asp Phe Leu Ile Thr Ser Pro Gly Ser
210                 215                 220

Thr Asp Glu Asp Glu Gln Leu Leu Pro Lys Val Ile Asn Leu Trp
225                 230                 235                 240

Glu Arg Lys Gly Leu Leu Leu Tyr Cys Asp Leu Val Glu Ser Thr Phe
                245                 250                 255

Glu Lys Leu Lys Leu Pro Ser Arg Lys Val Asp Ala Leu Asp His Phe
            260                 265                 270

Gln Lys Cys Phe Leu Ile Leu Lys Leu His His Gln Arg Val Asp Gly
            275                 280                 285

Gly Lys Cys Ser Gln Gln Glu Gly Lys Thr Trp Lys Ala Ile Arg Val
            290                 295                 300

Asp Leu Val Met Cys Pro Tyr Glu Arg Arg Ala Phe Ala Leu Leu Gly
305                 310                 315                 320

Trp Thr Gly Ser Arg Gln Phe Glu Arg Asp Leu Arg Arg Tyr Ala Ser
                325                 330                 335

His Glu Arg Lys Met Ile Leu Asp Asn His Ala Leu Tyr Asp Lys Thr
            340                 345                 350

Lys Lys Ile Phe Leu Lys Ala Glu Ser Glu Glu Ile Phe Ala His
            355                 360                 365

Leu Gly Leu Asp Tyr Ile Glu Pro Trp Glu Arg Asn Ala
370                 375                 380

<210> SEQ ID NO 10
<211> LENGTH: 382
<212> TYPE: PRT
<213> ORGANISM: ARTIFICIAL SEQUENCE
<220> FEATURE:
<223> OTHER INFORMATION: TRUNC MOLE

<400> SEQUENCE: 10

Gly Asp Cys Pro Ala Ser His Asp Ser Ser Pro Gln Lys Thr Glu Ser
1               5                   10                  15

Ala Ala Val Gln Lys Ile Ser Gln Tyr Ala Cys Gln Arg Arg Thr Thr
                20                  25                  30

Leu Asn Asn His Asn His Ile Phe Thr Asp Ala Phe Glu Ile Leu Ala
            35                  40                  45

Glu Asn Cys Glu Phe Arg Glu Asn Glu Gly Ser Tyr Val Thr Tyr Met
50                  55                  60

Arg Ala Ala Ser Val Leu Lys Ser Leu Pro Phe Ser Ile Ile Ser Met
65                  70                  75                  80

Lys Asp Thr Glu Gly Ile Pro Cys Leu Ala Asp Lys Val Lys Cys Val
                85                  90                  95

Ile Glu Glu Ile Ile Glu Asp Gly Glu Ser Ser Glu Val Lys Ala Val
```

```
            100                 105                 110
Leu Asn Asp Glu Arg Tyr Lys Ser Phe Lys Leu Phe Thr Ser Val Phe
            115                 120                 125

Gly Val Gly Leu Lys Thr Ala Glu Lys Trp Phe Arg Leu Gly Phe Arg
            130                 135                 140

Thr Leu Ser Gly Ile Met Asn Asp Lys Thr Leu Lys Leu Thr His Met
145                 150                 155                 160

Gln Lys Ala Gly Phe Leu Tyr Tyr Glu Asp Leu Val Ser Cys Val Thr
                    165                 170                 175

Arg Ala Glu Ala Glu Ala Val Gly Val Leu Lys Glu Ala Val Trp
                    180                 185                 190

Ala Phe Leu Pro Asp Ala Ile Val Thr Met Thr Gly Gly Phe Arg Arg
            195                 200                 205

Gly Lys Lys Val Gly His Asp Val Asp Phe Leu Ile Thr Ser Pro Glu
            210                 215                 220

Ala Thr Glu Glu Gln Glu Gln Gln Leu Leu His Lys Val Ile Thr Phe
225                 230                 235                 240

Trp Glu Lys Glu Gly Leu Leu Leu Tyr Cys Asp Leu Tyr Glu Ser Thr
                    245                 250                 255

Phe Glu Lys Leu Lys Met Pro Ser Arg Lys Val Asp Ala Leu Asp His
                    260                 265                 270

Phe Gln Lys Cys Phe Leu Ile Leu Lys Leu His Arg Glu Cys Val Asp
                    275                 280                 285

Asp Gly Thr Ser Ser Gln Leu Gln Gly Lys Thr Trp Lys Ala Ile Arg
            290                 295                 300

Val Asp Leu Val Val Cys Pro Tyr Glu Cys Arg Ala Phe Ala Leu Leu
305                 310                 315                 320

Gly Trp Thr Gly Ser Pro Gln Phe Glu Arg Asp Leu Arg Arg Tyr Ala
                    325                 330                 335

Thr His Glu Arg Lys Met Met Leu Asp Asn His Ala Leu Tyr Asp Lys
                    340                 345                 350

Thr Lys Arg Lys Phe Leu Ser Ala Asp Ser Glu Glu Asp Ile Phe Ala
                    355                 360                 365

His Leu Gly Leu Asp Tyr Ile Glu Pro Trp Glu Arg Asn Ala
            370                 375                 380

<210> SEQ ID NO 11
<211> LENGTH: 379
<212> TYPE: PRT
<213> ORGANISM: ARTIFICIAL SEQUENCE
<220> FEATURE:
<223> OTHER INFORMATION: Pika trunk

<400> SEQUENCE: 11

Glu Tyr Ser Ala Asn Pro Ser Pro Gly Pro Gln Ala Thr Pro Ala Val
1               5                   10                  15

Tyr Lys Ile Ser Gln Tyr Ala Cys Gln Arg Arg Thr Thr Leu Asn Asn
                20                  25                  30

His Asn His Ile Phe Thr Asp Ala Phe Glu Ile Leu Ala Glu Asn Tyr
            35                  40                  45

Glu Phe Lys Glu Asn Glu Gly Cys Tyr Val Thr Tyr Met Arg Ala Ala
        50                  55                  60

Ser Val Leu Lys Ser Leu Pro Phe Thr Ile Val Ser Met Lys Asp Thr
65                  70                  75                  80

Glu Gly Ile Pro Cys Leu Glu Asp Lys Val Lys Ser Ile Met Glu Glu
```

```
                    85                  90                  95
Ile Ile Glu Glu Gly Glu Ser Ser Glu Val Lys Ala Val Leu Ser Asp
            100                 105                 110

Glu Arg Tyr Gln Cys Phe Lys Leu Phe Thr Ser Val Phe Gly Val Gly
            115                 120                 125

Leu Lys Thr Ser Glu Lys Trp Phe Arg Met Gly Phe Arg Ser Leu Ser
    130                 135                 140

Asn Ile Arg Leu Asp Lys Ser Leu Lys Phe Thr Gln Met Gln Lys Ala
145                 150                 155                 160

Gly Phe Arg Tyr Tyr Glu Asp Ile Val Ser Cys Val Thr Arg Ala Glu
                165                 170                 175

Ala Glu Ala Val Asp Val Leu Val Asn Glu Ala Val Arg Ala Phe Leu
            180                 185                 190

Pro Asp Ala Phe Ile Thr Met Thr Gly Gly Phe Arg Arg Gly Lys Lys
        195                 200                 205

Ile Gly His Asp Val Asp Phe Leu Ile Thr Ser Pro Glu Leu Thr Glu
    210                 215                 220

Glu Asp Glu Gln Gln Leu Leu His Lys Val Met Asn Leu Trp Glu Lys
225                 230                 235                 240

Lys Gly Leu Leu Leu Tyr His Asp Leu Val Glu Ser Thr Phe Glu Lys
                245                 250                 255

Leu Lys Gln Pro Ser Arg Lys Val Asp Ala Leu Asp His Phe Gln Lys
            260                 265                 270

Cys Phe Leu Ile Phe Lys Leu Tyr His Glu Arg Val Gly Gly Asp Arg
        275                 280                 285

Cys Arg Gln Pro Glu Gly Lys Asp Trp Lys Ala Ile Arg Val Asp Leu
    290                 295                 300

Val Met Cys Pro Tyr Glu Cys His Ala Phe Ala Leu Leu Gly Trp Thr
305                 310                 315                 320

Gly Ser Arg Gln Phe Glu Arg Asp Leu Arg Arg Tyr Ala Ser His Glu
                325                 330                 335

Arg Lys Met Ile Leu Asp Asn His Ala Leu Tyr Asp Lys Thr Lys Arg
            340                 345                 350

Val Phe Leu Gln Ala Glu Asn Glu Glu Ile Phe Ala His Leu Gly
        355                 360                 365

Leu Asp Tyr Ile Glu Pro Trp Glu Arg Asn Ala
    370                 375

<210> SEQ ID NO 12
<211> LENGTH: 384
<212> TYPE: PRT
<213> ORGANISM: ARTIFICIAL SEQUENCE
<220> FEATURE:
<223> OTHER INFORMATION: TRUNC HEDGEHOG

<400> SEQUENCE: 12

Asp Ala Ser Phe Gly Ser Asn Pro Gly Ser Gln Asn Thr Pro Pro Leu
1               5                   10                  15

Ala Ile Lys Lys Ile Ser Gln Tyr Ala Cys Gln Arg Arg Thr Ser Leu
            20                  25                  30

Asn Asn Cys Asn His Ile Phe Thr Asp Ala Leu Asp Ile Leu Ala Glu
        35                  40                  45

Asn His Glu Phe Arg Glu Asn Glu Val Ser Cys Val Ala Phe Met Arg
    50                  55                  60

Ala Ala Ser Val Leu Lys Ser Leu Pro Phe Thr Ile Ile Ser Met Lys
```

```
                65                  70                  75                  80
Asp Thr Lys Gly Ile Pro Cys Leu Gly Asp Lys Ala Lys Cys Val Ile
                    85                  90                  95
Glu Glu Ile Ile Glu Asp Gly Glu Ser Ser Glu Val Lys Ala Ile Leu
                100                 105                 110
Asn Asp Glu Arg Tyr Gln Ser Phe Lys Leu Phe Thr Ser Val Phe Gly
                115                 120                 125
Val Gly Leu Lys Thr Ser Glu Lys Trp Phe Arg Met Gly Phe Arg Thr
130                 135                 140
Leu Asn Lys Ile Met Ser Asp Lys Thr Leu Lys Leu Thr Arg Met Gln
145                 150                 155                 160
Lys Ala Gly Phe Leu Tyr Tyr Glu Asp Leu Val Ser Cys Val Ala Lys
                165                 170                 175
Ala Glu Ala Asp Ala Val Ser Val Leu Val Gln Glu Ala Val Trp Ala
                180                 185                 190
Phe Leu Pro Asp Ala Met Val Thr Met Thr Gly Gly Phe Arg Arg Gly
                195                 200                 205
Lys Lys Leu Gly His Asp Val Asp Phe Leu Ile Thr Ser Pro Gly Ala
210                 215                 220
Thr Glu Glu Glu Glu Gln Gln Leu Leu Pro Lys Val Ile Asn Phe Trp
225                 230                 235                 240
Glu Arg Lys Gly Leu Leu Leu Tyr His Asp Leu Val Glu Ser Thr Phe
                245                 250                 255
Glu Lys Leu Lys Leu Pro Ser Arg Lys Val Asp Ala Leu Asp His Phe
                260                 265                 270
Gln Lys Cys Phe Leu Ile Leu Lys Leu His Leu Gln His Val Asn Gly
                275                 280                 285
Val Gly Asn Ser Lys Thr Gly Gln Gln Glu Gly Lys Asn Trp Lys Ala
                290                 295                 300
Ile Arg Val Asp Leu Val Met Cys Pro Tyr Glu Arg Arg Ala Phe Ala
305                 310                 315                 320
Leu Leu Gly Trp Thr Gly Ser Arg Gln Phe Glu Arg Asp Leu Arg Arg
                325                 330                 335
Phe Ala Thr His Glu Arg Lys Met Met Leu Asp Asn His Ala Leu Tyr
                340                 345                 350
Asp Lys Thr Lys Arg Ile Phe Leu Lys Ala Glu Ser Glu Glu Glu Ile
                355                 360                 365
Phe Ala His Leu Gly Leu Asp Tyr Ile Asp Pro Trp Glu Arg Asn Ala
                370                 375                 380

<210> SEQ ID NO 13
<211> LENGTH: 381
<212> TYPE: PRT
<213> ORGANISM: ARTIFICIAL SEQUENCE
<220> FEATURE:
<223> OTHER INFORMATION: truncated tree shrew

<400> SEQUENCE: 13

Asp His Ser Thr Ser Pro Ser Pro Gly Pro Gln Lys Thr Pro Ala Leu
1               5                   10                  15
Ala Val Gln Lys Ile Ser Gln Tyr Ala Cys Gln Arg Arg Thr Thr Leu
                20                  25                  30
Asn Asn Cys Asn Arg Val Phe Thr Asp Ala Phe Glu Thr Leu Ala Glu
                35                  40                  45
Asn Tyr Glu Phe Arg Glu Asn Glu Asp Ser Ser Val Ile Phe Leu Arg
```

```
                50                  55                  60
Ala Ala Ser Val Leu Arg Ser Leu Pro Phe Thr Ile Thr Ser Met Arg
 65                  70                  75                  80

Asp Thr Glu Gly Leu Pro Cys Leu Gly Asp Lys Val Lys Cys Val Ile
                 85                  90                  95

Glu Glu Ile Ile Glu Asp Gly Glu Ser Ser Glu Val Asn Ala Val Leu
                100                 105                 110

Asn Asp Glu Arg Tyr Lys Ser Phe Lys Leu Phe Thr Ser Val Phe Gly
                115                 120                 125

Val Gly Leu Lys Thr Ser Glu Lys Trp Phe Arg Met Gly Phe Arg Thr
            130                 135                 140

Leu Ser Arg Val Arg Ser Asp Lys Ser Leu His Leu Thr Arg Met Gln
145                 150                 155                 160

Gln Ala Gly Phe Leu Tyr Tyr Glu Asp Leu Ala Ser Cys Val Thr Arg
                165                 170                 175

Ala Glu Ala Glu Ala Val Gly Val Leu Val Lys Glu Ala Val Gly Ala
                180                 185                 190

Phe Leu Pro Asp Ala Leu Val Thr Ile Thr Gly Gly Phe Arg Arg Gly
                195                 200                 205

Lys Lys Thr Gly His Asp Val Asp Phe Leu Ile Thr Ser Pro Gly Ser
            210                 215                 220

Thr Glu Glu Lys Glu Glu Glu Leu Leu Gln Lys Val Leu Asn Leu Trp
225                 230                 235                 240

Glu Lys Lys Gly Leu Leu Leu Tyr Tyr Asp Leu Val Glu Ser Thr Phe
                245                 250                 255

Glu Lys Leu Lys Thr Pro Ser Arg Lys Val Asp Ala Leu Asp His Phe
                260                 265                 270

Pro Lys Cys Phe Leu Ile Leu Lys Leu His His Gln Arg Val Asp Gly
                275                 280                 285

Asp Lys Pro Ser Gln Gln Glu Gly Lys Ser Trp Lys Ala Ile Arg Val
            290                 295                 300

Asp Leu Val Met Cys Pro Tyr Glu Arg His Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Lys Thr
                340                 345                 350

Lys Arg Val Phe Leu Lys Ala Glu Ser Glu Glu Asp Ile Phe Ala His
                355                 360                 365

Leu Gly Leu Asp Tyr Ile Glu Pro Trp Glu Arg Asn Ala
            370                 375                 380

<210> SEQ ID NO 14
<211> LENGTH: 394
<212> TYPE: PRT
<213> ORGANISM: ARTIFICIAL SEQUENCE
<220> FEATURE:
<223> OTHER INFORMATION: TRUNCATED PLATYPUS

<400> SEQUENCE: 14

Leu Thr Asn Ser Ala Pro Ile Asn Cys Met Thr Glu Thr Pro Ser Leu
 1               5                  10                  15

Ala Thr Lys Gln Val Ser Gln Tyr Ala Cys Glu Arg Arg Thr Thr Leu
                20                  25                  30

Asn Asn Cys Asn Gln Lys Phe Thr Asp Ala Phe Glu Ile Leu Ala Lys
```

```
                    35                  40                  45
Asp Phe Glu Phe Arg Glu Asn Glu Gly Ile Cys Leu Ala Phe Met Arg
 50                  55                  60

Ala Ile Ser Val Leu Lys Cys Leu Pro Phe Thr Ile Val Arg Met Lys
 65                  70                  75                  80

Asp Ile Glu Gly Val Pro Trp Leu Gly Asp Gln Val Lys Ser Ile Ile
                     85                  90                  95

Glu Glu Ile Ile Glu Asp Gly Ser Ser Val Lys Ala Val Leu
                100                 105                 110

Asn Asp Glu Arg Tyr Arg Ser Phe Gln Leu Phe Asn Ser Val Phe Glu
                115                 120                 125

Val Gly Leu Thr Asp Asn Gly Glu Asn Gly Ile Ala Arg Gly Phe Gln
                130                 135                 140

Thr Leu Asn Glu Val Ile Thr Asp Glu Asn Ile Ser Leu Thr Lys Thr
145                 150                 155                 160

Thr Leu Ser Thr Ser Leu Trp Asn Tyr Leu Pro Gly Phe Leu Tyr Tyr
                165                 170                 175

Glu Asp Leu Val Ser Cys Val Ala Lys Glu Glu Ala Asp Ala Val Tyr
                180                 185                 190

Leu Ile Val Lys Glu Ala Val Arg Ala Phe Leu Pro Glu Ala Leu Val
                195                 200                 205

Thr Leu Thr Gly Gly Phe Arg Arg Gly Lys Lys Ile Gly His Asp Val
210                 215                 220

Asp Phe Leu Ile Ser Asp Pro Glu Ser Gly Gln Asp Glu Gln Leu Leu
225                 230                 235                 240

Pro Asn Ile Ile Lys Leu Trp Glu Lys Gln Glu Leu Leu Tyr Tyr
                245                 250                 255

Asp Leu Val Glu Ser Thr Phe Glu Lys Thr Lys Ile Pro Ser Arg Lys
                260                 265                 270

Val Asp Ala Met Asp His Phe Gln Lys Cys Phe Leu Ile Leu Lys Leu
                275                 280                 285

His His Gln Lys Val Asp Ser Gly Arg Tyr Lys Pro Pro Glu Ser
                290                 295                 300

Lys Asn His Glu Ala Lys Asn Trp Lys Ala Ile Arg Val Asp Leu Val
305                 310                 315                 320

Met Cys Pro Phe Glu Gln Tyr Ala Tyr Ala Leu Leu Gly Trp Thr Gly
                325                 330                 335

Ser Arg Gln Phe Glu Arg Asp Leu Arg Arg Tyr Ala Thr His Glu Lys
                340                 345                 350

Lys Met Met Leu Asp Asn His Ala Leu Tyr Asp Lys Thr Lys Lys Ile
                355                 360                 365

Phe Leu Lys Ala Glu Ser Glu Asp Ile Phe Thr His Leu Gly Leu
                370                 375                 380

Asp Tyr Ile Glu Pro Trp Glu Arg Asn Ala
385                 390

<210> SEQ ID NO 15
<211> LENGTH: 384
<212> TYPE: PRT
<213> ORGANISM: ARTIFICIAL SEQUENCE
<220> FEATURE:
<223> OTHER INFORMATION: TRUNCATED JERBOA

<400> SEQUENCE: 15

Ser Ser Glu Leu Glu Leu Leu Asp Val Ser Trp Leu Ile Glu Cys Met
```

```
            1               5                  10                 15
        Gly Ala Gly Lys Pro Val Glu Met Thr Gly Arg His Gln Leu Val Lys
                        20                  25                  30
        Gln Thr Phe Cys Leu Pro Gly Phe Ile Leu Gln Asp Ala Phe Asp Ile
                        35                  40                  45
        Leu Ala Glu Asn Cys Glu Phe Arg Glu Asn Glu Ala Ser Cys Val Glu
        50                  55                  60
        Phe Met Arg Ala Ala Ser Val Leu Lys Ser Leu Pro Phe Pro Ile Ile
        65                  70                  75                  80
        Ser Val Lys Asp Thr Glu Gly Ile Pro Trp Leu Gly Lys Val Lys
                        85                  90                  95
        Cys Val Ile Glu Glu Ile Ile Glu Asp Gly Glu Ser Ser Glu Val Lys
                        100                 105                 110
        Ala Leu Leu Asn Asp Glu Arg Tyr Lys Ser Phe Lys Leu Phe Thr Ser
                        115                 120                 125
        Val Phe Gly Val Gly Leu Lys Thr Ala Glu Arg Trp Phe Arg Met Gly
                        130                 135                 140
        Phe Arg Thr Leu Ser Thr Val Lys Leu Asp Lys Ser Leu Thr Phe Thr
        145                 150                 155                 160
        Arg Met Gln Lys Ala Gly Phe Leu His Tyr Glu Asp Leu Val Ser Cys
                        165                 170                 175
        Val Thr Arg Ala Glu Ala Glu Ala Val Ser Val Leu Val Gln Gln Ala
                        180                 185                 190
        Val Val Ala Phe Leu Pro Asp Ala Leu Val Ser Met Thr Gly Gly Phe
                        195                 200                 205
        Arg Arg Gly Lys Lys Ile Gly His Asp Val Asp Phe Leu Ile Thr Ser
                        210                 215                 220
        Pro Glu Ala Thr Glu Glu Glu Gln Gln Leu Leu His Lys Val Thr
        225                 230                 235                 240
        Asn Phe Trp Glu Gln Lys Gly Leu Leu Leu Tyr Cys Asp His Val Glu
                        245                 250                 255
        Ser Thr Phe Glu Lys Cys Lys Leu Pro Ser Arg Lys Val Asp Ala Leu
                        260                 265                 270
        Asp His Phe Gln Lys Cys Phe Leu Ile Leu Lys Leu Tyr Arg Glu Arg
                        275                 280                 285
        Val Asp Ser Val Lys Ser Ser Gln Gln Glu Gly Lys Gly Trp Lys Ala
                        290                 295                 300
        Ile Arg Val Asp Leu Val Met Cys Pro Tyr Glu Cys Arg Ala Phe Ala
        305                 310                 315                 320
        Leu Leu Gly Trp Thr Gly Ser Arg Gln Phe Glu Arg Asp Leu Arg Arg
                        325                 330                 335
        Tyr Ala Thr His Glu Arg Lys Met Arg Leu Asp Asn His Ala Leu Tyr
                        340                 345                 350
        Asp Lys Thr Lys Arg Val Phe Leu Lys Ala Glu Ser Glu Glu Glu Ile
                        355                 360                 365
        Phe Ala His Leu Gly Leu Glu Tyr Ile Glu Pro Leu Glu Arg Asn Ala
                        370                 375                 380
```

<210> SEQ ID NO 16
<211> LENGTH: 32
<212> TYPE: DNA
<213> ORGANISM: ARTIFICIAL SEQUENCE
<220> FEATURE:
<223> OTHER INFORMATION: Exemplary cDNA produced in a method of the invention (Fig. 1B)

```
<220> FEATURE:
<221> NAME/KEY: misc_feature
<222> LOCATION: (8)..(32)
<223> OTHER INFORMATION: n is a, c, g, t or u

<400> SEQUENCE: 16
tttttttnnn nnnnnnnnnn nnnnnnnnnn nn                                32

<210> SEQ ID NO 17
<211> LENGTH: 15
<212> TYPE: DNA
<213> ORGANISM: ARTIFICIAL SEQUENCE
<220> FEATURE:
<223> OTHER INFORMATION: Exemplary cDNA produced in process of Fig. 4A
<220> FEATURE:
<221> NAME/KEY: misc_feature
<222> LOCATION: (15)..(15)
<223> OTHER INFORMATION: n is a, c, g, t or u

<400> SEQUENCE: 17 ttttttttt ttttn                                                    15

<210> SEQ ID NO 18
<211> LENGTH: 13
<212> TYPE: DNA
<213> ORGANISM: ARTIFICIAL SEQUENCE
<220> FEATURE:
<223> OTHER INFORMATION: Antibody barcode
<220> FEATURE:
<221> NAME/KEY: misc_feature
<222> LOCATION: (8)..(13)
<223> OTHER INFORMATION: n is a, c, g, t or u

<400> SEQUENCE: 18
aaaaaaannn nnn                                                     13
```

METHODS FOR EXTENDING POLYNUCLEOTIDES

RELATED APPLICATIONS

The present application is a continuation application of U.S. application Ser. No. 16/970,590, entitled "DIRECT OLIGONUCLEOTIDE SYNTHESIS ON CELLS AND BIOMOLECULES," filed on Aug. 17, 2020, which is a U.S. National Stage Entry of International Application No. PCT/EP2019/084347, entitled "DIRECT OLIGONUCLEOTIDE SYNTHESIS ON CELLS AND BIOMOLECULES," filed on Dec. 10, 2019, which claims priority to European Application No. 19305219.8 filed on Feb. 25, 2019 and European Application No. 18306687.7 filed on Dec. 13, 2018. All above-identified applications are hereby incorporated by reference in their entireties.

There are many instances in the biological and medical sciences where large-scale analysis of biomolecules or cells can be facilitated by the use of nucleic acid tags, or barcodes, e.g. Brenner et al, Proc. Natl. Acad. Sci., 97: 1665-1670 (2000); Brenner et al, U.S. Pat. No. 7,537,897; Brenner et al, U.S. Pat. No. 8,476,018; McCloskey et al, U.S. patent publication 2007/0020640; Kinde et al, Proc. Natl. Acad. Sci., 108: 9530-9535 (2011); Fu et al, Proc. Natl. Acad. Sci., 108: 9026-9031 (2011); Nolan, U.S. patent publication 2016/0251697; Zheng et al, Nature Comm., 8:14049 (2017). Typically such oligonucleotide labels are attached either (1) by "labeling by sampling" (also referred to as, "stochastic labeling"), where a large set of oligonucleotide labels are pre-synthesized and used to form conjugates with a much smaller population of target organisms or biomolecules to give a conjugate population of organisms or biomolecules with unique labels e.g., Brenner et al, U.S. Pat. No. 7,537,897; or Fu et al, Proc. Natl. Acad. Sci. (cited above); or (2) by "split and mix" hybridizations of a plurality of pre-synthesized oligonucleotide subunits to give a population of organisms or biomolecules all of which have substantially unique labels, e.g. Nolan (cited above); or Seelig et al, U.S. patent publication 2016/0138086. Pre-synthesized tags or tag subunits have been used in these processes because oligonucleotide synthesis has been dominated by chemical methods, such as phosphoramidite chemistry, which requires harsh non-aqueous conditions that are incompatible with biological organisms and biomolecules.

It would be highly desirable if a capability were available for direct oligonucleotide synthesis on biological organisms or biomolecules to provide such organisms or biomolecules with oligonucleotide labels, such as unique and durable barcodes or tags, for tracking and sorting. Such labeling, particularly when coupled with next-generation sequencing techniques, would be a valuable tool for large-scale cell-based analysis of a host of biological processes.

SUMMARY OF THE INVENTION

The invention is directed to methods for synthesizing oligonucleotides directly on biomolecules and biological cells, including the application of such methods for single-cell analysis, such as single-cell transcriptome analysis.

In some embodiments the invention is directed to methods of synthesizing oligonucleotides on biological cells or biomolecules comprising the steps of: (a) providing biological cells or biomolecule having an initiator with a free 3'-hydroxyl; (b) repeating for a plurality of cycles the steps of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, thereby synthesizing on the biological cells or biomolecules a oligonucleotide of predetermined sequence. In some embodiments, such steps are carried out under conditions that maintain biological cells, especially mammalian cells, in a viable state. In some embodiments, the step of deblocking is carried out enzymatically under conditions that maintain biological cells, especially mammalian cells, in a viable state.

In some embodiments, the invention is directed to a method of generating a cell-specific cDNA library with cell-specific oligonucleotide barcodes comprising the steps of: (a) synthesizing a unique oligonucleotide barcode on a cell surface membrane of each cell in a population of cells to form a population of barcoded cells; (b) isolating each barcoded cell in a reactor; (c) lysing barcoded cells in each reactor; (d) performing reverse-transcriptase polymerase chain reaction (RT-PCR) in each reactor to produce a cDNA library with cell-specific oligonucleotide barcodes. In some embodiments, the step of synthesizing is carried out by a template-free enzymatic synthesis method of the invention. In some embodiments, the RT-PCR reaction includes attaching barcodes to cDNAs by a polymerase cycling amplification reaction.

In some embodiments, the invention is directed to methods of generating cell-specific cDNA libraries each with cell-specific oligonucleotide barcodes comprising the steps of: (a) capturing mRNA of a single cell by hybridizing the mRNA to capture oligonucleotides attached to a bead, wherein the capture oligonucleotides are complementary to segments of the mRNA and wherein the capture oligonucleotides are attached to the bead by 5-ends and have free 3'-hydroxyls; (b) extending 3'-ends of the capture oligonucleotides with a reverse transcriptase using the captured mRNAs as templates to form cell-specific cDNA libraries; (c) synthesizing a unique cell-specific oligonucleotide barcode on each cDNA of a bead by template-free enzymatic synthesis. In some embodiments, the unique cell- or bead-specific barcode is a random sequence oligonucleotide and the step of synthesizing such barcode is carried out by a "split and mix" procedure with template-free enzymatic synthesis.

In some embodiments, the invention is directed to methods of extending one or more native polynucleotides with a predetermined nucleotide sequence, comprising: providing one or more native polynucleotides in a reaction mixture under TdT reaction conditions, the native polynucleotides having free 3'-hydroxyls; and extending the one or more native polynucleotide with a predetermined sequence of nucleotides by repeated cycles of the steps (i) contacting the native polynucleotides or elongated native polynucleotides having free 3'-O-hydroxyls with a 3'-O-blocked nucleoside triphosphate and a TdT variant so that the native polynucleotides or elongated native polynucleotides are elongated by incorporation of a 3'-O-blocked nucleoside triphosphate to form 3'-O-blocked elongated native polynucleotides, and (ii) deblocking the elongated native polynucleotides to form elongated native polynucleotides having free 3'-hydroxyls, thereby synthesizing on the native polynucleotides a oligonucleotide of the predetermined sequence.

These above-characterized aspects, as well as other aspects, of the present invention are exemplified in a number of illustrated implementations and applications, some of

DETAILED DESCRIPTION OF THE INVENTION

Figure 1A:
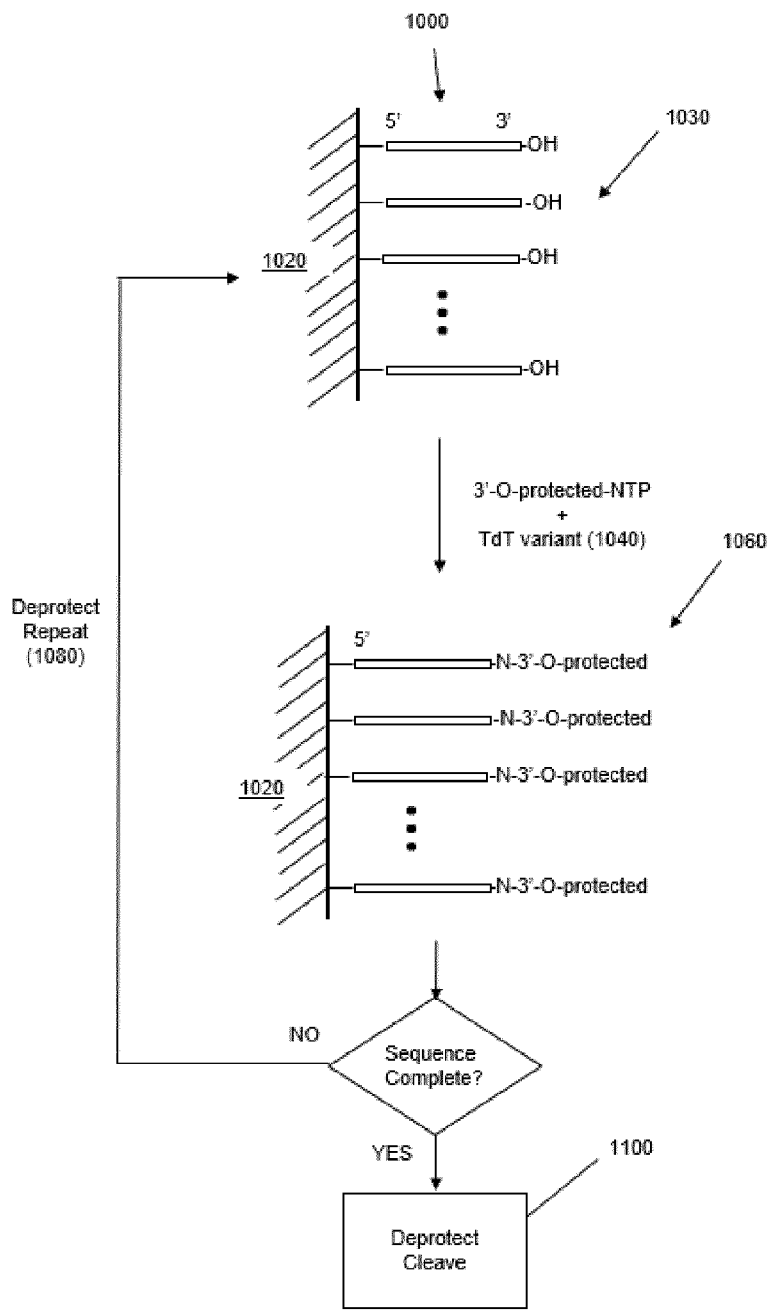
FIG. 1A illustrates diagrammatically the steps of a method of template-free enzymatic nucleic acid synthesis using a TdT.

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention.

The practice of the present invention may employ, unless otherwise indicated, conventional techniques and descriptions of organic chemistry, molecular biology (including recombinant techniques), cell biology, and biochemistry, which are within the skill of the art. Such conventional techniques may include, but are not limited to, preparation and use of synthetic peptides, synthetic polynucleotides, monoclonal antibodies, nucleic acid cloning, amplification, sequencing and analysis, and related techniques. Protocols for such conventional techniques can be found in product literature from manufacturers and in standard laboratory manuals, such as Genome Analysis: A Laboratory Manual Series (Vols. I-IV); PCR Primer: A Laboratory Manual; and Molecular Cloning: A Laboratory Manual (all from Cold Spring Harbor Laboratory Press); Lutz and Bornscheuer, Editors, Protein Engineering Handbook (Wiley-VCH, 2009); Hermanson, Bioconjugate Techniques, Second Edition (Academic Press, 2008); and like references.

The invention is directed to methods for directly synthesizing oligonucleotides on cells or biomolecules using template-free enzymatic oligonucleotide synthesis techniques. Such techniques can be applied directly to biomolecules extracted from their natural settings (e.g. DNAs or RNAs), to biomolecules (e.g. proteins) modified by the attachment of an initiator, or to biomolecules (e.g. nucleic acids, polysaccharides, polypeptides, etc.) produced synthetically. Such techniques may be applied in any circumstances where the mild conditions of an enzymatic reaction are necessary or useful. In particular, the template-free enzymatic synthesis techniques may be employed in hybrid chemical-enzymatic polynucleotide synthesis wherein a precursor polynucleotide is synthesized chemically, then the precursor is further modified by additions of components enzymatically, such as labeled nucleotides, that may be altered in, or not survive, the harsh conditions of chemical synthesis. Such hybrid synthesis methods may include several alterations between chemical additions and enzymatic additions of nucleotides or analogs thereof. Such hybrid synthesis techniques may pair enzymatic synthesis with a variety of different chemical synthesis approaches including, but not limited to, phosphoramidite, phosphodiester, phosphotriester, phosphite triester, H-phosphonate chemistries, e.g. Narang, Editor, Synthesis and applications of DNA and RNA (Academic Press, Inc., 1987).

In some embodiments, template-free enzymatic synthesis techniques require the presence of an initiator oligonucleotide having a free 3'-hydroxyl which may be part of a biomolecule, in the case of polynucleotides of cDNAs, or it may be readily added by a variety of chemical techniques, e.g. using readily available click chemistry reactions, in the case of cellular membrane proteins, antibodies, or the like. With the availability of an initiator, enzymatic oligonucleotide synthesis may be implemented by repeated cycles of (i) extension of the initiator (or previously extended strand) having a free 3'-hydroxyl by a single nucleotide using a template-free polymerase, such as a terminal deoxynucleotidyl transferase (TdT), in the presence of a 3'-O-blocked nucleoside triphosphate, and (ii) de-blocking recently incorporated 3'-O-blocked nucleotides to regenerate new extendable 3'-hydroxyls. Cycles are continued until an oligonucleotide having a desired sequence is synthesized. In some embodiments, unique oligonucleotide barcodes may be synthesized directly on biological cells, such as mammalian cells, of a population by a "split and mix" synthesis strategy. In some embodiments, capping steps may be included in which non-extended free hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exonuclease activity, e.g. Exo I, as described by Jensen et al, Biochemistry, 57: 1821-1832 (2018).

In some embodiments, the invention is directed to methods of synthesizing oligonucleotides on biological cells or biomolecules comprising the steps of (a) providing biological cells or biomolecule having an initiator with a free 3'-hydroxyl; (b) repeating for a plurality of cycles the steps of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, thereby synthesizing on the biological cells or biomolecules a oligonucleotide of predetermined sequence. In some embodiments, the biological cells are provided and deblocking is carried out enzymatically. In some embodiments, the 3'-O-blocked nucleoside triphosphate is a 3'-phosphate-nucleoside triphosphate and the step of deblocking is carried out by treating said 3'-O-blocked elongated fragments with a 3'-phosphatase activity. In some embodiments, the 3'-phophatase activity is provided by T4 polynucleotide kinase, recombinant shrimp alkaline phosphatase, or a calf intestinal alkaline phosphatase. In some embodiments, the 3'-O-blocked nucleoside triphosphate is a 3'-ester-nucleoside triphosphate and the step of deblocking is carried out by treating said 3'-O-blocked elongated fragments with an esterase activity. In some embodiments, the esterase activity is a lipase activity, such as, a proteinase K activity. In some embodiments, the 3'-O-blocked nucleoside triphosphate is a 3'-acetyl-nucleoside triphosphate and the step of deblocking is carried out by treating said 3'-O-blocked elongated fragments with an acetylesterase activity. In some embodiments, the template-independent DNA polymerase is a terminal deoxynucleotidyl transferase (TdT) variant having an amino acid sequence at least sixty percent identical to any one of the amino acid sequences of SEQ ID NOs 2-15 with substitutions at a first arginine at position 207 of SEQ ID NO: 2 or a functionally equivalent position in the amino acid sequences of SEQ ID NOs 3-15 and at a second arginine at 325 of SEQ ID NO: 2 or a functionally equivalent position in the amino acid sequences of SEQ ID NOs 3-15, wherein the variant TdT (i) is capable of synthesizing a nucleic acid fragment without a template and (ii) is capable of incorporating a 3'-O-modified nucleotide onto a free 3'-hydroxyl of a nucleic acid fragment.

In some embodiments, methods of the invention for synthesizing oligonucleotides on a viable cell may be carried out with the following steps: (a) providing an initiator with a free 3'-hydroxyl attached to a cell surface molecule of the cell or anchored in the cell surface membrane of the cell; (b) repeating under biological conditions for a plurality of cycles the steps of (i) contacting the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) enzymatically deblocking the elongated fragments to form elongated fragments having free 3'-hydroxyls, thereby synthesizing the oligonucleotide of predetermined sequence.

Figure 1B:
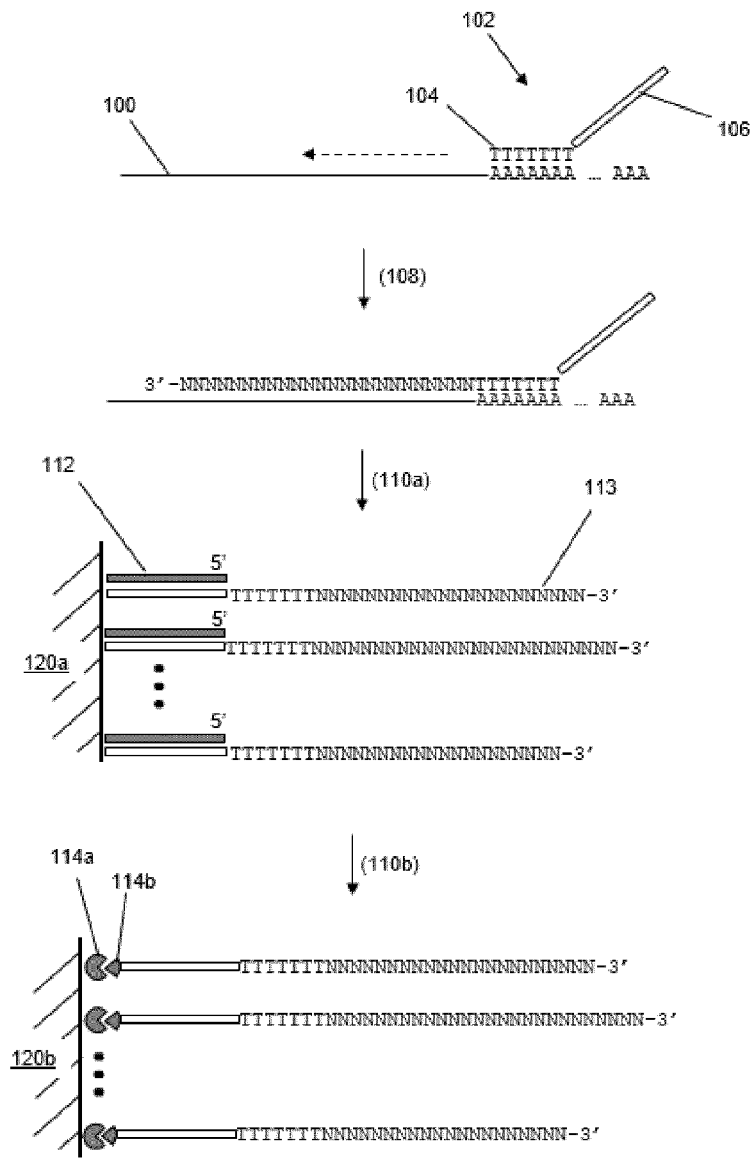
FIGS. 1B-1C illustrate one embodiment of the invention for directly synthesizing an oligonucleotide on the 3' end of cDNA molecules.
Figure 1C:
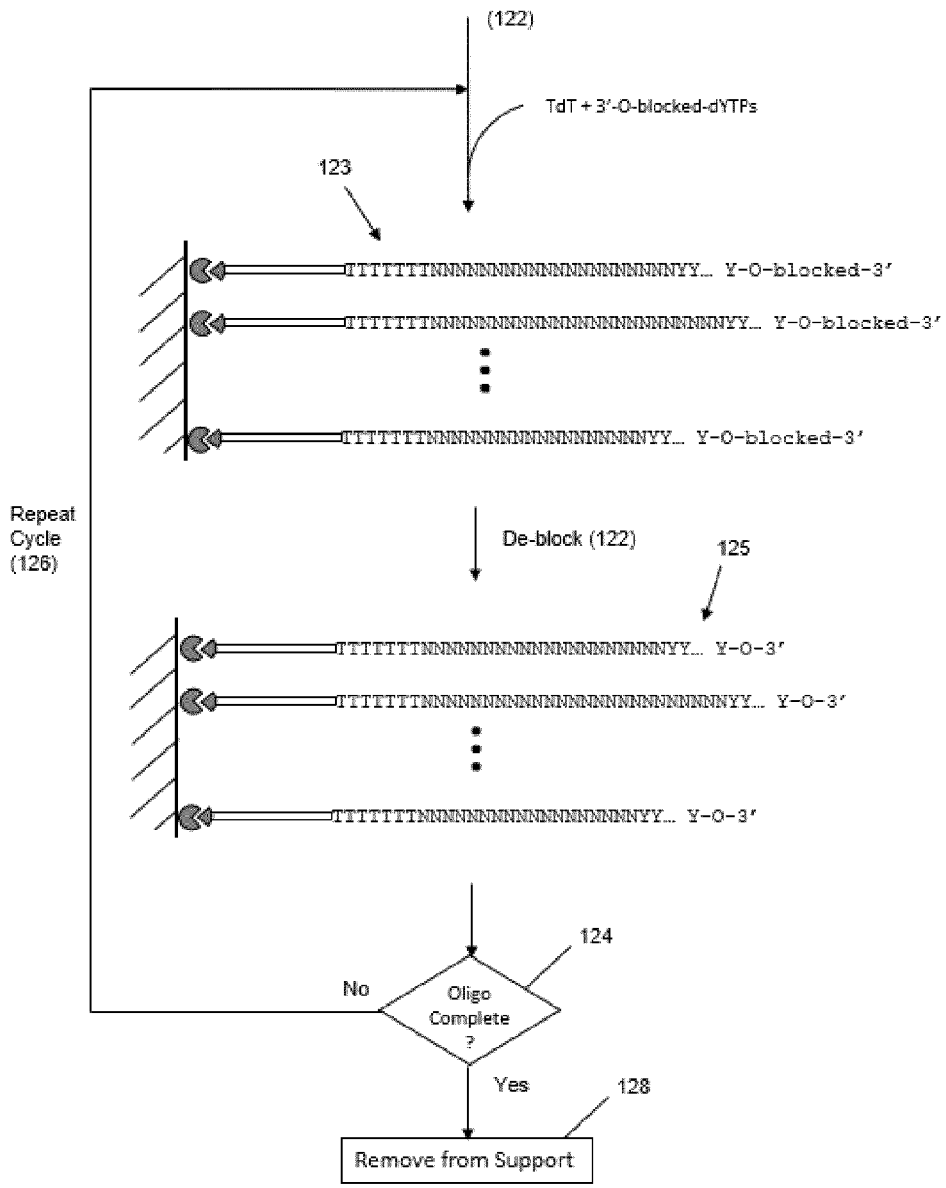

The above process is illustrated in FIGS. 1B-1C which show an embodiment where cDNAs have an oligonucleotide synthesized onto their 3' ends. Such cDNAs may be obtained, for example, from single cells isolated in reaction chambers. Cell-specific (or chamber-specific) oligonucleotides may be synthesized on such cDNAs. Afterwards, the contents of such reaction chambers may be combined, and the oligonucleotide-cDNA conjugates analyzed by large-scale sequence analysis to provide, for example, a single-cell transcriptome analysis of a population of cells, or transcriptome analysis of a group of cells from the same reactor that have been exposed to the same conditions. Primer (102) having 3'-polyT portion (104) is annealed to polyA region of messenger RNAs (mRNAs) (100) and extended (108) with a reverse transcriptase using conventional protocols to form cDNA (113)(SEQ ID NO: 16). Primer (102) also has portion (106) which provides a means for attaching the resulting extension products (i.e. the cDNAs) to a solid support. A wide variety of such attachment means are available including, but not limited to, a 5' oligonucleotide tail which may be anneal to a complementary strand attached to a solid support, a member of a click chemistry reaction pair which may be reacted with a complementary member attached to a solid support to form a covalent bond, a member of a non-nucleic acid binding pair which may form a complex with a complementary member attached to a solid phase support to form a non-covalent bond, an example of the latter being biotin and streptavidin. Returning to FIG. 1B, two of the above attachment modes are illustrated with solid support (120a) which has complementary oligonucleotide (112) attached by its 3' end and which captures cDNA (113) by forming a hybrid with portion (106) of extended primer (102), and with alternative support (120b) which has a member of a binding pair (114a)(such as, streptavidin) attached and which captures its complementary member (such as, biotin). The member of a binding pair attached to the cDNA does not require the presence of oligonucleotide tail (106); however, in some embodiments, such oligonucleotide (106) may include nucleotides or nucleotide sequences which may be employed for cleaving finished product from the solid supports, e.g. presence of a uracil for cleavage by USER treatment, or the recognition sequence of a restriction endonuclease, such as a nickase.

After cDNAs are cleavably or releasably attached to a solid support leaving their 3'-hydroxyls free, enzymatic synthesis can proceed to generate an oligonucleotide of a preterminded sequence on the free 3' ends, which is illustrated diagrammatically in FIG. 1C. After strands (123) (SEQ ID NO: 16) are attached to a solid support (for example, 120b via a binding pair), it is exposed to a reaction mixture comprising a template-free polymerase, such as TdT, and a 3'-O-blocked nucleoside triphosphate under conditions that permit the TdT to catalyze the formation of phosphate linkages from the 3'-hydroxyls of the cDNAs and the triphosphates of the incoming 3'-O-blocked nucleotides, thereby incorporating the first nucleotide of the desired oligonucleotide. The 3'-O-blocked nucleoside triphosphates of the extension reaction are shown as "3'-O-blocked dYTPs" in the figure. The 3'-O-blocked hydroxyls of the resulting product are deblocked (122) with an appropriate de-blocking agent to form extended cDNAs (125) having free 3'-hydroxyls. As will be discussed more fully below, the selection of a blocking group and its method of removal may vary widely for different embodiments. Such selections for a particular embodiment is within the skill of an ordinary practitioner by evaluation of factors such as, desired speed of synthesis, desired yield of the synthesis, fragility of the target biomolecules or cells being labeled, in particular, whether biologically compatible enzymatic deblocking is more desirable or whether harsher chemical deblocking is acceptable, and so on. Cycles are repeated (126) using the successive nucleotides of the desired oligonucleotide until the synthesis of the oligonucleotide is complete. In some embodiments, additional steps, such as, one or more washing steps, or a step of removing 3'-O-blocked-dYTPs, are included. After completion of the synthesis, the oligonucleotide-labeled cDNAs may be removed from the solid support for further analysis or use. In some embodiments, the cDNA may be retained on the solid support for further analysis or use.

In some embodiments, oligonucleotides may be synthesized on other biomolecules, such as antibodies, by a process similar to that of FIG. 1C provided that the biomolecules have initiator sequences attached.

Figure 1D:
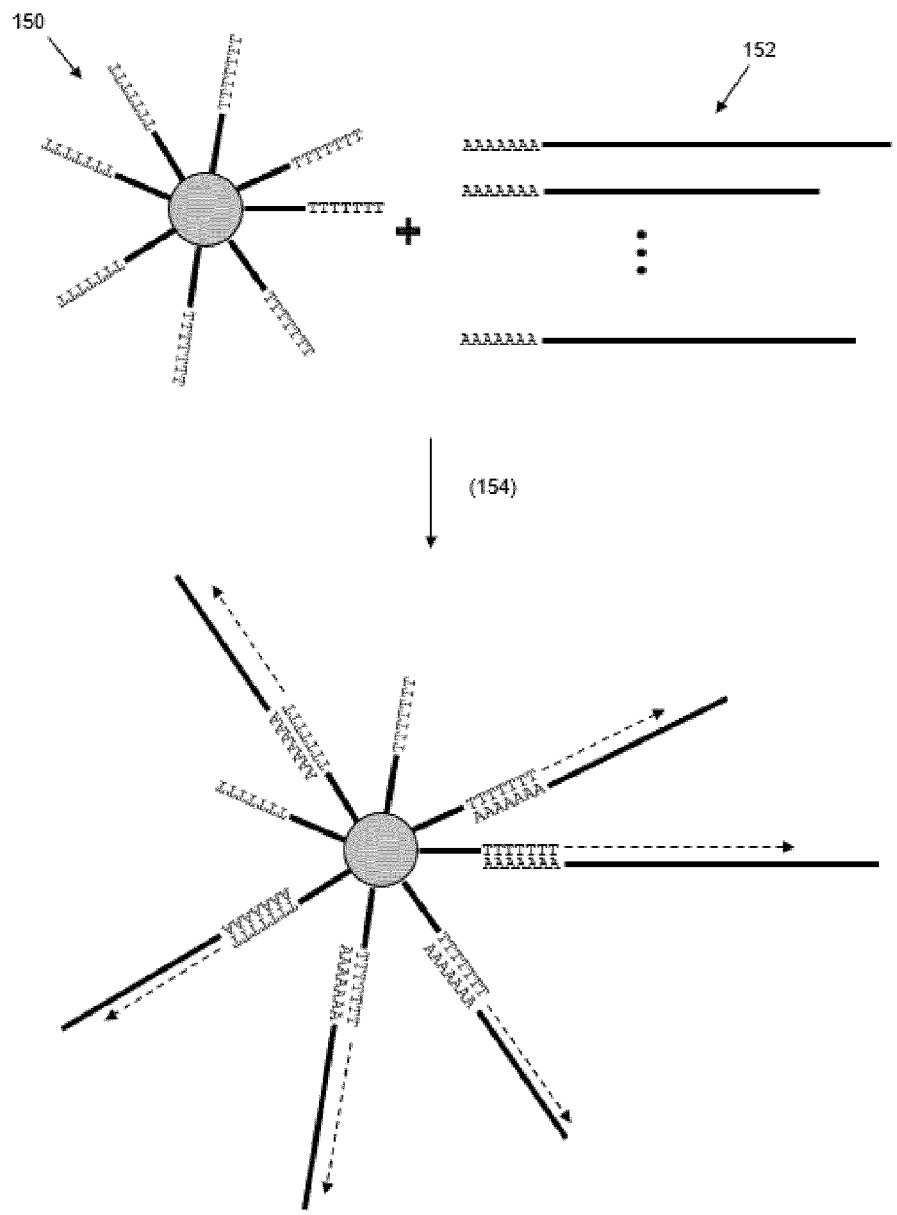
FIGS. 1D-1F illustrate the generation of tagged cDNA libraries on solid supports, e.g. beads or planar arrays, by applying the method illustrated in FIGS. 1B-1C.
Figure 1E:
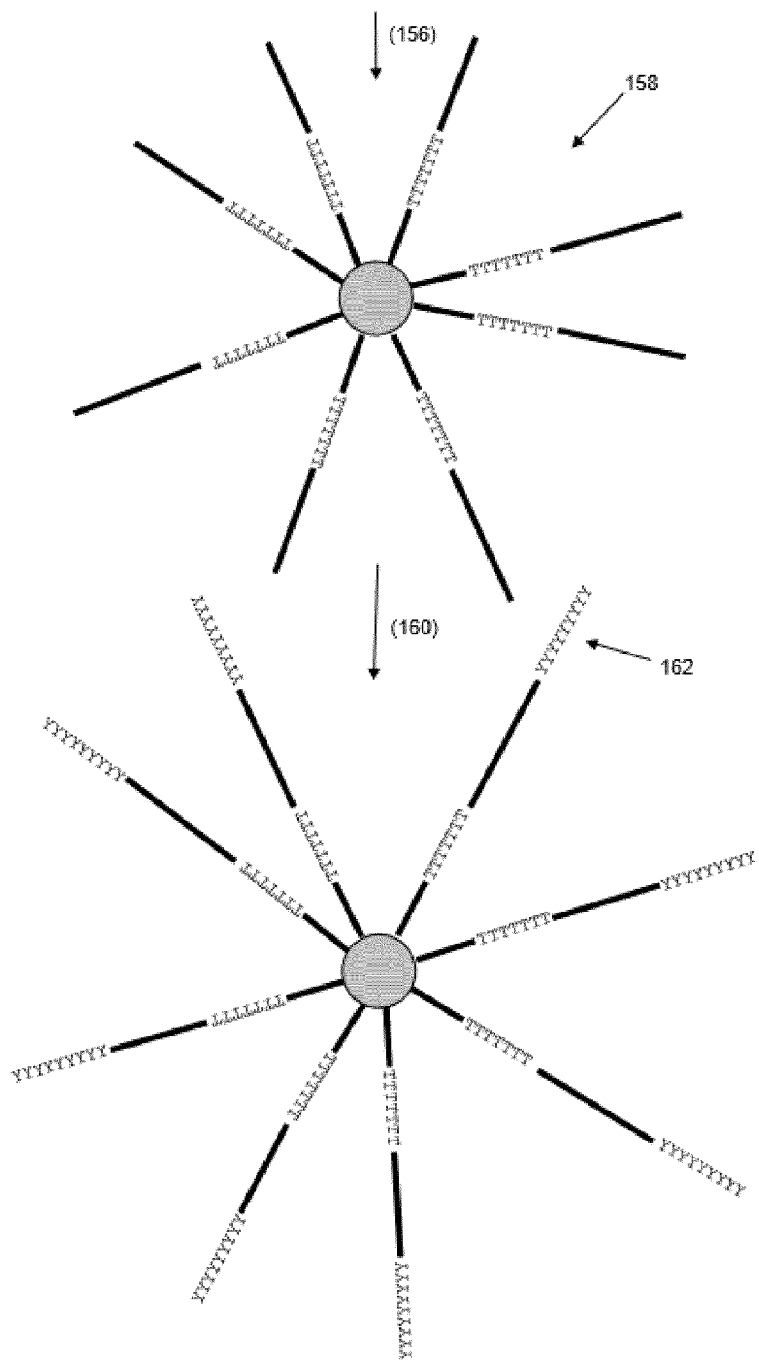

FIGS. 1D-1E illustrate how the above methods may be used with commercially available polyT beads to construct solid phase cDNA libraries, e.g. Dynabeads' M oligo(dT) magnetic beads, Bosnes et al, ThermoFisher Application Note (2017). PolyT beads (150) are combined with cell extract or lysate containing polyA RNA (152) under conditions that permit hybridization of the polyT segments of the beads to the polyA segments of the RNAs, after which the hybridized polyT segments are extended in a reverse transcription reaction. After removal of the RNA template (156), a solid phase cDNA library (158) results, which may then be processed in accordance with the method of FIGS. 1B and 1C (160) to synthesize barcodes, primer binding sites, or the like (162), to allow further analysis of the cDNAs. Such barcodes may uniquely designate a particular sample, such as a patient sample, or as described further below, such barcodes may designate uniquely a single cell.

In some embodiments, the invention is directed to methods of generating cDNA libraries each with a oligonucleotide label comprising the steps of: (a) capturing mRNA by hybridizing the mRNA to capture oligonucleotides attached to one or more solid supports, wherein the capture oligonucleotides are complementary to segments of the mRNA and wherein the capture oligonucleotides are attached to the one or more solid supports by 5-ends and have 3'-ends with free 3'-hydroxyls; (b) extending 3'-ends of the capture oligonucleotides with a reverse transcriptase using the captured mRNAs as templates to form cDNA libraries on the one or more solid supports; and (c) synthesizing a oligonucleotide label on each cDNA on the one or more solid support by template-free enzymatic synthesis. In some embodiments, the step of synthesizing comprises repeating cycles of (i) contacting under elongation conditions said cDNAs with a 3'-O-blocked nucleoside triphosphate and a template-independent DNA polymerase so that said cDNAs or elongated cDNAs with free 3'-hydroxyls are elongated by incorporation of a 3'-O-blocked nucleoside triphosphate to form 3'-O-blocked elongated cDNAs, and (ii) deblocking the elongated cDNA to form elongated cDNAs having free 3'-hydroxyls. In some embodiments, each of said cycles further comprises splitting said cDNAs or elongated cDNAs with free 3'-hydroxyls among separate reaction mixtures in which said cDNAs or elongated cDNAs with free 3'-hydroxyls are elongated by a different kind of nucleoside triphosphate to form said elongated cDNAs after which said elongated cDNAs of the separate reaction mixtures are combined. In some embodiments, the step of capturing includes capturing mRNA of a single cell on a bead to form the cDNA libraries that are cell-specific cDNA libraries and wherein the oligonucleotide labels are unique cell-specific oligonucleotide barcodes. In some embodiments, the step of synthesizing a unique cell-specific barcode is implemented by a split and mix synthesis method.

Template-Free Enzymatic Synthesis of Oligonucleotides

Generally, methods of template-free (or equivalently, "template-independent") enzymatic DNA synthesis comprise repeated cycles of steps, such as are illustrated in FIG. 1A, in which a predetermined nucleotide is coupled to an initiator or growing chain in each cycle. The general elements of template-free enzymatic synthesis is described in the following references: Ybert et al, International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57: 1821-1832 (2018); Mathews et al, Organic & Biomolecular Chemistry, DOI: 0.1039/c6ob01371f (2016); Schmitz et al, Organic Lett., 1(11): 1729-1731 (1999).

Initiator polynucleotides (1000) are provided, for example, attached to solid support (1020), which have free 3'-hydroxyl groups (1030). To the initiator polynucleotides (1000) (or elongated initiator polynucleotides in subsequent cycles) are added a 3'-O-protected-dNTP and a template-free polymerase, such as a TdT or variant thereof (e.g. Ybert et al, WO/2017/216472; Champion et al, WO2019/135007) under conditions (1040) effective for the enzymatic incorporation of the 3'-O-protected-dNTP onto the 3' end of the initiator polynucleotides (1000) (or elongated initiator polynucleotides). This reaction produces elongated initiator polynucleotides whose 3'-hydroxyls are protected (1060). If the elongated sequence is not complete, then another cycle of addition is implemented (1080). If the elongated initiator polynucleotide contains a competed sequence, then the 3'-O-protection group may be removed, or deprotected, and the desired sequence may be cleaved from the original initiator polynucleotide (1100). Such cleavage may be carried out using any of a variety of single strand cleavage techniques, for example, by inserting a cleavable nucleotide at a predetermined location within the original initiator polynucleotide. An exemplary cleavable nucleotide may be a uracil nucleotide which is cleaved by uracil DNA glycosylase. If the elongated initiator polynucleotide does not contain a completed sequence, then the 3'-O-protection groups are removed to expose free 3'-hydroxyls (1030) and the elongated initiator polynucleotides are subjected to another cycle of nucleotide addition and deprotection.

As used herein, an "initiator" (or equivalent terms, such as, "initiating fragment," "initiator nucleic acid," "initiator oligonucleotide," or the like) usually refers to a short oligonucleotide sequence with a free 3'-end, which can be further elongated by a template-free polymerase, such as TdT. In one embodiment, the initiating fragment is a DNA initiating fragment. In an alternative embodiment, the initiating fragment is an RNA initiating fragment. In some embodiments, an initiating fragment possesses between 3 and 100 nucleotides, in particular between 3 and 20 nucleotides. In some embodiments, the initiating fragment is single-stranded. In alternative embodiments, the initiating fragment is double-stranded. In some embodiments, an initiator may comprise a non-nucleic acid compound having a free hydroxyl to which a TdT may couple a 3'-O-protected dNTP, e.g. Baiga, U.S. patent publications US2019/0078065 and US2019/0078126.

Returning to FIG. 1A, in some embodiments, an ordered sequence of nucleotides is coupled to an initiator nucleic acid using a template-free polymerase, such as TdT, in the presence of 3'-O-protected dNTPs in each synthesis step. In some embodiments, the method of synthesizing an oligonucleotide comprises the steps of (a) providing an initiator having a free 3'-hydroxyl; (b) reacting under extension conditions the initiator or an extension intermediate having a free 3'-hydroxyl with a template-free polymerase in the presence of a 3'-0-protected nucleoside triphosphate to produce a 3'-O-protected extension intermediate; (c) deprotecting the extension intermediate to produce an extension intermediate with a free 3'-hydroxyl; and (d) repeating steps (b) and (c) until the polynucleotide is synthesized. (Sometimes the terms "extension intermediate" and "elongation fragment" are used interchangeably). In some embodiments, an initiator is provided as an oligonucleotide attached to a solid support, e.g. by its 5' end. The above method may also include washing steps after the reaction, or extension, step, as well as after the de-protecting step. For example, the step of reacting may include a sub-step of removing unincorporated nucleoside triphosphates, e.g. by washing, after a predetermined incubation period, or reaction time. Such predetermined incubation periods or reaction times may be a few seconds, e.g. 30 sec, to several minutes, e.g. 30 min.

When the sequence of polynucleotides on a synthesis support includes reverse complementary subsequences, secondary intra-molecular or cross-molecular structures may be created by the formation of hydrogen bonds between the reverse complementary regions. In some embodiments, base protecting moieties for exocyclic amines are selected so that hydrogens of the protected nitrogen cannot participate in hydrogen bonding, thereby preventing the formation of such secondary structures. That is, base protecting moieties may be employed to prevent the formation of hydrogen bonds, such as are formed in normal base pairing, for example, between nucleosides A and T and between G and C. At the end of a synthesis, the base protecting moieties may be removed and the polynucleotide product may be cleaved from the solid support, for example, by cleaving it from its initiator.

3'-O-blocked dNTPs without base protection may be purchased from commercial vendors or synthesized using published techniques, e.g. U.S. Pat. No. 7,057,026; Guo et al, Proc. Natl. Acad. Sci., 105(27): 9145-9150 (2008); Benner, U.S. Pat. Nos. 7,544,794 and 8,212,020; International patent publications WO2004/005667, WO91/06678; Canard et al, Gene (cited herein); Metzker et al, Nucleic Acids Research, 22: 4259-4267 (1994); Meng et al, J. Org. Chem., 14: 3248-3252 (3006); U.S. patent publication 2005/037991. 3'-O-blocked dNTPs with base protection may be synthesized as described below.

When base-protected dNTPs are employed the above method of FIG. 1A may further include a step (e) removing base protecting moieties, which in the case of acyl or amidine protection groups may (for example) include treating with concentrated ammonia.

The above method may also include capping step(s) as well as washing steps after the reacting, or extending, step, as well as after the deprotecting step. As mentioned above, in some embodiments, capping steps may be included in which non-extended free 3'-hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exonuclease activity, e.g. Exo I. For example, see Hyman, U.S. Pat. No. 5,436,143. Likewise, in some embodiments, strands that fail to be deblocked may be treated to either remove the strand or render it inert to further extensions.

In some embodiments, reaction conditions for an extension or elongation step may comprising the following: 2.0 µM purified TdT; 125-600 µM 3'-O-blocked dNTP (e.g. 3'-O—$NH_2$-blocked dNTP); about 10 to about 500 mM potassium cacodylate buffer (pH between 6.5 and 7.5) and from about 0.01 to about 10 mM of a divalent cation (e.g. $CoCl_2$ or $MnCl_2$), where the elongation reaction may be carried out in a 50 µL reaction volume, at a temperature within the range RT to 45° C., for 3 minutes. In embodiments, in which the 3'-O-blocked dNTPs are 3'-O-NEL-blocked dNTPs, reaction conditions for a deblocking step may comprise the following: 700 mM $NaNO_2$; 1 M sodium acetate (adjusted with acetic acid to pH in the range of 4.8-6.5), where the deblocking reaction may be carried out in a 50 µL volume, at a temperature within the range of RT to 45° C. for 30 seconds to several minutes.

Depending on particular applications, the steps of deblocking and/or cleaving may include a variety of chemical or physical conditions, e.g. light, heat, pH, presence of specific reagents, such as enzymes, which are able to cleave a specified chemical bond. Guidance in selecting 3'-O-blocking groups and corresponding de-blocking conditions may be found in the following references, which are incorporated by reference: Benner, U.S. Pat. Nos. 7,544,794 and 8,212,020; 5,808,045; 8,808,988; International patent publication WO91/06678; and references cited below. In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiments, the cleaving reaction involves TCEP, a palladium complex or sodium nitrite.

As noted above, in some embodiments it is desirable to employ two or more blocking groups that may be removed using orthogonal de-blocking conditions. The following exemplary pairs of blocking groups may be used in parallel synthesis embodiments (Table 1). It is understood that other blocking group pairs, or groups containing more than two, may be available for use in these embodiments of the invention.

TABLE 1

| Pairs of blocking groups | |
|---|---|
| 3'-O-NH2 | 3'-O-azidomethyl |
| 3'-O-NH2 | 3'-O-allyl |
| 3'-O-NH2 | 3'-O-phosphate |
| 3'-O-azidomethyl | 3'-O-allyl |
| 3'-O-azidomethyl | 3'-O-phosphate |
| 3'-O-allyl | 3'-O-phosphate |

Synthesizing oligonucleotides on living cells requires mild deblocking, or deprotection, conditions, that is, conditions that do not disrupt cellular membranes, denature proteins, interfere with key cellular functions, or the like. In some embodiments, deprotection conditions are within a range of physiological conditions compatible with cell survival. In such embodiments, enzymatic deprotection is desirable because it may be carried out under physiological conditions. In some embodiments specific enzymatically removable blocking groups are associated with specific enzymes for their removal. For example, ester- or acyl-based blocking groups may be removed with an esterase, such as acetylesterase, or like enzyme, and a phosphate blocking group may be removed with a 3' phosphatase, such as T4 polynucleotide kinase. By way of example, 3'-O-phosphates may be removed by treatment with as solution of 100 mM Tris-HCl (pH 6.5) 10 mM $MgCl_2$, 5 mM 2-mercaptoethanol, and one Unit T4 polynucleotide kinase. The reaction proceeds for one minute at a temperature of 37° C.

A "3'-phosphate-blocked" or "3'-phosphate-protected" nucleotide refers to nucleotides in which the hydroxyl group at the 3'-position is blocked by the presence of a phosphate containing moiety. Examples of 3'-phosphate-blocked nucleotides in accordance with the invention are nucleotidyl-3'-phosphate monoester/nucleotidyl-2',3'-cyclic phosphate, nucleotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not prevent dephosphorylation resulting in a free 3'-OH by a phosphatase.

Further examples of synthesis and enzymatic deprotection of 3'-O-ester-protected dNTPs or 3'-O-phosphate-protected dNTPs are described in the following references: Canard et al, Proc. Natl. Acad. Sci., 92:10859-10863 (1995); Canard et al, Gene, 148: 1-6 (1994); Cameron et al, Biochemistry, 16(23): 5120-5126 (1977); Rasolonjatovo et al, Nucleosides & Nucleotides, 18(4&5): 1021-1022 (1999); Ferrero et al, Monatshefte fur Chemie, 131: 585-616 (2000); Taunton-Rigby et al, J. Org. Chem., 38(5): 977-985 (1973); Uemura et al, Tetrahedron Lett., 30(29): 3819-3820 (1989); Becker et al, J. Biol. Chem., 242(5): 936-950 (1967); Tsien, International patent publication WO1991/006678.

In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

—O—Z wherein —Z is any of —$C(R)_2$—O—R", —$C(R)_2$—$N(IC)_2$, —$C(R)_2$—N(H)R", —$C(R')_2$—S—R" and —$C(R')_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or $(R')_2$ represents a group of formula =$C(R''')_2$ wherein each R'" may be the same or different and is selected from the group comprising hydrogen and halogen atoms and alkyl groups, with the proviso that in some embodiments the alkyl of each R" has from 1 to 3 carbon atoms; and wherein the molecule may be reacted to yield an intermediate in which each R" is exchanged for H or, where Z is —$(R')_2$—F, the F is exchanged for OH, SH or $NH_2$, preferably OH, which intermediate dissociates under aqueous conditions to afford a molecule with a free 3'-OH; with the proviso that where Z is —$C(R')_2$—S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, -Z of the modified nucleotide or nucleoside is of formula —$C(R')_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less. In some embodiments, Z is an enzymatically cleavable organic moiety with or without heteroatoms having a molecular weight of 200 or less. In other embodiments, Z is an enzymatically cleavable organic moiety with or without heteroatoms having a molecular weight of 100 or less. In other embodiments, Z is an enzymatically cleavable organic moiety with or without heteroatoms having a molecular weight of 50 or less. In other embodiments, Z is an enzymatically cleavable ester group having a molecular weight of 200 or less. In other embodiments, Z is a phosphate group removable by a 3'-phosphatase. In some embodiments, one or more of the following 3'-phosphatases may be used with the manufacturer's recommended protocols: T4 polynucleotide kinase, calf intestinal alkaline phosphatase, recombinant shrimp alkaline phosphatase (e.g. available from New England Biolabs, Beverly, MA)

In a further embodiment, the 3'-blocked nucleotide triphosphate is blocked by either a 3'-O-azidomethyl, 3'-O—$NH_2$ or 3'-O-allyl group.

In still other embodiments, 3'-O-blocking groups of the invention include 3'4)-methyl, 3'-O-(2-nitrobenzyl), 3'-O-allyl, 3'-O-amine, 3'-O-azidomethyl, 3'-O-tert-butoxy ethoxy, 3'-O-(2-cyanoethyl), and 3'-O-propargyl.

In some embodiments, 3'-O-protection groups are electrochemically labile groups. That is, deprotection or cleavage of the protection group is accomplished by changing the electrochemical conditions in the vicinity of the protection group which result in cleavage. Such changes in electrochemical conditions may be brought about by changing or applying a physical quantity, such as a voltage difference or light to activate auxiliary species which, in turn, cause changes in the electrochemical conditions at the site of the protection group, such as an increase or decrease in pH. In some embodiments, electrochemically labile groups include, for example, pH-sensitive protection groups that are cleaved whenever the pH is changed to a predetermined value. In other embodiments, electrochemically labile groups include protecting groups which are cleaved directly whenever reducing or oxidizing conditions are changed, for example, by increasing or decreasing a voltage difference at the site of the protection group.

In some embodiments, enzymatic synthesis methods employ TdT variants that display increased incorporation activity with respect to 3'-O-modified nucleoside triphosphates. For example, such TdT variants may be produced using techniques described in Champion et al, U.S. patent Ser. No. 10/435,676, which is incorporated herein by reference. In some embodiments, a TdT variant is employed having an amino acid sequence at least 60 percent identical to SEQ ID NO: 2 and a substitution at a first arginine at position 207 and a substitution at a second arginine at position 325, or functionally equivalent residues thereof. In some embodiments, a terminal deoxynucleotidyl transferase (TdT) variant is employed that has an amino acid sequence at least sixty percent identical to an amino acid sequence selected from SEQ ID NO: 2, 3, 4, 5, 6, 7, 8, 9, 10, 11, 12, 13, 14 or 15 with a substitution of arginine ("first arginine") at position 207 with respect to SEQ ID NOs 2, 3, 4, 6, 7, 9, 12 and 13, at position 206 with respect to SEQ ID NO 5, at position 208 with respect to SEQ ID NOs 8 and 10, at position 205 with respect to SEQ ID NO 11, at position 216 with respect to SEQ ID NO 14 and at position 210 with respect to SEQ ID NO 15; and a substitution of arginine ("second arginine") at position 325 with respect to SEQ ID NOs 2, 9 and 13, at position 324 with respect to SEQ ID NOs 3 and 4, at position 320 with respect to SEQ ID NO 320, at position 331 with respect to SEQ ID NOs 6 and 8, at position 323 with respect to SEQ ID NO 11, at position 328 with respect to SEQ ID NOs 12 and 15, and at position 338 with respect to SEQ ID NO 14; or functionally equivalent residues thereof; wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. As used herein, the percent identity values used to compare a reference sequence to a variant sequence do not include the expressly specified amino acid positions containing substitutions of the variant sequence; that is, the percent identity relationship is between sequences of a reference protein and sequences of a variant protein outside of the expressly specified positions containing substitutions in the variant. Thus, for example, if the reference sequence and the variant sequence each comprised 100 amino acids and the variant sequence had mutations at positions 25 and 81, then the percent homology would be in regard to sequences 1-24, 26-80 and 82-100.

In regard to (ii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, the above TdT variants have substitutions at the first and second arginines as shown in Table 2.

TABLE 2

| SEQ ID NO | TdT variants Substitutions | | | | |
|---|---|---|---|---|---|
| 1 | M192R/Q | C302G/R | R336L/N | R454P/N/A/V | E457N/L/T/S/K |
| 2 | M63R/Q | C173G/R | R207L/N | R325P/N/A/V | E328N/L/T/S/K |
| 3 | M63R/Q | C173G/R | R207L/N | R324P/N/A/V | E327N/L/T/S/K |
| 4 | M63R/Q | C173G/R | R207L/N | R324P/N/A/V | E327N/L/T/S/K |
| 5 | — | C172G/R | R206L/N | R320P/N/A/V | — |
| 6 | M63R/Q | C173G/R | R207L/N | R331P/N/A/V | E334N/L/T/S/K |
| 7 | M63R/Q | C173G/R | R207L/N | — | E328N/L/T/S/K |
| 8 | — | C174G/R | R208L/N | R331P/N/A/V | E334N/L/T/S/K |
| 9 | M73R/Q | C173G/R | R207L/N | R325P/N/A/V | E328N/L/T/S/K |
| 10 | M64R/Q | C174G/R | R208L/N | — | E329N/L/T/S/K |
| 11 | M61R/Q | C171G/R | R205L/N | R323P/N/A/V | E326N/L/T/S/K |
| 12 | M63R/Q | C173G/R | R207L/N | R328P/N/A/V | E331N/L/T/S/K |
| 13 | — | C173G/R | R207L/N | R325P/N/A/V | E328N/L/T/S/K |
| 14 | M63R/Q | C182G/R | R216L/N | R338P/N/A/V | E341N/L/T/S/K |
| 15 | M66R/Q | C176G/R | R210L/N | R328P/N/A/V | E331N/L/T/S/K |

In some embodiments, further TdT variants for use with methods of the invention include one or more of the further substitutions of methionine, cysteine or glutamic acid, as shown in Table 1.

Further specific TdT variants that may be used in methods of the invention are set forth in Table 3. Each of the TdT variants DS1001 through DS1018 of Table 2 comprises an amino acid sequence at least 60 percent identical to SEQ ID NO 2 and comprises the substitutions at the indicated positions. In some embodiments, TdT variants DS1001 through DS1018 comprises an amino acid sequence at least 80 percent identical to SEQ ID NO 2 and comprises the substitutions at the indicated positions; in some embodiments, TdT variants DS1001 through DS1018 comprises an amino acid sequence at least 90 percent identical to SEQ ID NO 2 and comprises the substitutions at the indicated positions; in some embodiments, TdT variants DS1001 through DS1018 comprises an amino acid sequence at least 95 percent identical to SEQ ID NO 2 and comprises the substitutions at the indicated positions; in some embodiments, TdT variants DS1001 through DS1018 comprises an amino acid sequence at least 97 percent identical to SEQ ID NO 2 and comprises the substitutions at the indicated positions; in some embodiments, TdT variants DS1001 through DS1018 comprises an amino acid sequence at least 98 percent identical to SEQ ID NO 2 and comprises the substitutions at the indicated positions; in some embodiments, TdT variants DS1001 through DS1018 comprises an amino acid sequence at least 99 percent identical to SEQ ID NO 2 and comprises the substitutions at the indicated positions.

TABLE 3

Specific TdT Variants for Use with Methods of the Invention

| | |
|---|---|
| DS1001 (TH M27) | A17V + L52F + M63R + A108V + C173G + R207L + K265T + G284P + E289V + R325P + E328N + R351K |
| DS1002 (M44) | A17V + Q37E + D41R + L52F + G57E + M63R + S94R + G98E + A108V + S119A + L131R + S146E + Q149R + C173G + R207L + K265T + G284P + E289V + R325P + Q326F + E328N + H337D + R351K + W377R |
| DS1003 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1004 (M45) | A17V + Q37E + D41R + L52F + G57E + M63R + S94R + G98E + A108V + S146E + Q149R + C173G + F193Y + V199M + M201V + R207L + K265T + G284P + E289V + R325A + Q326F + E328N + R351K |
| DS1005 | A17V + Q37E + D41R + L52F + G57E + M63R + S94R + G98E + A108V + S146E + Q149R + C173G + F193Y + V199M + M201V + R207L + K265T + G284P + E289V + Q326F + E328N + R351K |
| DS1006 (M46) | L52F + A108V + R351K + A17V + Q37E + D41R + G57E + C59R + L60D + M63R + S94R + G98E + S119A + L131R + S146E + Q149R + C173G + R207L + K265T + G284P + E289V + R325A + Q326F + E328N |
| DS1007 (M47) | L52F + A108V + R351K + A17V + Q37E + D41R + G57E + C59R + L60D + M63R + S94R + G98E + K118Q + S119A + L131R + S146E + Q149R + C173G + R207L + K265T + G284P + E289V + R325A + Q326F + E328N + W377R |
| DS1008 | A17V + Q37E + D41R + L52F + G57E + C59R + L60D + M63R + S94R + G98E + A108V + S119A + L131R + S146E + Q149R + C173G + R207L + F259S + Q261L + G284P + E289V + R325A + Q326F + E328N + R351K + W377R |
| DS1009 (MS 13-34) | A17V + D41R + L53F + G57E + C59R + L60D + M63R + S94R + G98E + K118Q + S119A + L131R + S146E + Q149R + C173G + R207L + K265T + G284P + E289V + R325A + Q326F + R351K + W377R |
| DS1010 (MS 34-1) | A17V + D41R + L52F + G57E + C59R + L60D + M63R + S94R + G98E + A108V + S119A + L131R + S146E + Q149R + R207L + K265T + G284P + E289V + R325A + Q326F + R351K |
| DS1011 | A17V + D41R + L53F + G57E + C59R + L60D + M63R + S94R + G98E + K118Q + S119A + L131R + S146E + Q149R + C173G + R207L + K265T + G284P + E289V + Q326F + R351K + W377R |
| DS1012 (M48) | A17V + Q37E + D41R + L52F + G57E + C59R + L60D + M63R + S94R + G98E + A108V + S119A + L131R + S146E + Q149R + C173G + R207L + F259S + Q261L, G284P + E289V + R325A + Q326F + E328N + R351K + W377R |
| DS1013 | A17V + Q37E + D41R + L52F + G57E + M63R + S94R + G98E + A108V + S146E + Q149R + C173G + R207L + K265T + G284P + E289V + R325A + Q326F + E328N + R351K |
| DS1014 (M49) | A17V + Q37E + D41R + L52F + G57E + C59R + L60D + M63R + S94R + G98E + A108V + S119A + L131R + S146E + Q149R + C173G + R207L + E257D + F259S + K260R + Q261L + G284P + E289V + R325A + Q326F + E328N + R351K + W377R |
| DS1015 | A17V + Q37E + D41R + L52F + G57E + C59R + L60D + M63R + S94R + G98E + A108V + S119A + L131R + S146E + Q149R + C173G + F193Y + V199M + M201V + R207L + E257D + F259S + K260R + Q261L + G284P + E289V + R325A + Q326F + E328N + R351K + W377R |
| DS1016 TH c2_5 | A17V + D41R + L52F + G57E + M63R + S94R + G98E + A108V + S146E + Q149R + C173G + M184T + R207L + K209H + G284L + E289A + R325V + E328K + R351K |
| DS1017 (M27) | A17V + L52F + G57E + M63R + A108V + C173G + R207L + K265T + G284P + E289V + R325P + E328N + R351K |
| DS1018 (M60) | A17V + L32T + Q37R + D41R + L52F + G57E + C59R + L60D + M63R + S67A + S94R + G98E + A108V + S119A + L131R + S146E + Q149R + V171A + S172E + C173R + V182I + S183E + R207L + K209H + M210K + T211I + E223G + A224P + E228D + Q261L + G284P + E289V + R325A + Q326F + E328N + R351K + D372E |

TdT variants of the invention as described above each comprise an amino acid sequence having a percent sequence identity with a specified SEQ ID NO, subject to the presence of indicated substitutions. In some embodiments, the number and type of sequence differences between a TdT variant of the invention described in this manner and the specified SEQ ID NO may be due to substitutions, deletion and/or insertions, and the amino acids substituted, deleted and/or inserted may comprise any amino acid. In some embodiments, such deletions, substitutions and/or insertions comprise only naturally occurring amino acids. In some embodiments, substitutions comprise only conservative, or synonymous, amino acid changes, as described in Grantham, Science, 185: 862-864 (1974). That is, a substitution of an amino acid can occur only among members of its set of synonymous amino acids. In some embodiments, sets of synonymous amino acids that may be employed are set forth in Table 4A.

TABLE 4A

Synonymous Sets of Amino Acids I

| Amino Acid | Synonymous Set |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Cys, Ser, Thr |
| His | His, Glu, Lys, Gln, Thr, Arg |
| Gln | Gln, Glu, Lys, Asn, His, Thr, Arg |
| Asn | Asn, Gln, Asp, Ser |
| Lys | Lys, Glu, Gln, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

In some embodiments, sets of synonymous amino acids that may be employed are set forth in Table 4B.

TABLE 4B

Synonymous Sets of Amino Acids II

| Amino Acid | Synonymous Set |
|---|---|
| Ser | Ser |
| Arg | Arg, Lys, His |
| Leu | Ile, Phe, Met, Leu |
| Pro | Ala, Pro |
| Thr | Thr |
| Ala | Pro, Ala |
| Val | Met, Ile Val |
| Gly | Gly |
| Ile | Met, Phe, Val, Leu, Ile |
| Phe | Met, Tyr, Ile, Leu, Phe |
| Tyr | Trp, Met |
| Cys | Cys, Ser |
| His | His, Gln, Arg |
| Gln | Gln, Glu, His |
| Asn | Asn, Asp |
| Lys | Lys, Arg |
| Asp | Asp, Asn |
| Glu | Glu, Gln |
| Met | Met, Phe, Ile, Val, Leu |
| Trp | Trp |

Synthesizing Oligonucleotides on Biomolecules

Biomolecules on which oligonucleotides may be synthesized in accordance with the invention include, but are not limited to, polynucleotides, peptides, proteins, glycans, polysaccharides, and the like. Virtually any biomolecule or other material to which an initiator can be attached can have an oligonucleotide synthesized on it by methods of the invention. As noted above, for polynucleotides, such as cDNAs, genomic fragments, or the like, a variety of different initiator attachment schemes are available, including schemes resulting in a covalent bond between an initiator and a biomolecule or surface and schemes resulting in a non-covalent bond between an initiator and biomolecule or surface, such as the formation of a duplex between the initiator and another complementary oligonucleotide attached to a surface or biomolecule, or the formation of a complex between a capture moiety and its complementary moiety, such as a biotin and streptavidin.

Polynucleotides to which an oligonucleotide has been synthesized may be detached from a solid support in a variety of ways. Initiators hybridized to a capture oligonucleotide may simply be melted or dehybridized from the capture oligonucleotide, or the duplex may be designed to include a restriction endonuclease or nickase recognition site. In embodiments in which an initiator is covalently attached to a surface, several techniques are available to cleave a single strand, e.g. inserting a uracil at a predetermined location in an initiator, Delort et al, Nucleic Acids Research, 13: 319-335 (1985).

Oligonucleotide initiators may be attached to proteins, such as antibodies, using well-known techniques, such as described in the following references: Hermanson (cited above); Baskin et al, Proc. Natl. Acad. Sci., 104(43): 16793-16797 (2007); Gong et al, Bioconjugate Chemistry, 27: 217-225 (2016); Horisawa, Frontiers in Physiology, 5: 1-6 (2014); Jewett et al, Chem. Soc. Rev., 39(4): 1272-1279 (2010); U.S. Pat. No. 5,665,539; and the like.

Once an initiator is attached, then enzymatic synthesis may be performed to extend the initiator. In some embodiments, proteins are reversibly attached to a solid support prior to synthesis. As with polynucleotides, such attachment may be covalent or non-covalent. If the protein is a recombinant protein attachment may be by way of a peptide tag, such as a poly-histidine tag, or like method. In some embodiments, proteins may be immobilized on a solid support by capture and binding to an antibody attached to the solid support.

Synthesizing Oligonucleotides on Biological Cells

The value of single cell measurements has been long appreciated for assessing rare subpopulations which otherwise would be undetectable from ensemble measurements, which provide only averages of cellular parameters from many cells, e.g. Di Carlo et al, Methods in Molecular Biology, 853: 1-9 (2012). As a result, a range of technologies has been developed for high-throughput single cell analysis, e.g. reviewed in Shapiro et al, Nature Reviews Genetics, 14: 618-630 (2013). A common approach in many of these technologies has included the formation of single cell-containing reactors by stochastically distributing cells of a population into small reaction volumes for analysis. Although such stochastic methods permit handling cells in "bulk" mixtures, the methods allow only limited control of the numbers of cells that end up in the small volumes, e.g. Koster et al, LabChip, 8: 1110-1115 (2008), so that typically the higher the concentration of cells in the starting population, the greater the number of small volumes that end up with two or more cells. Since successful single-cell analysis depends on having only one cell in each reaction volume, very low cellular concentrations of starting populations are selected to avoid the occurrence of cellular doublets. Unfortunately, this creates significant inefficiencies in analyses conducted downstream of such stochastic isolation steps. This problem is exacerbated when cell-specific barcodes are delivered to cells by coalescing droplets carrying cells with droplets carrying barcoded beads, which are also stochastically distributed in the droplets. Thus, the availability of a technique to directly synthesis a unique barcode on a cell would obviate the requirement of delivering a single bead to a single cell.

Methods of the invention may be applied to a wide range of biological cells, including but not limited to, mammalian cells, yeast cells, bacterial cells, protozoan cells, fungal cells, plant cells, and the like. In some embodiments, methods of the invention are applied to mammalian cells. Such mammalian cells may be free of tissues, e.g. white blood cells, or such cells may be tissue-bound cells which have been disaggregated. During synthesis of oligonucleotides on living cells reaction conditions are selected to maintain the cells in a viable state. Such conditions (sometimes referred to herein as "biological conditions" or "viable conditions" or "cell-viable conditions") include disposing and maintaining cells in reaction mixtures that comprise a physiological salt solution that permits a balance of osmotic pressure across cell membranes, a pH in the range of from 6.8 to 7.8, and a temperature in a range of from 15° C. to 41° C. In some embodiments, a temperature in the range of from 25° C. to 38° C. is employed. Physiological salt solutions may include sodium, calcium and/or potassium ions in an aqueous solvent at a concentration in the range of 0.8-1.0 percent (w/v). For example, 0.9 percent (w/v) of sodium chloride in distilled water is a common physiological salt solution. It is understood that such physiological conditions are averages and that in particular implementations of the invention there may be brief deviations from such conditions without significant harm to the cells or biomolecules, for example, in deprotection steps. Likewise, it is understood that some biological cells may be viable in conditions outside those mentioned above, e.g. thermophilic organisms.

Attaching initiators to cells. A first step to generating a unique cellular label is attaching initiators to cells of a target population. This is accomplished using a variety of conventional techniques including, but not limited to, attaching an initiator to one or more antibodies specific for cell surface markers, integrating an initiator into an aptamer specific for cell surface markers, using click chemistry techniques to attach initiators directly to cell surface proteins, generating initiators with 5'-lipophilic tails which insert into the membranes of the target cells. Examples of such labeling techniques are described in the following references: Weber et al, Biomacromolecules, 15: 4621-4626 (2014); Borisenko et al, Nucleic Acids Research, 37(4): e28 (2009); Sano et al, Science, 258: 120-122 (1992); Kazane et al, Proc. Natl. Acad. Sci., 109(10): 3731-3736 (2012); Nikic et al, Nature Protocols, 10: 780-791 (2015); Baskin et al, Proc. Natl. Acad. Sci., 104(43): 16793-16797 (2007); Jewitt et al, Chem. Soc. Rev., 39(4): 1272-1279 (2010); Li et al, Chem. Sci., 8: 2107 (2017).

"Split and Mix" Barcoding of Cells. In some embodiments, the invention provides methods for uniquely barcoding cells, either living cells, fixed cells, or fixed and permeabilized cells. For example, in testing or screening compounds for biological effects, such as changes in gene expression, populations of cells after cells have been exposed to different agents or compounds. Samples of such cells may be tested while viable for changes in gene expression, for example, of cell surface molecules, or such cells may be fixed and permeabilized and tested for changes in the expression of both cellular proteins and mRNA. In some embodiments, protein expression may be monitored using one or more protein-specific antibodies each linked to a distinct initiator that may be extended using the enzymatic synthesis methods of the invention. In some embodiments, mRNA expression may be monitored using mRNA-specific primers to generate cDNAs that may be extended as described in FIGS. 1B-1C. After barcodes are synthesized (whether before or after testing), they may be harvested and tabulated, for example, by amplification, isolation, and sequencing, as illustrated in FIG. 2B for barcodes carried by antibodies. Such measurements are analogous to the more cumbersome barcoding scheme based on the hybridization of barcode subunits, e.g. described in Nolan, U.S. patent publication 2016/0251697. Thus, in some embodiments, the invention may be employed to measure the distribution of multiple epitopes on single cells of a large population of cells.

Figure 1F:
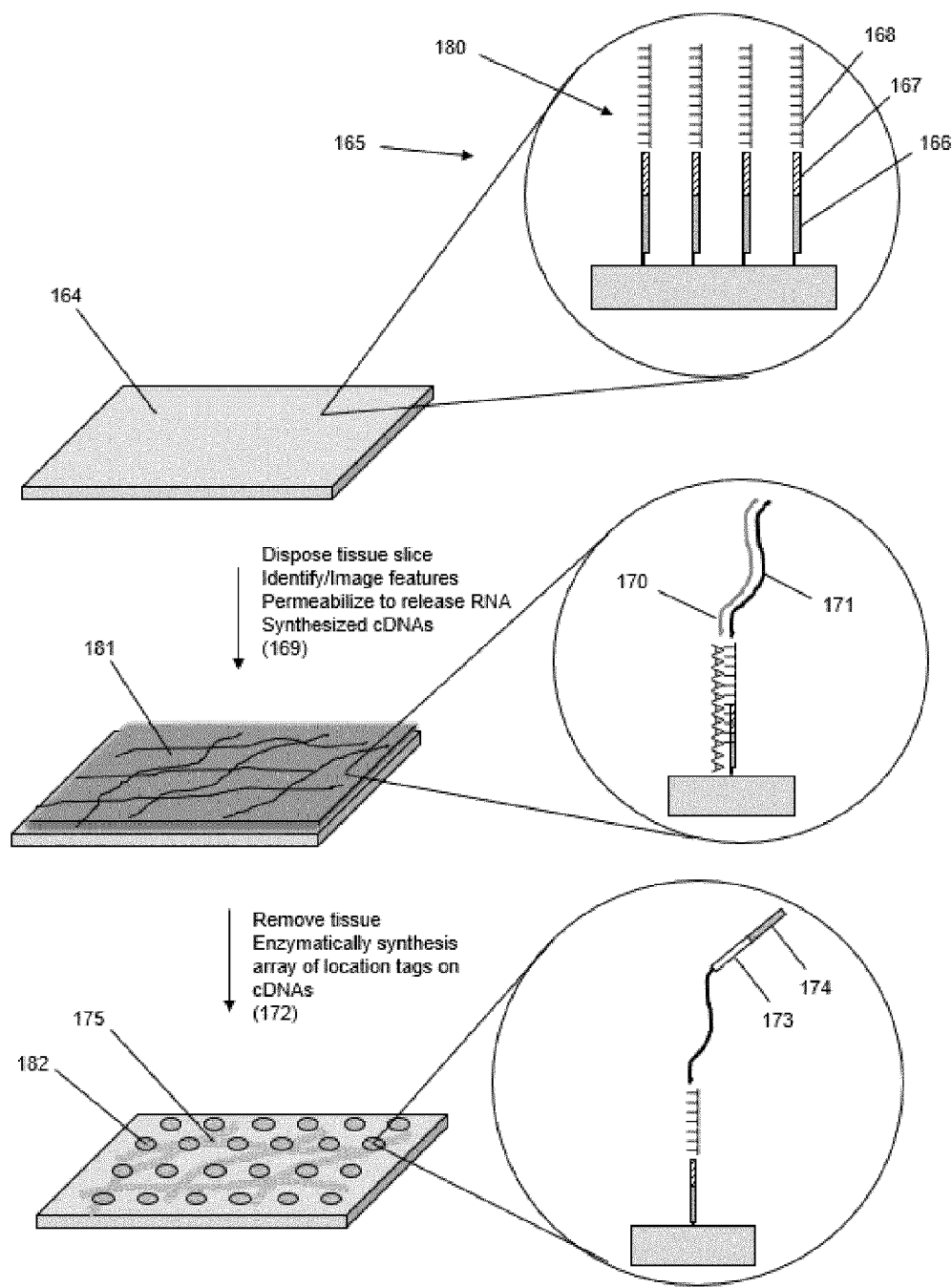

Similar to adding unique cellular tags in the case of beads described above, the invention also may be used to attach unique position tags in the case of spatial patterns of gene expression in a tissue slice disposed on a planar surface, as illustrated in FIG. 1F. Procedures for placing tissue slices on a planar array of oligonucleotides, identifying and imaging tissue features (such as cell boundaries), permeablizing cells of tissues, implementing reverse transcriptase reactions to produce a cDNA library attached to a planar array are disclosed in Stahl et al, Science, 353: 78-82 (2016); and Frisen et al, U.S. Pat. Nos. 9,593,365 and 10,030,261; and like references, which are incorporated herein by reference. Briefly, referring to FIG. 1F, planar array (164) is provided with a uniform coating of oligonucleotides (180), with a controlled density, attached by their 5' ends, wherein the oligonucleotides (shown in magnified view (165)) comprise segment (166), such as a primer binding site, for later amplification and manipulation of a cDNA, optional segment (167) comprising a molecular tag (sometimes referred to as a "unique molecular identifier" or UMI) which facilitates quantification of cDNA molecules even after amplification, and segment (168), such as a polyT segment, which permits capture of mRNA released from cells. The UMI (167) may comprise a random nucleotide segment. Oligonucleotides (180) may be made in bulk using conventional techniques and applied to the surface of planar array (164) in a single step. Different kinds of oligonucleotides, for example, oligonucleotides with different position tags are not required. Segment (167) may also include a cleavable linker or cleavable nucleotide for releasing cDNAs for analysis, such as, by sequencing. Onto array (164) is disposed a slice or thin layer (181) (e.g. 100-1000 µm thick) of tissue, which it is then treated (169) (i) to identify features, such as cells or sub-tissues, of interest and to record and/or correlate such information to locations on planar array (164), and (ii) to permeablized cells in the tissue so that mRNA is released and allowed to diffuse to and be captured by oligonucleotides (180). The image information is used to define regions on array (164) within which common position tags are synthesized on cDNAs. Treatments may include staining with tissue-specific or biomolecule-specific compounds or dyes. The position tags allow cDNAs to be harvested and sequenced in bulk, yet be related to specific regions by their position tags. After the above steps (i) and (ii), reagents for a reverse transcriptase reaction are applied in order to synthesize cDNAs (171) using captured mRNAs (170) as templates to produce a spatial cDNA library array. Tissue slice (181) is then removed leaving array (164) with a pattern of different cDNAs attached to its surface. The different cDNAs at the different positions may be identified and quantified by attaching position tags to samples of cDNAs from a plurality of locations by inkjet delivery of synthesis reagents for the tags, which is illustrated in FIG. 1E by the superposition of synthesis locations (182) on cDNA pattern (175). In some embodiments, such plurality may be at least 100 positions, or at least 1000 positions, or at least 10,000 positions; in other embodiments, such plurality may be in the range of from 10 to 50,000 positions; or from 10 to 10,000 positions; or from 10 to 1000 positions. Guidance for design and control of inkjet delivery systems is well known by those with skill in the art and may be found in U.S. patent publication US2003/0170698 and U.S. Pat. Nos. 6,306,599; 6,323,043; 7,276,336; 7,534,561; and like references. Alternatively, an electrode array may be employed wherein synthesis steps, such as deprotection of electrochemically sensitive protection groups, e.g. 3'-O-azidomethyl, may be effected by altering a potential at electrodes in the array, e.g. Montgomery, U.S. Pat. Nos. 6,093,302, 6,444,111 and 6,280,595; Gindilis, U.S. Pat. No. 9,339,782; Maurer et al, U.S. Pat. No. 9,267,213; Maurer et al, PLosOne, December 2006, issue 1, e34; Fomina et al, LabChip, 16: 2236-2244 (2016); Kavusi et al, U.S. Pat. No. 9,075,041; Johnson et al, U.S. Pat. Nos. 9,874,538 and 9,910,008; Gordon et al, U.S. Pat. No. 6,251,595; Levine et al, and the like. IEEE J. Solid State Circuits, 43: 1859-1871 (2008); and the like.

Position tags (173) are selected (e.g. are long enough) to uniquely identify each location or region of interest. Additional segment (174) may be added to facilitate manipulation and sequencing of cDNAs (171). In some embodiments, this application of the invention may be carried out with the following steps: (a) providing an array comprising a uniform coating of capture probes each comprising a capture segment; (b) contacting a tissue sample with the array and allowing the nucleic acid of the tissue sample to interact with the capture domain of the capture probe so that the nucleic acid is captured; (c) treating the tissue sample to identify different regions of the tissue sample; (d) generating a nucleic acid molecule from the nucleic acid that interacts with the capture domain; (e) enzymatically synthesizing position tags onto the nucleic acid molecules; (f) determining the region that is associated with the nucleic acid that interacts with the capture domain; and (e) correlating the determined regions to the cDNAs. In some embodiments, the nucleic acid molecules from the tissue sample is RNA. In other embodiments, the nucleic acid molecules from the tissue sample may be genomic DNA. In other embodiments, the nucleic acid molecules from the tissue sample may be mRNA.

Figure 1G:
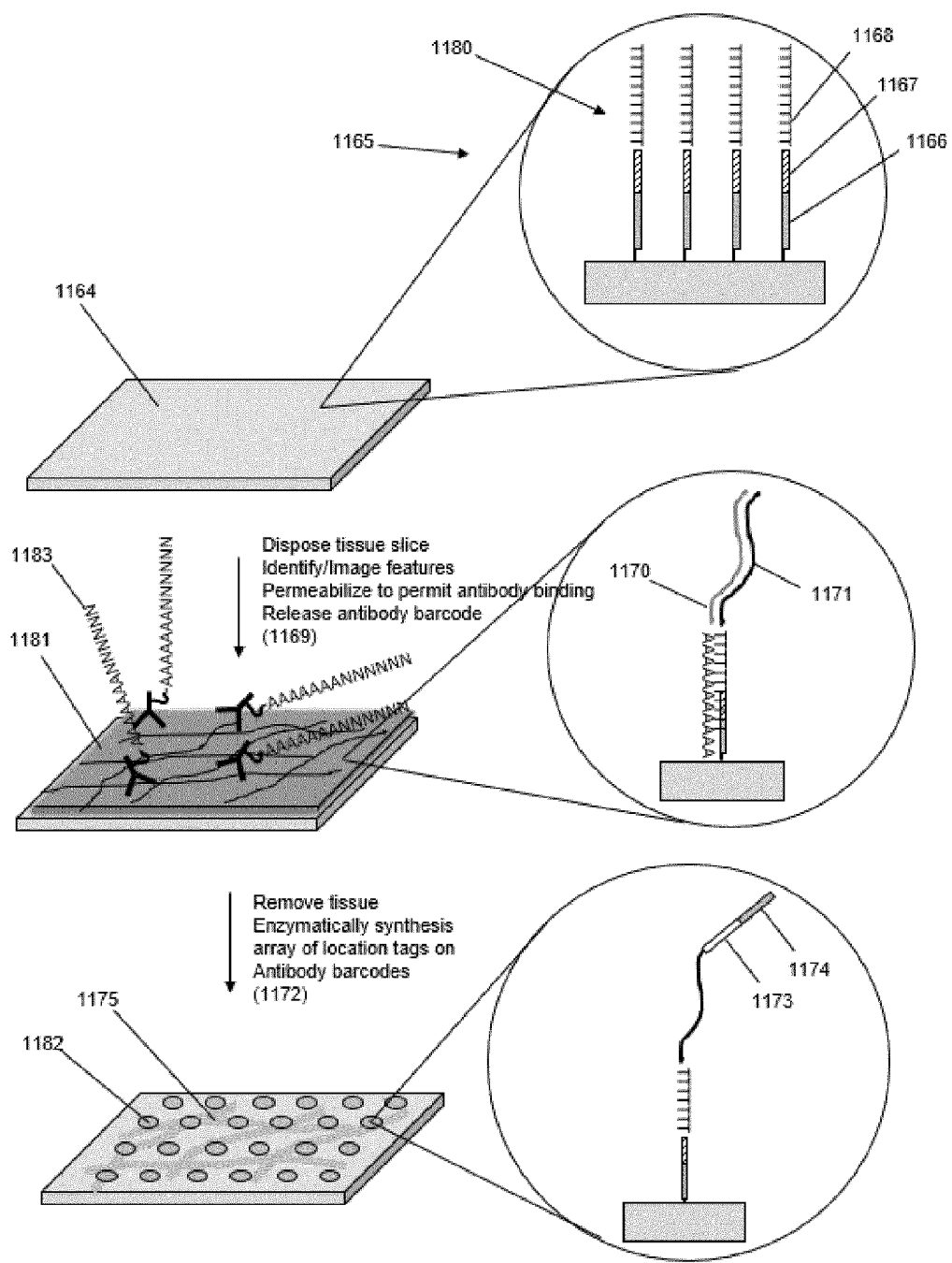
FIG. 1G illustrates an embodiment for identifying spatial distributions of proteins using oligonucleotide labeled antibodies.

Similarly, as illustrated in FIG. 1G, spatial distributions of proteins in a tissue sample may be identified by using antibodies with releasable oligonucleotide barcodes that contain a polyA region and an antibody identification region, that is, an antibody barcode that identifies the protein that the antibody is specific for. In some embodiments, antibodies may carry two tags; an antibody barcode as described above and a fluorescent label which would assist in the optical analysis of the tissue and later correlation of antibody positions with tissue structures or protein distributions of interest. As above, planar array (1164) is provided with a uniform coating of oligonucleotides (1180) attached by their 5' ends, wherein the oligonucleotides (shown in magnified view (1165)) optionally comprise segment (1166), such as a primer binding site, for later amplification and manipulation of an antibody barcode, optional segment (1167) comprising a molecular tag (sometimes referred to as a "unique molecular identifier" or UMI) which facilitates quantification of antibody molecules even after amplification, and segment (1168), such as a polyT segment, which permits capture of antibody barcodes (1183) (SEQ ID NO: 18) released from bound antibodies. Release may be effected by a chemically labile bond in a linker between antibody barcode and the antibody, such as a disulfide moiety. The UMI (1167) may comprise a random nucleotide segment. Different kinds of oligonucleotides, for example, oligonucleotides with different position tags are not required because they are synthesized later using methods of the invention. Segment (1164) may also include a cleavable linker or cleavable nucleotide for releasing antibody barcodes for analysis, such as, by sequencing. Onto array (1164) is disposed a slice or thin layer (1181) (e.g. 100-1000 µm thick) of tissue, which it is then treated (1169) (i) to identify features, such as cells or sub-tissues, of interest and to record and/or correlate such information to locations on planar array (1164), and (ii) to permeablized cells in the tissue so that antibodies can access target proteins and so that released antibody barcodes can diffuse to and be captured by oligonucleotides (1180). The image information is used to define regions on array (1164) within which common position tags are synthesized on antibody barcodes. As above, the position tags allow antibody barcodes to be harvested and sequenced in bulk, yet be related to specific regions by their position tags. After the above steps (i) and (ii), reagents for a reverse transcriptase reaction are applied in order to synthesize complements of the antibody barcodes (1171) just as mRNAs above using captured antibody barcodes (1170) as templates. Tissue slice (1181) is then removed leaving array (1164) with a pattern of different cDNAs attached to its surface. The different cDNAs at the different positions may be identified and quantified by attaching position tags to samples of antibody barcodes from regular locations by inkjet delivery of synthesis reagents for the position tags. As with cDNAs, position tags (1173) on antibody barcodes are selected (e.g. are long enough) to uniquely identify each location or region of interest.

Figure 1H:
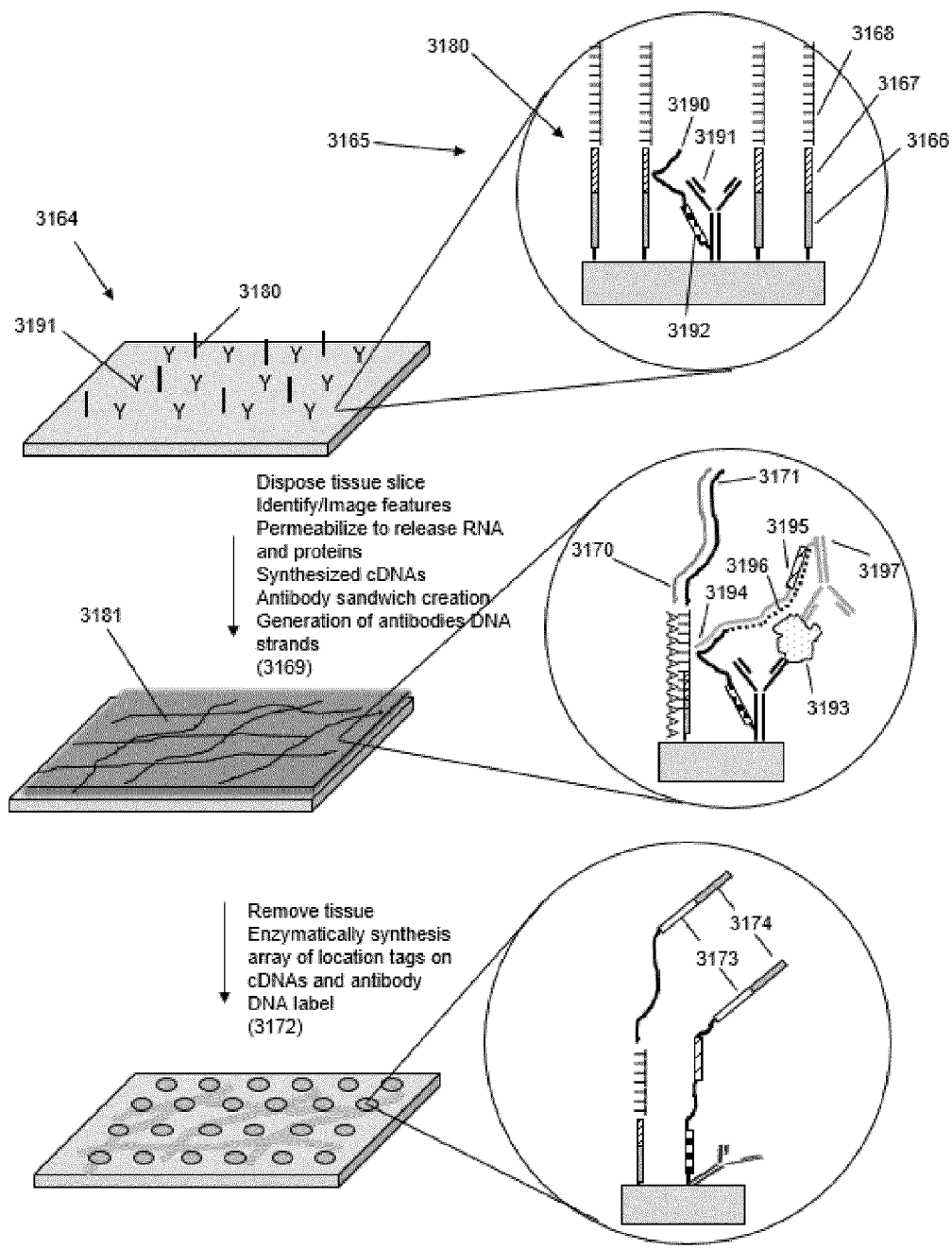
FIG. 1H illustrates an embodiment for identifying both gene expression and protein distribution using immobilized oligonucleotides and antibodies with DNA labels.
Figure 1I:
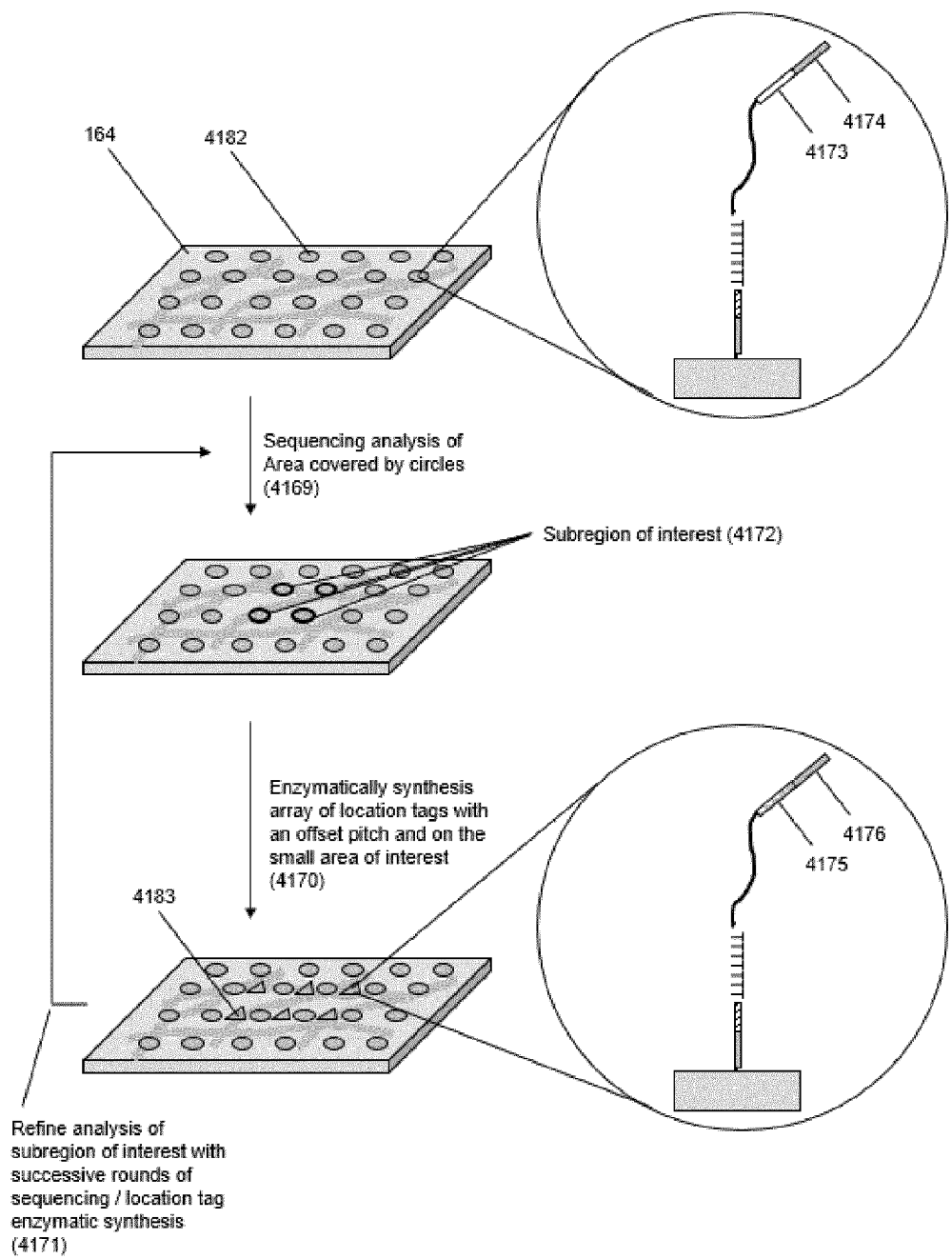
FIG. 1I illustrates an embodiment for focusing the spatial sequencing analysis on a particular surface area of interest through multiple tagging steps.

Similarly, as illustrated in FIG. 1H, spatial patterns of gene expression and distribution of proteins in a tissue slice may be identified by using a planar array comprising a combination of oligonucleotides and DNA labeled antibodies with identifiers, that is, an antibody specific DNA sequence that identifies the protein that the antibody is specific for. Briefly, referring to FIG. 1H, planar array (3164) is provided with an uniform coating of oligonucleotides (3180) attached by their 5' ends, and an uniform coating of antibodies (3191) comprising DNA label (3190) that may be attached to one or more amino acids of antibody (3191). The density of oligonucleotides (3180) and antibodies (3191) of each kind on the planar array (3164) is controlled so that the density of oligonucleotides is predetermined and the density of each kind of antibody (i.e. antibodies with different specificities) is predetermined. As above, oligonucleotides (3180) (shown in magnified view (3165)) comprise segment (3166), such as a primer binding site, for later amplification and manipulation of a cDNA, optional segment (3167) comprising a molecular tag (sometimes referred to as a "unique molecular identifier" or UMI) which facilitates quantification of cDNA molecules even after amplification, and segment (3168), such as a polyT segment, which permits capture of mRNA released from cells. The UMI (3167) may comprise a random nucleotide segment. Antibodies (3191) (shown in magnified view (3165)) comprise a DNA label (3190)(attached to one or more amino acids of the antibody) and segment (3192) comprising a sequence identifier that identifies the protein that the antibody is specific for. Onto array (3164) is disposed a slice or thin layer (3181) (e.g. 100-1000 µm thick) of tissue, which it is then treated (3169) (i) to identify features, such as cells or sub-tissues, of interest and to record and/or correlate such information to locations on planar array (3164), and (ii) to permeabilized cells in the tissue so that mRNA and proteins are released and allowed to diffuse to and be captured by oligonucleotides and antibodies (3180 and 3191, respectively). The image information may be used to define regions on array (3164) within which common position tags are synthesized on cDNAs or antibodies DNA. Treatments may include staining with tissue-specific or biomolecule-specific compounds or dyes. The position tags allow cDNAs and DNA attached to antibodies to be harvested and sequenced in bulk, yet be related to specific regions of the tissue by their position tags. After the above steps (i) and (ii), reagents for a reverse transcriptase reaction are applied in order to synthesize cDNAs (3171) using captured mRNAs (3170) as templates. Binding secondary antibodies (3197) to the same molecules (3193) than immobilized antibodies (3192) are applied to the array in order to form a capture sandwich (like in sandwich ELISA assay). Secondary antibodies (3197) comprise, attached to one or more amino acids, a DNA label (3194), and segment (3195) comprising a sequence identifier that identifies the protein that the antibody is specific for. Identifier segment (3192) of immobilized antibodies (3191) and identifier segment (3195) of secondary antibodies may be the same or different but are associated with and identify the antibody pair that recognize the same protein (3193). In addition, 3' regions of immobilized antibodies' DNA label (3190) and of secondary antibodies' DNA label (3194) are complementary in order to synthesize DNA antibodies strands (3196) during a polymerase elongation step. Tissue slice (3181) is then removed leaving array (3164) with a pattern of different cDNAs and antibodies DNA attached to its surface. The different cDNAs and antibodies DNA at the different positions may be identified and quantified by attaching position tags (3173) and manipulation segments (3174) to samples of cDNAs and antibodies DNA from regular locations by inkjet delivery of synthesis reagents.

FIG. 11 illustrates an embodiment for focusing analysis on a particular surface area (i.e. subregion) of the array (164) that is of particular interest. After following the procedure described by FIG. 1F, a first pass of sequencing analysis (4169) may reveal that a particular surface area (4172) of interest would require better spatial sequencing resolution. A second pass of inkjet delivery of synthesis reagents using the same array but with an offset pitch (4170) is used to generate additional synthesis locations (4183) in the area left untagged by the initial synthesis locations (4182). During this additional tagging step different position tags (4175) are synthesized compared to initial position tags (4173). Additional segments (4174 and 4176) may be added to facilitate manipulation and sequencing of DNA. Interestingly, subsequent passes of inkjet delivery of synthesis reagents on the same array (4171) may be carried over to further refine the analysis by increasing the spatial resolution of the sequencing. Furthermore, this focus analysis method can be applied equally well either to both oligonucleotide arrays (FIG. 1F) or to oligonucleotide and antibodies array (FIG. 1H).

Although FIGS. 1F-1I call for the use of arrays of capture oligonucleotides attached to solid surfaces, methods of the invention permit direct synthesis on tissues without necessarily requiring that analytes of interest, e.g. mRNAs or antibody barcodes, diffuse to and be captured by capture probes attached to an array. In some embodiments, synthesis of position tags may take place directly on a tissue section, with or without prior permeabilization. By way of example, such embodiments may be implemented in the following steps: (a) disposing on a tissue section under binding conditions a plurality of antibodies each capable of specifically binding to a different one of a plurality of proteins, each different antibody having releasably attached an antibody barcode, the antibody barcode comprising an initiator with a free 3'-hydroxyl; (b) repeating for a plurality of cycles at predetermined positions on the tissue section the steps of (i) contacting the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) enzymatically deblocking the elongated fragments to form elongated fragments having free 3'-hydroxyls, thereby synthesizing a different position tag onto the releasably attached antibody barcodes at each different position to form position tag-antibody barcode conjugates; (c) releasing the position tag-antibody barcode conjugates; and (d) sequencing the released position tag-antibody barcode conjugates to determine a spatial distribution of the plurality of proteins in the tissue section. In some embodiments, a step of permeabilizing cells of the tissue section may be included either to expose intracellular protein targets or to synthesize position tags directly on intracellular mRNAs.

Embodiments described in FIGS. 1F-11 may be implemented by the steps: (a) capturing biomolecules from a tissue slice disposed on a solid surface wherein each biomolecule comprises or can be modified to comprise an oligonucleotide identifying the biomolecule captured and having a free 3'-hydroxyl; (b) synthesizing a position tag on the free 3'-hydroxyls of the oligonucleotides at a plurality of different positions on the solid surface by template-free enzymatic synthesis; and (c) sequencing the oligonucleotides to determine a spatial distribution of biomolecules in the tissue slice. In some embodiments, a further step of releasing the oligonucleotides in implemented using conventional linking chemistries and protocols, e.g. described in the above-cited references. In some embodiments, biomolecules are polynucleotides, such as mRNA, RNA, antibody barcodes, proteins, or the like. Biomolecules may be captured by complementary oligonucleotides attached to the solid surface or antibodies attached to the solid surface. In the later case, antibody binding pairs (such as used in ELISAs) may be applied to a solid surface after capture of protein biomolecules. In some embodiments, either one or both antibodies of a binding pair may have oligonucleotide barcodes to which position tags may be synthesized.

Figure 2A:
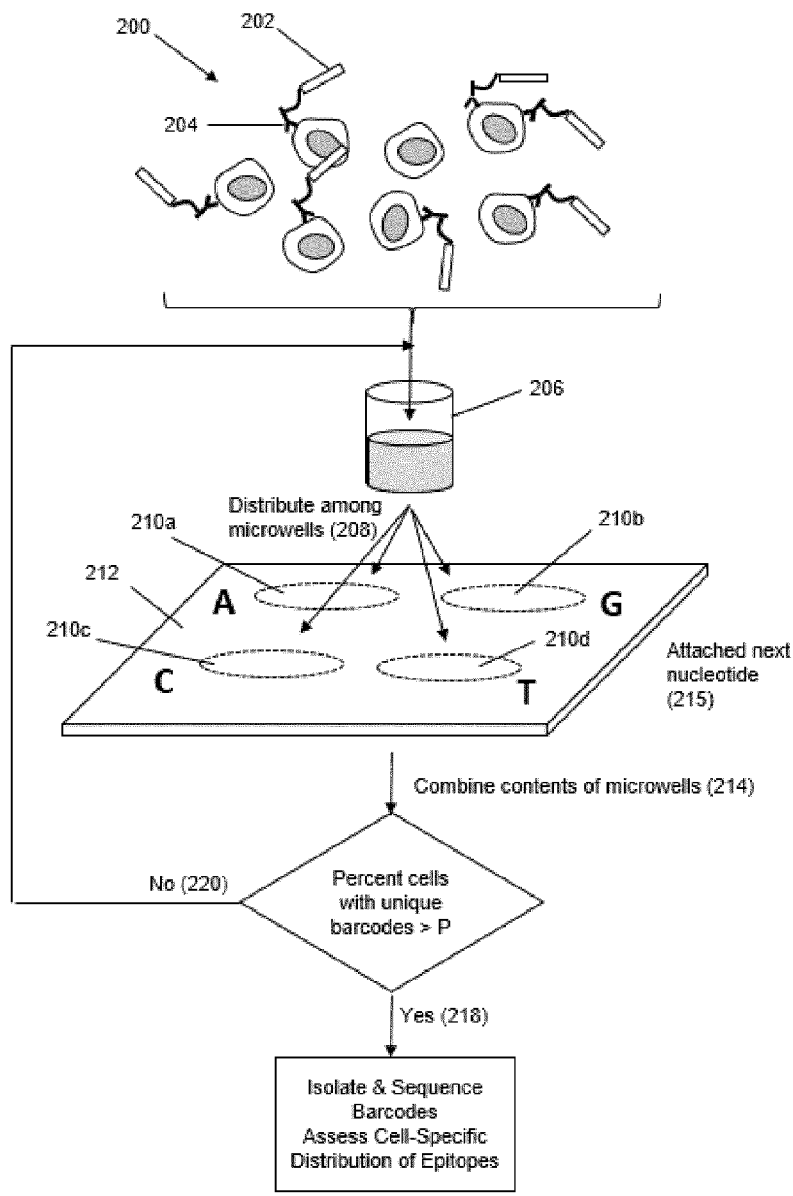
FIGS. 2A-2D illustrate embodiments of the invention for directly synthesizing oligonucleotide tags on living cells or fixed and permeabilized cells.
Figure 2B:
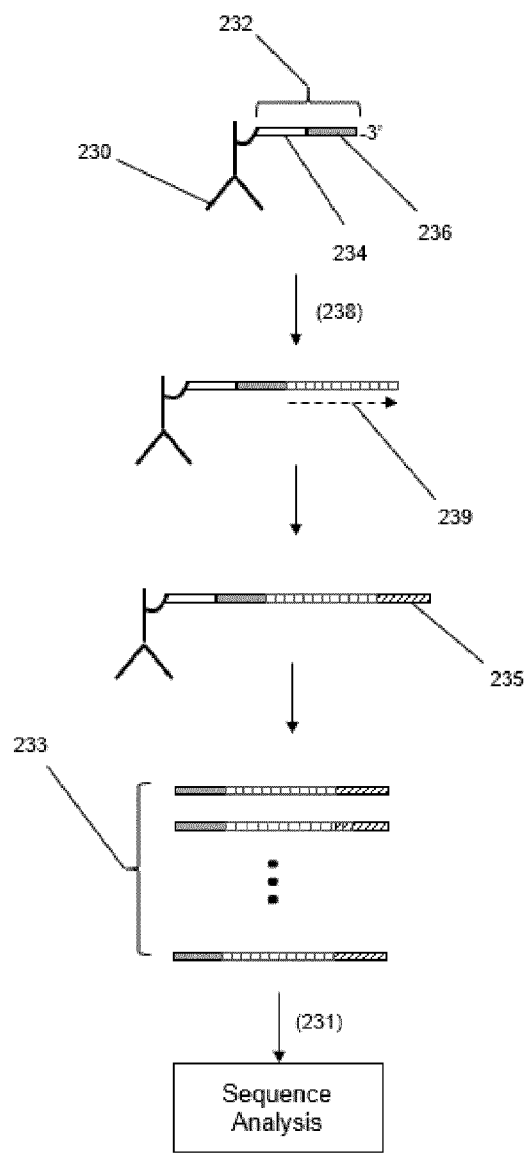

FIGS. 2A-2D illustrate the above concepts for embodiments in which expression of selected proteins (or epitopes) is measured using specific antibody binding compounds and expression of either all or selected genes is measured using primers specific for all mRNAs or selected mRNAs. In both classes of probe, the attached oligonucleotide label may identify the compound it specifically binds to as well as serve as an initiator for enzymatic synthesis. FIG. 2A illustrates an embodiment for implementing a process of "split and mix" tag synthesis. A population of viable cells (200) is combined with a set of antibodies (204) each labeled with oligonucleotides (202) which both identify the antibody (and therefore its target protein) and serves as an initiator. Cells (200) are combined in a common vessel (206) and then distributed (usually in equal parts) to multi-well array (212) and into one of four wells 210a-210d in which one enzymatic elongation cycle is carried out, for example, one A extension in 210a, one G extension in 210b, one C extension in 210c, and one T extension in 210d. After deblocking the added nucleotide, the cells (200) are harvested and combined again in a common vessel (206). A random nucleotide tag of increasing length is generated with each nucleotide addition, so that with the n additions 4' tags are generated. To minimize the manipulation and possible damage to cells, if the size of population (200) is known, then the number of cycles may be limited to a number that insures a high probability of cells having unique tags, but that minimizes cell damage or loss. For example, if population (200) consisted of $10^6$ cells then 10-11 cycles generates $1-4\times10^6$ unique tags. In some embodiments, a number of cycles are implements to ensure that each cell carries a unique oligonucleotide tag with a probability of 99 percent or higher. In some embodiments, once a number of cycles has been implemented to give substantially all cells a unique oligonucleotide tag (218), then the tags may be harvested and analyzed by large-scale sequencing (and, for example, the expression of each protein and each gene in each cell can be tabulated). As illustrated in FIG. 2B, the initial oligonucleotides attached to either antibodies or primers may include other segments for molecular manipulation. For example, oligonucleotide (232) on antibody (230) may comprise segment (234) which may include a code for identifying the specificity of antibody (230) as well as further sequences for later manipulation, such as for PCR amplification. Oligonucleotide (232) also includes segment (236) having a free 3'-hydroxyl which serves as an initiator for an initial cycle of nucleotide addition. After a number of cycles is carried out to attached tag nucleotides (238 and 239), further nucleotides may be added with no splitting or mixing in order to attached a common segment (235), e.g. a primer sequence, to permit manipulation and analysis of the tags and protein or gene identification sequences. In some embodiments, this may be accomplished by amplifying the attached oligonucleotides to form amplicon (233) which then may be analyzed (231) by high throughput DNA sequencing.

As mentioned above, cells may be labeled with a similar random barcode that, instead of consisting of a random sequence of nucleotides, consists of a random sequence of homopolymer segments, wherein each homopolymer segment comprises a different kind of nucleotide than that of a nearest neighbor homopolymer segment. The advantage of such a barcoding scheme is that 3'-blocked dNTPs do not have to be used; therefore, no deblocking step is required, which makes the synthesis process simpler and potentially less damaging to the viability of the cells. The lengths of homopolymer segments used in such barcodes may vary widely. In some embodiments, conditions including the duration of reaction are selected so that the average length of a homopolymer segment is in the range of from 1 to 100 nucleotides; in other embodiments, the average length of a homopolymer segment is in the range of from 1 to 25 nucleotides; and in still other embodiments, the average length of a homopolymer segment is in the range of from 1 to 10 nucleotides.

Figure 2C:
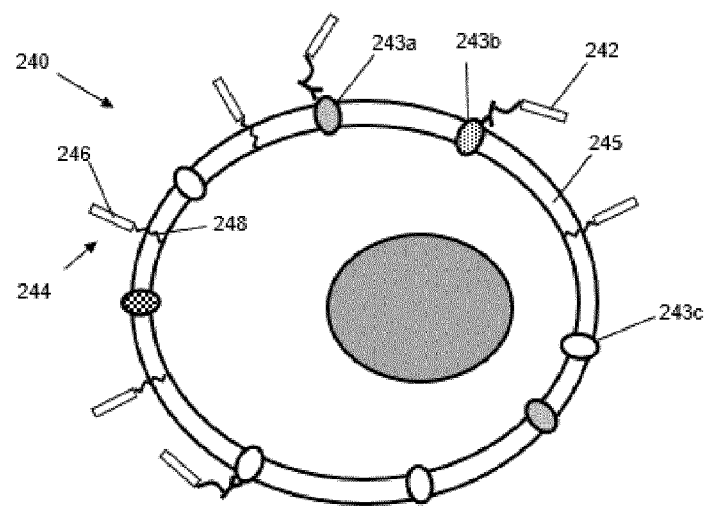
Figure 2D:
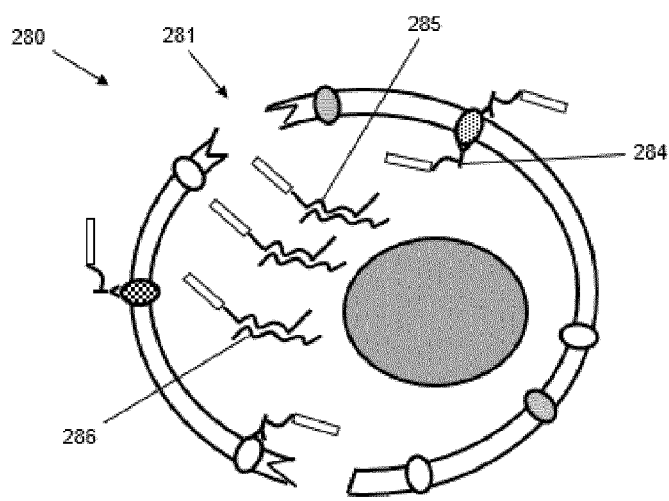

Binding compounds used with the invention may include a wide variety of compositions that specifically bind to predetermined cellular constituents and to which initiators may be attached for generating identifying oligonucleotides. FIGS. 2C and 2D illustrate the range of different types of binding compounds that may be used with viable cells (FIG. 2C) and with cells that have been fixed and permeabilized (FIG. 2D) to give access to intracellular constituents. Usually only cellular antigens and/or constituents exposed to the extracellular environment are accessible in viable cells (240). Thus, in some embodiments, binding compounds comprise antibody binding compounds labeled with initiator oligonucleotides (242) as described above, which antibody is specific for predetermined cell surface proteins (e.g. 243a, 243b, 243c), or membrane probes (244), which comprise a membrane-specific component (248) that inserts in cell surface membrane (245), such as a lipophilic moiety, and an iinitiator oligonucleotide (246). As illustrated in FIG. 2D, fixed and permeabilized cells (280) provide access through pores (281) created in a permeabilization step, to intracellular RNA (286) and intracellular proteins (284), to which binding compounds comprising hybridization probes (e.g. 285) and antibody binding compounds (287), respectively, may be targeted. In some embodiments, binding compounds may comprise hybridization probes of genomic DNA.

In some embodiments, initiator oligonucleotides with free 3'-hydroxyls are stably inserted into to the cell surface membranes of target cells by derivatizing the 5' end of initiator oligonucleotides with a lipophilic moiety using conventional techniques, e.g. as disclosed in the following references: Weber et al, Biomacromolecules, 15: 4621-4626 (2014); Bunge et al, Langmuir, 23(8): 4455-4464 (2007); Borjesson et al, J. Amer. Chem. Soc., 131(8): 2831-2839 (2009); Bunge et al, J. Phys. Chem. B, 113(51): 16425-16434 (2009); and like references. Of particular interest is the technique disclosed by Weber (cited above) which calls for the insertion of complementary pairs of oligonucleotides each derivatized with a lipophilic moiety, one oligonucleotide of the pair on its 5' end (a longer initiator oligonucleotide) and the other on its 3' end (a shorter support oligonucleotide). The hybridized pairs are very stable in the cell membrane, which would minimize losses during synthesis.

Figure 3A:
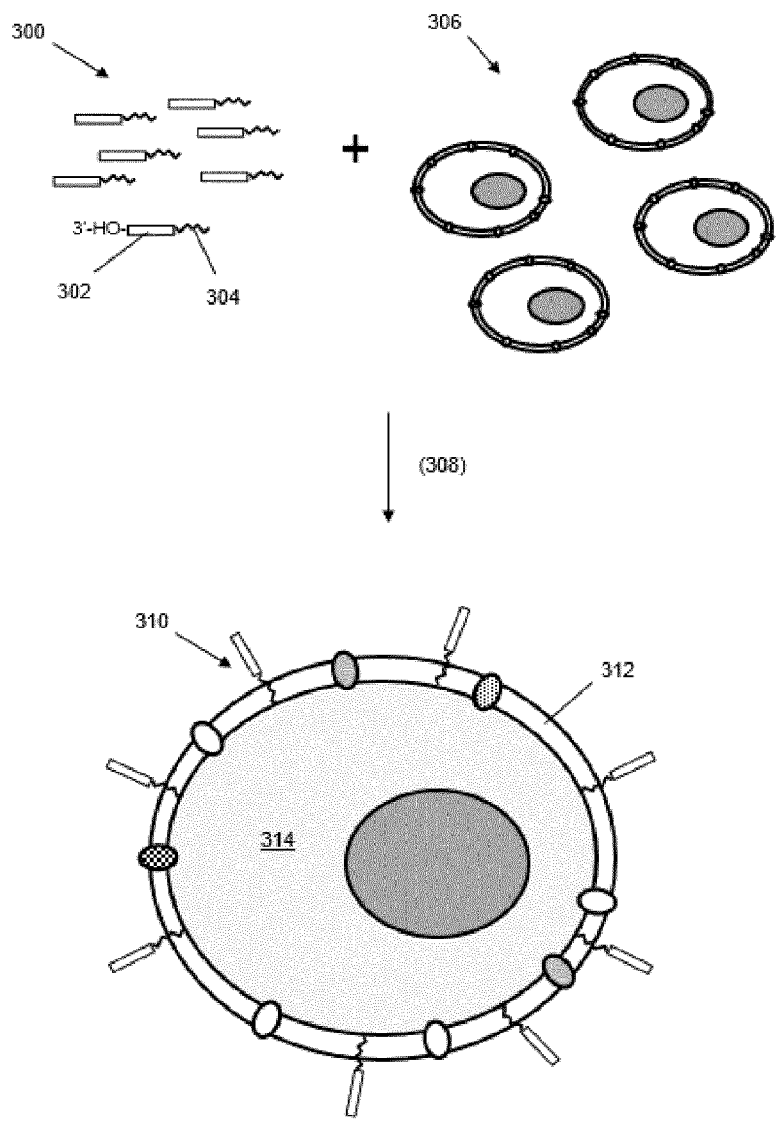
FIG. 3A illustrates attachment of initiator oligonucleotides onto a cell surface membrane by a lipophilic anchor.

As illustrated in FIG. 3A, in some embodiments, initiator oligonucleotides (300) comprise oligonucleotide (302) with a free 3' hydroxyl and lipophilic moiety (304) at a 5' end. Such initiator is capable of stably inserting into the lipid bilayer of a cell surface membrane with a free 3'-hydroxyl available for extension. Initiator oligonucleotides (300) are combined with target cells (306) under conditions (308) that permit initiator oligonucleotides (300) to insert (310) into cell surface membrane (312) by their lipophilic moieties so that free 3'-hydroxyls of the oligonucleotides are accessible for synthesis. Cells (314) may then be subjected to enzymatic extension of initiators (310) by methods of the invention.

Figure 3B:
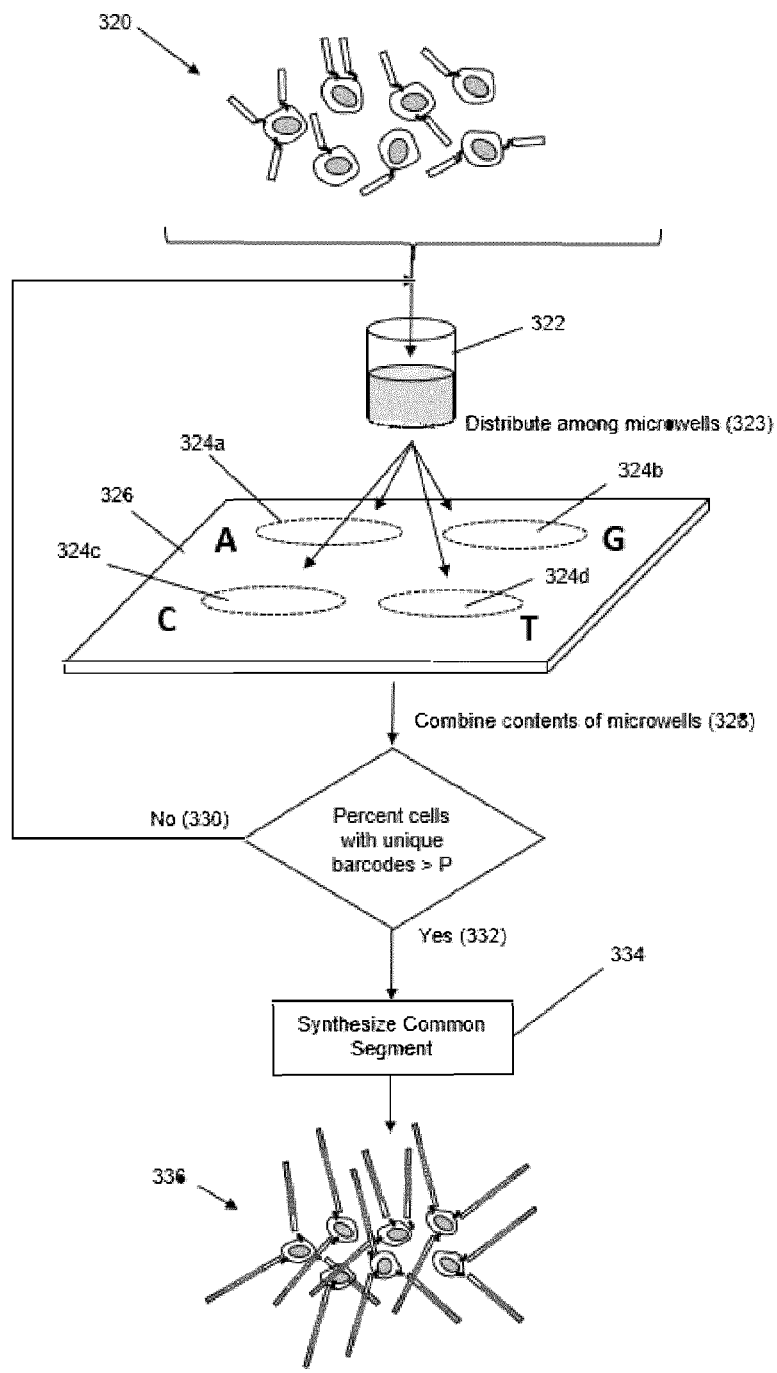
FIG. 3B illustrates the "split and mix" synthesis of unique molecular barcodes on initiators anchored in the cell surface membranes of cells.
Figure 3C:
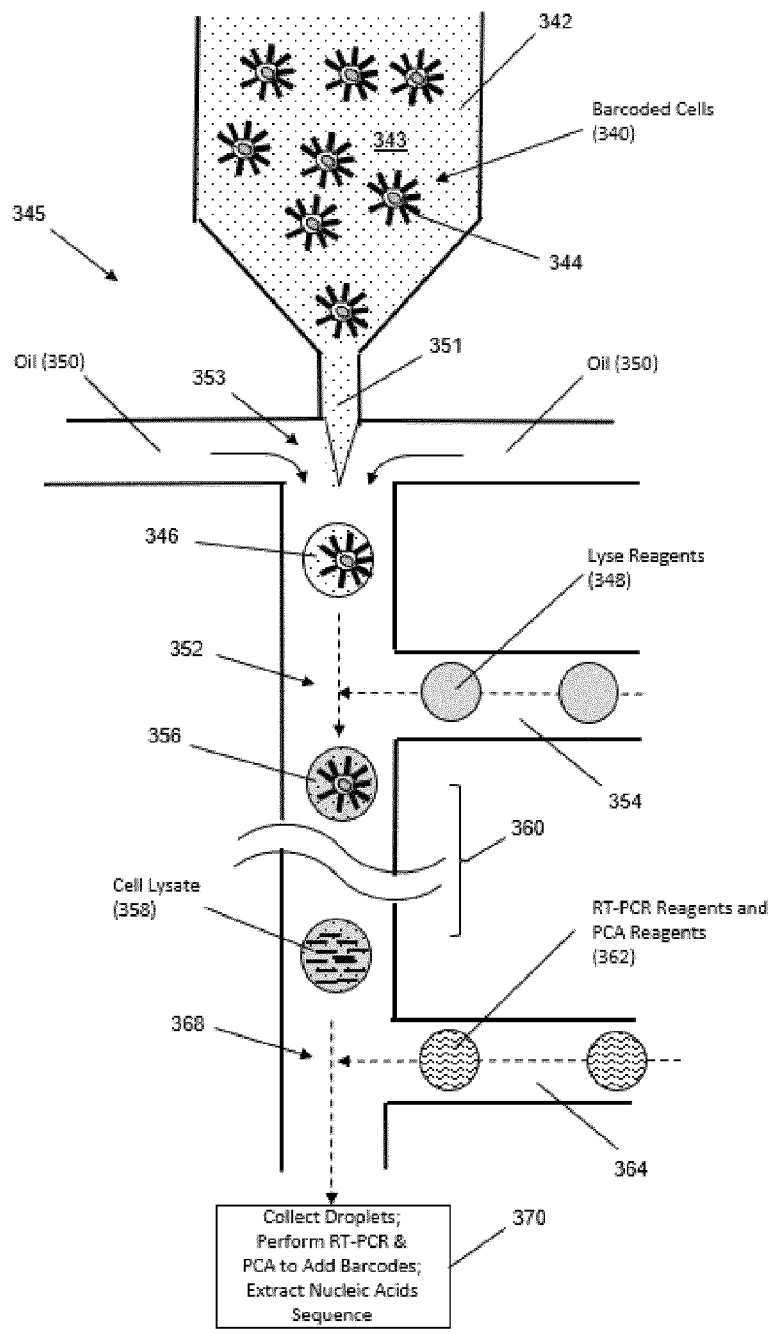
FIG. 3C illustrates microfluidics processing of barcoded cells to generate single-cell specific cDNA libraries where each library includes a cell-specific barcode.

In some embodiments, enzymatic extension of initiators (310) may be employed to generate unique cell-specific barcodes on cells (314) by a "split and mix" synthesis strategy, as illustrated in FIG. 3B. Cells with initiators are pooled in vessel (322) after which successive cycles of nucleotide additions are carried out. Cells in vessel (322) are distributed (323) among four reaction chambers (324a-324d) in which is added to free 3'-hydroxyl of an attached initiator a 3'-O-blocked dA, dG, dC or dT, respectively, after which such added nucleotide is de-blocked to ready it for the next addition cycle. In some embodiments, cells of vessel (322) are distributed equally among the for reactions chambers; however, in alternative embodiments, cells of vessel (322) may be distributed non-equally among reaction vessels (234a-324d) to bias the occurrence of a nucleotide at a particular position. In other embodiments, more than one addition cycle may be carried out in the reaction chambers (324a-324d), thereby, for example, adding two or more nucleotides. Reaction chambers (324a-324d) are illustrated as wells in a solid structure (326), but they may comprise separate reaction vessels, such as separate reaction tubes. In some embodiments, reaction chambers (324a-324d) may comprise wells in conventional microwell plates of 24-, 48-, 96-, 384- or 1536-wells. In higher capacity microwell plates, e.g. 96-well, multiple syntheses may be carried out in parallel, for example, for barcoding and analyzing multiple samples at the same time. In some embodiments, after a cycle of nucleotide addition and deprotection, cells in chambers (324a-324d) are mixed (328) so that in the next nucleotide addition step each cell of the mixture has an equal probability of having added an A, C, G or T. In such embodiments, by such "split and mix" steps, a unique random sequence oligonucleotide may be generated on the initiators anchored in the cell membranes. Such "split and mix" steps may be continued (330) until an added random-sequence oligonucleotide is long enough for each cell of the population in vessel (322) is associated with a unique sequence. In some embodiments, after unique barcodes are formed (332), additional nucleotides of a common sequence may be synthesized without splitting and mixing. Such common sequences may include primer binding sites, or the like, for manipulating or amplifying the barcodes for later analysis. The resulting barcoded cells (336) may then be used in applications, such as single-cell transcriptome analysis, as illustrated in FIG. 3C. Guidance for large scale single cell transcriptome analysis with bead-based barcoding is disclosed in the following references: Kolodziejczyk et al, Molecular Cell, 58: 610-620 (2015); Saliba et al, Nucleic Acids Research, 42(14): 8845-8860 (2014); Church et al, U.S. patent publication 3013/0274117; Macosko et al, Cell, 161: 1202-1214 (2015); Klein et al, Cell, 161: 1187-1201 (2015); and the like. Generally, the techniques comprise steps of (i) capturing or isolating single cells, (ii) lysing single cells, (iii) reverse transcribing RNA to make cDNA, (iv) amplification of cDNAs, and (v) sequencing. Such techniques may further include a step of attaching cell-specific barcodes to cDNAs, in particular by generating droplets containing a single cell and a single barcode-carrying bead.

In some embodiments, unique oligonucleotide tags may be synthesized on viable cells by attaching tags comprising sequences of homopolymeric segments. In some embodiments, the invention is directed to methods of synthesizing on a viable cell an oligonucleotide barcode comprising the steps of: (a) providing an initiator with a free 3'-hydroxyl attached to a cell surface molecule of the cell or anchored in a cell surface membrane of the cell; (b) repeating under biological conditions a plurality of cycles of the step of contacting under elongation conditions the initiator or elongated fragments having free 3'-O-hydroxyls with a nucleoside triphosphate and a template-independent DNA polymerase so that the initiator or elongated fragments are elongated by a homopolymer segment to form elongated fragments having free 3'-hydroxyls, wherein the kind of nucleoside triphosphate added in each step after a first step is different from the kind in the immediately preceding step. In some embodiments, each of the cycles further includes a step of removing unincorporated nucleoside triphosphates. In some embodiments, the elongation conditions include a concentration of said nucleoside triphosphates, a temperature and a reaction time to produce homopolymer segments having an average length in the range of from 1 to 100 nucleotides. In some embodiments, unique oligonucleotide tags comprising homopolymeric segments are produced using a split-and-mix procedure.

Single Cell Analysis

In some embodiments of the invention, cells from a population are disposed in reactors each containing a single cell. This may be accomplished by a variety of large-scale single-cell reactor platforms known in the art, e.g. Clarke et al, U.S. patent publication 2010/0255471; Mathies et al, U.S. patent publication 2010/0285975; Edd et al, U.S. patent publication 2010/0021984; Colston et al, U.S. patent publication 2010/0173394; Love et al, International patent publication WO2009/145925; Muraguchi et al, U.S. patent publication 2009/0181859; Novak et al, Angew. Chem. Int. Ed., 50: 390-395 (2011); Chen et al, Biomecl Microdevices, 11:1223-1231 (2009); and the like, which are incorporated herein by reference. In one aspect, cells are disposed in wells of a microwell array where reactions, such as PCA reactions, take place; in another aspect, cells are disposed in micelles of a water-in-oil emulsion, where micelles serve as reactors. Micelle reactors generated by microfluidics devices, e.g. Mathies et al (cited above) or Edd et al (cited above), are of particular interest because uniform-sized micelles may be generated with lower shear and stress on cells than in bulk emulsification processes. Compositions and techniques for emulsifications, including carrying out amplification reactions, such as PCRs, in micelles is found in the following references, which are incorporated by reference: Becher, "Emulsions: Theory and Practice," (Oxford University Press, 2001); Griffiths and Tawfik, U.S. Pat. No. 6,489,103; Tawfik and Griffiths, Nature Biotechnology, 16: 652-656 (1998); Nakano et al, J. Biotechnology, 102: 117-124 (2003); Dressman et al, Proc. Natl. Acad. Sci., 100: 8817-8822 (2003); Dressman et al, U.S. Pat. No. 8,048,627; Berka et al, U.S. Pat. Nos. 7,842,457 and 8,012,690; Diehl et al, Nature Methods, 3: 551-559 (2006); Williams et al, Nature Methods, 3: 545-550 (2006); Zeng et al, Analytical Chemistry, 82(8): 3183-3190 (2010); Micellul a DNA Emulsion & Purification Kit instructions (FITRx, Gdansk, Poland, 2011); and the like. In one embodiment, the mixture of homogeneous sequence tags (e.g. beads) and reaction mixture is added dropwise into a spinning mixture of biocompatible oil (e.g., light mineral oil, Sigma) and allowed to emulsify. In another embodiment, the homogeneous sequence tags and reaction mixture are added dropwise into a cross-flow of biocompatible oil. The oil used may be supplemented with one or more biocompatible emulsion stabilizers. These emulsion stabilizers may include Atlox 49I 2, Span 80, and other recognized and commercially available suitable stabilizers. In some embodiments, the emulsion is heat stable to allow thermal cycling, e.g., to at least 94° C., at least 95° C., or at least 96° C. In some embodiments, the droplets formed range in size from about 5 microns to about 500 microns. In some embodiments, droplets are formed in a range of from about 10 microns to about 350 microns, or from about 50 to 250 microns, or from about 100 microns to about 200 microns. Advantageously, cross-flow fluid mixing allows for control of the droplet formation, and uniformity of droplet size.

In some embodiments, micelles are produced having a uniform distribution of volumes so that reagents available in such reactors result in similarly amplified target nucleic acids and sequence tags. That is, widely varying reactor volumes, e.g. micelle volumes, may lead to amplification failures and/or widely varying degrees of amplification. Such failures and variation would preclude or increase the difficulty of making quantitative comparisons of target nucleic acids in individual cells of a population, e.g. differences in gene expression. In one aspect, micelles are produced that have a distribution of volumes with a coefficient of variation (CV) of thirty percent or less. In some embodiments, micelles have a distribution of volumes with a CV of twenty percent of less.

Cells of a sample and homogeneous sequence tags may be suspended in a reaction mixture prior to disposition into reactors. In one aspect, a reaction mixture is a PCA reaction mixture and is substantially the same as a PCR reaction mixture with at least one pair of inner (or linking) primers and at least one pair of outer primers. A reaction mixture may comprise one or more optional components, including but not limited to, thermostable restriction endonucleases; one or more proteinase inhibitors; lysing agents to facilitate release of target nucleic acids of isolated cells, e.g. Brown et al, Interface, 5: 5131-5138 (2008); and the like. In some embodiments, a step of lysing cells may be accomplished by heating cells to a temperature of 95° C. or above in the presence of a nonionic detergent, e.g. 0.1% Tween X-100, for a period prior to carrying out an amplification reaction. In one embodiment, such period of elevated temperature may be from 10-20 minutes. Alternatively, a step of lysing cells may be accomplished by one or more cycles of heating and cooling, e.g. 96° C. for 15 min followed by 10° C. for 10 min, in the presence of a nonionic detergent, e.g. 0.1% Tween X-100. In some embodiments, micelle reactors are generated and sorted in a microfluidics device as described more fully below.

Single Cell Transcriptome Analysis

In FIG. 3C, for some embodiments, barcoded cells (340) may be prepared for transcriptome analysis using a droplet-based microfluidic device (345), which encapsulates barcoded single cells into aqueous micelles and coalesces the cell-containing micelles with a series of micelles containing reagents for constructing cDNA libraries. Alternatively, cell-containing micelles may be produced and reagents delivered to such micelles using non-microfluidic methods such as disclosed in Abate et al, International patent publication WO2019/139650. Cells (340) with initiator-barcode conjugates (344) embedded in their cell surface membranes are disposed in chamber (343) in aqueous solution (342) which may have a pH, salt concentrations and other necessary ingredients to maintain the integrity of the cells. From chamber (343) cells (340) and aqueous solution (342) are driven through passage (351) into junction (353) where confluent oil flows (350) cause the formation of aqueous micelle (346), some of which contain a single cell. Such droplet-based microfluidics devices may be constructed using well-known designs and techniques. For example, the following references provide guidance in the design and implementation of such microfluidic devices: Zare et al, Ann. Rev. Biomed. Eng., 12: 187-201 (2010); Link, U.S. patent publication 2012/0309002; Shapiro et al, Nature Reviews Genetics, 14: 618-630 (2013); Kim et al, Anal. Chem., 90: 1273-1279 (2018); Abate et al, U.S. patent publication 2017/0009274; Zagnoni et al, chapter 2, Methods in Cell Biology, 102: 25-48 (2011); Zheng et al, Nature Comm., 8:14049 (2016); Link et al, U.S. patent publication 2008/0014589; and the like.

Cell-containing micelle (346) is caused to coalesce with reagent micelle (348) in oil flow (354) at junction (352). Reagent micelle (348) contains lysis reagents for breaking down the cell surface membrane to expose mRNA for transcription and amplification. The result of such coalescence is micelle (356), which incubates during flow through passage (360) whose length is designed to provide a transit time sufficient for the lysis reagents carried by micelle (348) to complete lysis of the cell and produce a cellular lysate (358) ready for reverse transcription and amplification. Lysis reagents are described in the following references: Tang et al, Nature Protocol, 5(3): doi:10.1038/nprot.2009.236; Thronhill et al, Prenatal Diagnosis, 21: 490-497 (2001); Kim et al, Fertility and Sterility, 92: 814-818 (2009); and the like. Exemplary lysis conditions for use with PCA reactions are as follows: 1) cells in H2O at 96° C. for 15 min, followed by 15 min at 10° C.; 2) 200 mM KOH, 50 mM dithiotheitol, heat to 65° C. for 10 min; 3) for 4 µL protease-based lysis buffer: 1 µL of 17 µM SDS combined with 3 µL of 125 µg/mL proteinase K, followed by incubation at 37° C. for 60 min, then 95° C. for 15 min (to inactivate the proteinase K); 4) for 10 µL of a detergent-based lysis buffer: 2 µL H2O, 2 µL 250 ng/4 polyA, 2 µL 10 mM EDTA, 2 µL 250 mM dithiothreitol, 2 µL 0.5% N-laurylsarcosin salt solution. Single-cell analysis platforms, incubation times, lysis buffer and/or PCA reaction other components, their concentrations, reactions volumes and the like, are design choices that are optimized for particular applications by one of ordinary skill in the art. In one embodiment, an alkaline lysis buffer disclosed by Kim et al, Anal. Chem., 90: 1273-1279 (2018) is employed. Such buffer comprises 20 mM NaOH, 60% (v/v) PeG-200, and 2% (v/v) Triton X-100, and may be neutralized by the buffering capacity of an RT-PCR reagents.

Figure 4A:
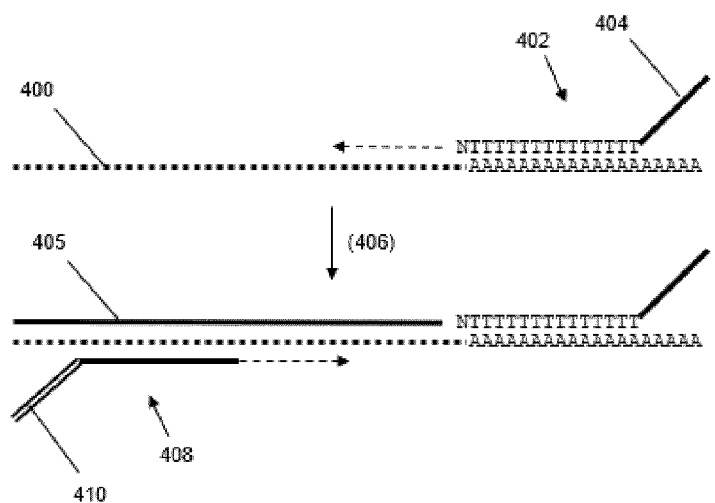
FIG. 4A illustrates a procedure for amplifying specific genes from single cells.
Figure 4B:
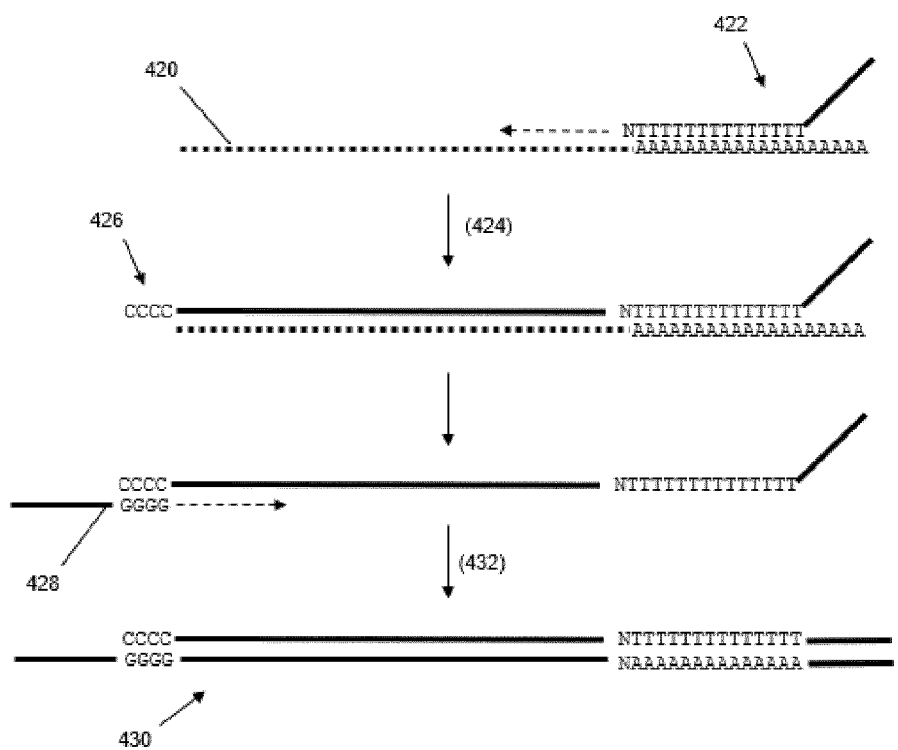
FIG. 4B illustrates a procedure (template switching) for amplifying a full cDNA library from single cells.

After lysis, cell lysate in micelle (358) is coalesced at junction (368) with reagent micelle (362) from oil flow (364). Reagent micelle contains reverse transcriptase and PCR reaction components. In some embodiments, such components may comprise ingredient from a commercial RT-PCR kit, for example, ThermoFisher Invitrogen SuperScript IV One-Step RT-PCR system. In some embodiments, such components may comprise template-switching transcription components, e.g. Trombetta et al, Curr. Protocol Mol. Biol., 107: 4.22.1-4.22.17 (2014). After coalescence, droplets are collected in a temperature-control device, such as a thermocycler, which permits heat denaturation of reverse transcriptase and subsequence PCR of cDNAs and barcodes. Different embodiments of reverse transcription reactions are illustrated in FIGS. 4A and 4B. In FIG. 4A, polyT primer (402) is anneal to mRNA (400) and extended (406) to form a first DNA strand (405) (SEQ ID NO: 17). After removal of mRNA template (400), gene-specific primer (408) is annealed and extended to complete the cDNA. Primer (408) may comprise 5' tail (410) which includes common sequences, such as primer binding sites, for later manipulation and preparation for sequencing. In FIG. 4B, a template-switching scheme is illustrated which may be used for producing a single cell cDNA library, e.g. Zhu et al, Biotechniques, 30(4): 892-897 (2001). Template (422) is anneal to mRNA (420) and extended (424) with a reverse transcriptase, such as MMLV, that make template-free additions of a selected nucleotide (426) to the 3' end of the first cDNA strand after the end of the RNA template is reached. This allows adaptor ((428) to anneal to the template-free addition and be extended (432) to produce a second strand to complete cDNA (430). The 5' segment of adaptor (428) may be designed to include common sequences for later amplification and preparation for high throughput sequencing.

In some embodiments, after template-switching reverse transcription, polymerase cycling assembly reactions are carried out in each micelle. Polymerase cycling assembly (PCA) reactions permit a plurality of nucleic acid fragments to be fused together to form a single fusion product in one or more cycles of fragment annealing and polymerase extension, e.g. Xiong et al, FESS Micro biol. Rev., 32: 522-540 (2008). PCA reactions come in many formats. In one format of interest. PCA follows a plurality of polymerase chain reactions (PCRs) taking place in a common reaction volume, wherein each component PCR includes at least one linking primer that permits strands from the resulting amplicon to anneal to strands from another amplicon in the reaction and to be extended to form a fusion product or a precursor of a fusion product. PCA in its various formats (and under various alternative names) is a well-known method for fragment assembly and gene synthesis, several forms of which are disclosed in the following references: Yon et al, Nucleic Acids Research, 17: 4895 (1989); Chen et al, J. Am. Chem. Soc., 116: 8799-8800 (1994); Stemmer et al, Gene, 164: 49-53 (1995); Hoover et al, Nucleic Acids Research, 30: c43 (2002); Xiong et al, Biotechnology Advances, 26: 121-134 (2008); Xiong et al, FEBS Microbiol. Rev., 32: 522-540 (2008); and the like.

Figure 4C:
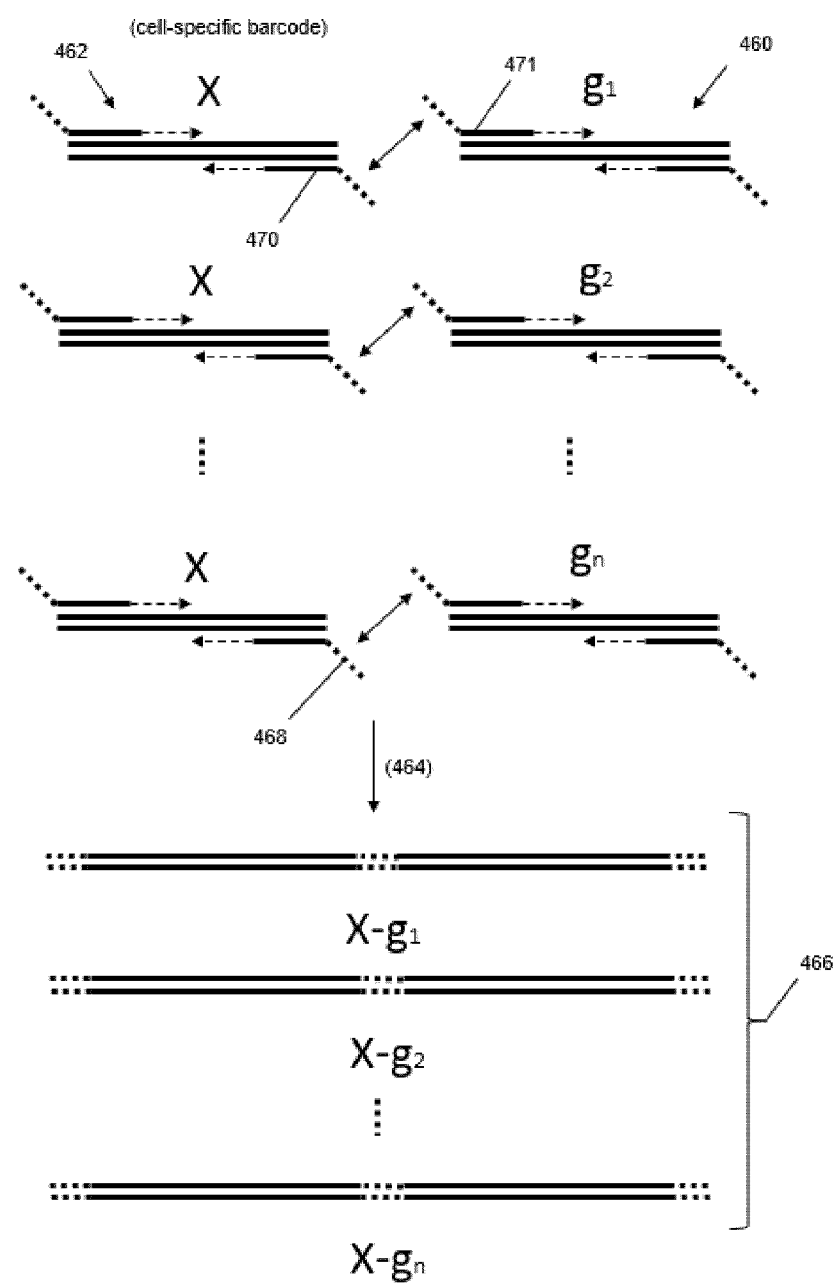
FIG. 4C illustrates a procedure for attaching cell-specific barcodes to cDNA sequences by polymerase cycling amplification (PCA).

FIG. 4C illustrates the use of PCA to attach the same cell-specific barcode to each cDNA. "X" DNAs (462) may be the enzymatically synthesized barcode sequences flanked by primer binding sites. Primers (470) and (471) anneal to common sequences on the barcodes and cDNAs, respectively, and they have complementary 5' tails.

Multiple different target nucleic acids, such as cDNAs (460), $g_1, g_2 \ldots g_n$, are linked to the same barcode nucleic acid, X (462) to form (464) multiple fusion products $X\text{-}g_1$, $X\text{-}g_2$, X-gK (566). In some embodiments, such plurality is between 2 and 10000; and in another embodiment, it is between 2 and 1000; and in another embodiment, it is between 2 and 100. In PCA reactions of these embodiments, the concentration of inner primer (468) may be greater than those of inner primers (e.g. 471) of the various gi nucleic acids so that there is adequate quantities of the X amplicon to anneal with the many stands of the gi amplicons. In accordance with a method of the invention, the fusion products (466) may be extracted from the reaction mixture of the coalesced micelles and sequenced.

In some embodiments, a method for generating a cDNA library with cell-specific barcodes may comprise the steps of (a) synthesizing a unique oligonucleotide barcode on each cell of a population to form a population of barcoded cells; (h) disposing barcoded cells into multiple reactors each containing a single barcoded cell in a polymerase cycling assembly (PCA) reaction mixture, wherein the PCA reaction mixture comprises a pair of outer primers and one or more pairs of linking primers specific for a plurality of target nucleic acids in the barcoded cells and the oligonucleotide barcodes; (c) performing a PCA reaction in the reactors so that fusion products of the target nucleic acids and the oligonucleotide barcodes are formed in the reactors; and (d) sequencing the fusion products from the reactors to identify the target nucleic acids of each cell in the population.

Figure 5:
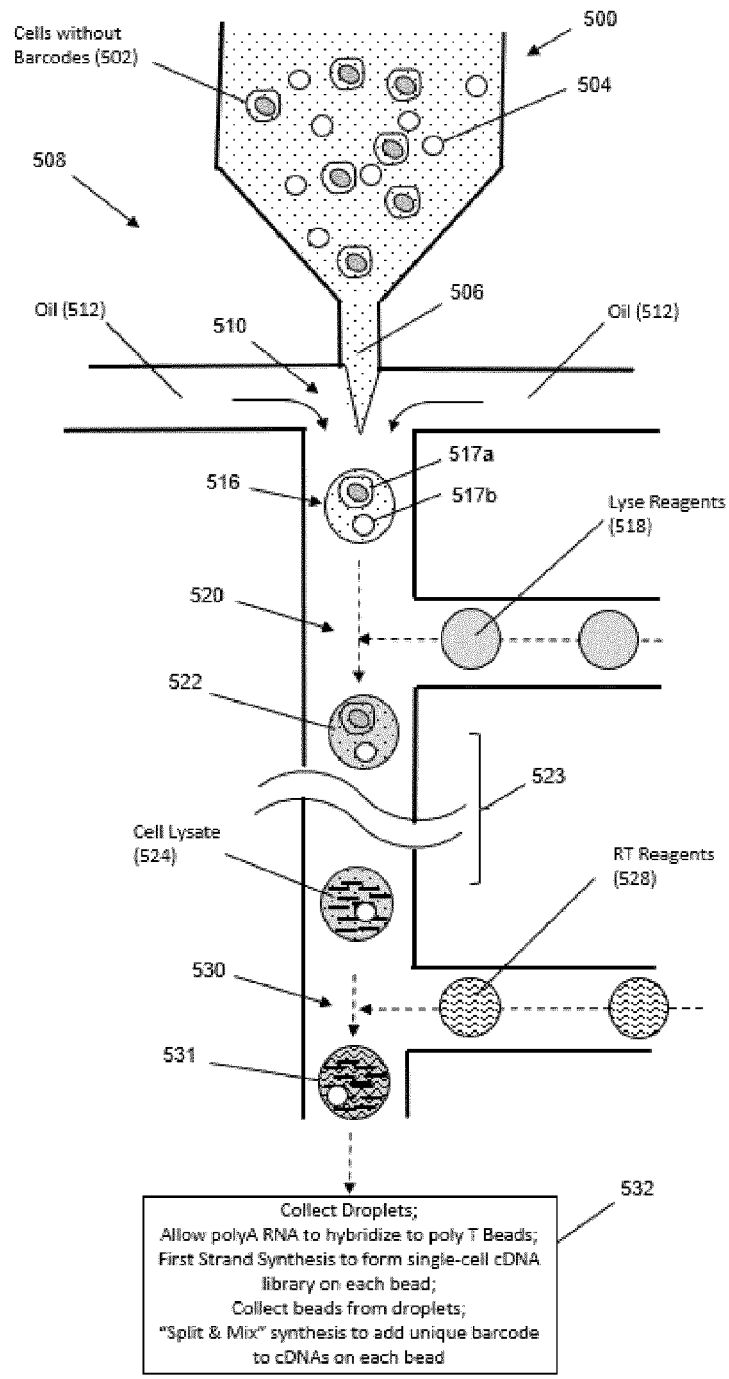
FIG. 5 illustrates an alternative method for generating barcoded single-cell cDNA libraries.

An alternative application for single-cell transcriptome analysis is illustrated in FIG. 5. In this embodiment, cells (without barcodes)(502) are mixed with polyT beads (also without barcodes)(504) and disposed in an aqueous mixture in chamber (500) of microfluidics device (508). As mentioned above, approaches not depending on microfluidics devices may also be applied, e.g. Abate et al, International patent publication WO2019/139650. The aqueous mixture is forced through passage (506) into oil stream (512) at junction (510) so that aqueous droplets form, some of which (516) contain one cell (517a) and one bead (517b). Such droplets are then coalesced with droplets (518) containing cell lysis reagents at junction (520) to form droplet (522) in which cells are lysed releasing polyA RNA, which anneals to the polyT primers attached to beads (517b). After appropriate incubation to release the desired cellular constituents, such as mRNA, the lysate-containing droplets are then coalesced at junction (530) with droplets (528) containing reverse transcriptase reagents, such as a reverse transcriptase, appropriate salts, and a buffer system that may counteract or alter conditions (e.g. high pH) imposed by the lysis reaction. Resulting droplets (531) are collected (532) and incubated so that polyA RNA anneals to polyT primers on beads (517b) and serves as a template for the reverse transcriptase extension of the polyT segments to form a single-cell cDNA library covalently attached to bead (517b). Beads (517b) may then be collected from the droplets and combined and subjected to "split and mix" synthesis to add a unique barcode and further sequences, such as primer binding sites, for subsequent manipulation, such as copying and preparation of high throughput sequencing, as described above.

Clearly many other microfluidics device configurations may be employed to generate micelles containing a single cell and a predetermined number of homogeneous sequence tags, for example, one homogeneous sequence tag, two homogeneous sequence tags, or to selectively add reagents to a micelle by selectively coalescing micelles, by electroporation, or the like, e.g. Zagoni et al, chapter 2, Methods of Cell Biology, 102: 25-48 (2011); Brouzes, chapter 10, Methods of Cell Biology, 102: 105-139 (2011); Wiklund et al, chapter 14, Methods of Cell Biology, 102: 177-196 (2011); Le Gac et al, chapter 7, Methods of Molecular Biology, 853: 65-82 (2012); and the like.

Fixing and Permeabilizing Cells or Tissues

In some embodiments, initiators coupled to binding compounds comprising nucleic acid hybridization probes and/or protein-specific binding compounds may be directed to intracellular targets, such as intracellular proteins, messenger RNAs, and/or genomic DNAs. In some embodiments, cells are fixed and permeablilized for application of binding compounds specific for such intracellular targets. Fixing and permeablization of cells may be carried out by conventional protocols, such as used in flow cytometry. Typically such protocols include a steps of treating cells with a fixing agent followed by a step of treating cells with a permeabilizing agent. A fixing step typically immobilizes intracellular cellular targets, while retaining cellular and subcellular architecture and permitting unhindered access of antibodies and/ or hybridization probes to all cells and subcellular compartments. Wide ranges of fixatives are commercially available, and the correct choice of method will depend on the nature of the targets being examined and on the properties of the antibody and/or hybridization probes used. Fixation methods fall generally into two classes: organic solvents and cross-linking reagents. Organic solvents such as alcohols and acetone remove lipids and dehydrate the cells, while precipitating the proteins on the cellular architecture. Cross-linking reagents (such as paraformaldehyde) form intermolecular bridges, normally through free amino groups, thus creating a network of linked antigens. Cross-linkers preserve cell structure better than organic solvents, but may reduce the antigenicity of some cell components, and require the addition of a permeabilization step, to allow access of the antibodies and/or hybridization probes to the intracellular targets. Exemplary fixing and permeabilizing steps include, but are not limited to, methanol-acetone fixation (fix in cooled methanol, 10 minutes at −20° C.; permeabilize with cooled acetone for 1 min at −20° C.); paraformaldehyde-triton fixation (fix in 3-4% paraformaldehyde for 10-20 min; rinse with phosphate buffered saline (PBS); permeabilize with 0.5% Triton X-100 for 2-10 min); paraformaldehyde-methanol fixation (fix in 3-4% paraformaldehyde for 10-20 min; rinse with PBS; permeabilize with cooled methanol for 5-10 min at −20° C.). Permeabilizing agents include, but are not limited to, detergents saponin, Triton X-100, Tween-20, NP40. Permeabilizing agents may also include proteinases, such as proteinase K, streptolysin 0, and the like.

Figure 6:
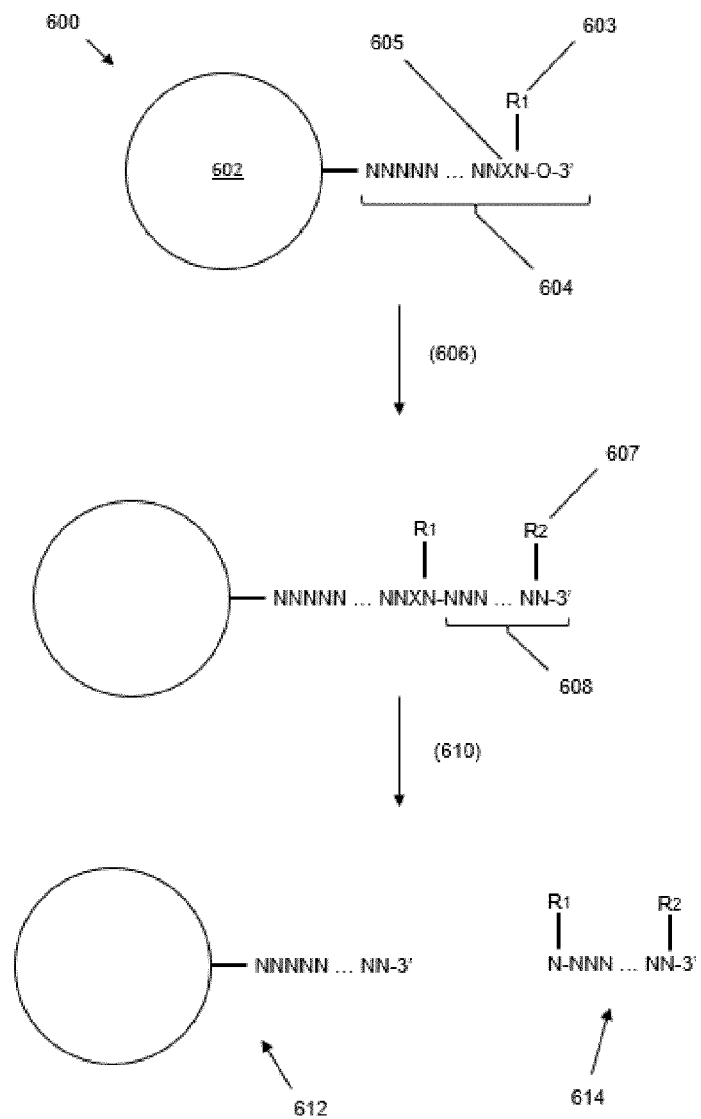
FIG. 6 illustrates a chimeric enzymatically/chemically synthesized probe.

Chimeric Enzymatically and Chemically Synthesized Polynucleotides For User Specified Applications Frequently products used in medicine and biology comprise components that may be used in every circumstance and components that must be provided anew for particular applications, the latter components sometimes being referred to as "user specified" or "user determined" components. Many nucleic acid reagents are of this character. In particular, common components of labeled hybridization probes may be manufactured in bulk and provided as kits for a user who, to obtain an operable assay, must supply a specific component, for example, a target specific component of a probe which hybridizes to a nucleic acid target of interest. Exemplary techniques that are provided in the above format include, but are not limited to, Taqman probes, CRISPR guide sequences, various kinds of PCR probes, and the like, which can be constructed as combinations of pre-existing chemically synthesized oligonucleotides and enzymatically user specified oligonucleotides using methods of the invention. FIG. 6 is a simple example of such a chimeric product comprising a taqman probe, or a precursor to a taqman probe. Product (600) comprising solid support (602) with initiator oligonucleotide (604) attached by its 5' end may be centrally mass produced using organic chemical techniques, as the components are employed in every specific probe design. In this embodiment, initiator oligonucleotide includes cleavable nucleotide "X" (605) and nucleotide distal to "X" including moiety, "$R_1$," (603), which may be a label, such as a fluorescent donor or quencher, or a reactive group, such as a member of a click chemistry pair, which may be used to attach a donor or acceptor label. In some embodiments, $R_1$ is attached to a base, e.g. an exocyclic amine. Product (600) may be a component of a kit for a user to produce a taqman probe specific for a target of special interest to him. To the 3' end of the initiator oligonucleotide of product (600), a user may synthesize a sequence-specific extension (608) that may include a nucleotide with moiety "$R_2$" (607) which may be a complementary donor or quencher which operates with $R_1$, or $R_2$ may be a reactive group, such as a member of a click chemistry pair orthogonal to that of $R_1$ which permits facile attachment of such a label. After the synthesis is completed, the extended oligonucleotide may be cleaved (610) from support (602) to give taqman probe (614) and used support (612) that may be discarded.

A similar kit may be prepared for providing single guide RNAs (sgRNAs): i) a bead with an initiator sequence attached wherein a T7 promoter is included; ii) customer buys kit with bead, synthesizes its favorite target specific sequence +20-25 nt of the 5' scaffold domain on the end of the initiator; iii) Upon synthesis completion, (a) Anneal complementary 3' scaffold domain onto the oligonucleotide still attached to the beads, (b) Allow primer extension to generate a dsDNA, and (c) Allow reverse transcription to generate sgRNA molecules.

Kits

The invention includes kits for carrying out methods of the invention. In some embodiments, "kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

In some embodiments, a kit of the invention includes a template-free polymerase. In some embodiments, a template-free polymerase is a terminal deoxynucleotidyl transferase (TdT) or a variant thereof. In some such kits, a template-free polymerase includes 3'-O-blocked nucleotides. In further embodiments in kits for extending polynucleotides or cDNAs, a kit may include a solid support with an initiator.

In some embodiments, a kit of the invention for synthesizing a random oligonucleotide barcode includes, a TdT or a variant thereof, 3'-O-blocked nucleoside triphosphates, arrays of microwells for carrying out extension and de-blocking reactions for split and mix synthesis of a barcode.

In some embodiments, a kit may include a microfluidic device for processing single cells and for delivering reagents thereto.

In some embodiments, a kit may include one or more solid supports with oligonucleotides attached for carry out methods of synthesizing unique oligonucleotide barcodes on cDNAs. In some embodiments, such one or more solid supports comprise beads; in other embodiments, such one or more solid supports comprise a planar support having a surface coated with capture oligonucleotides.

Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999).

"Amplify," "amplifies," "amplified," "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation. "Amplicon" means the product of a polynucleotide amplification reaction; that is, a clonal population of polynucleotides, which may be single stranded or double stranded, which are replicated from one or more starting sequences. "Amplifying" means producing an amplicon by carrying out an amplification reaction. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799

(rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Binding compound" means, in some embodiments, any molecule to which oligonucleotide tags can be attached for identification that is capable of specifically binding to a non-nucleic acid ligand. Binding compounds include, but are not limited to, antibodies or compounds derived from antibodies, e.g. Fab fragments. Non-nucleic acid ligands include, but are not limited to, proteins. In some embodiments, binding compounds are attached, e.g. covalently attached, to a surface of a solid support. In some embodiments, oligonucleotide tags are releasably attached to binding compounds; that is, they are attached by a linkage that includes a bond that may be selectively cleaved by predetermined conditions, e.g. light, high pH, low pH, specific redox conditions, specific electrical potential, or the like.

"Functionally equivalent" in reference to amino acid positions in two or more different TdTs means (i) the amino acids at the respective positions play the same functional role in an activity of the TdTs, and (ii) the amino acids occur at homologous amino acid positions in the amino acid sequences of the respective TdTs. It is possible to identify positionally equivalent or homologous amino acid residues in the amino acid sequences of two or more different TdTs on the basis of sequence alignment and/or molecular modelling. In some embodiments, functionally equivalent amino acid positions belong to sequence motifs that are conserved among the amino acid sequences of TdTs of evolutionarily related species, e.g. genus, families, or the like. Examples of such conserved sequence motifs are described in Motea et al, Biochim. Biophys. Acta. 1804(5): 1151-1166 (2010); Delarue et al, EMBO J., 21: 427-439 (2002); and like references.

"Microfluidics" device or "nanofluidics" device, used interchangeably herein, each means an integrated system for capturing, moving, mixing, dispensing or analyzing small volumes of fluid, including samples (which, in turn, may contain or comprise cellular or molecular analytes of interest), reagents, dilutants, buffers, or the like. Generally, reference to "microfluidics" and "nanofluidics" denotes different scales in the size of devices and volumes of fluids handled. In some embodiments, features of a microfluidic device have cross-sectional dimensions of less than a few hundred square micrometers and have passages, or channels, with capillary dimensions, e.g. having maximal cross-sectional dimensions of from about 500 μm to about 0.1 μm. In some embodiments, microfluidics devices have volume capacities in the range of from 1 μL to a few nL, e.g. 10-100 nL. Dimensions of corresponding features, or structures, in nanofluidics devices are typically from 1 to 3 orders of magnitude less than those for microfluidics devices. One skilled in the art would know from the circumstances of a particular application which dimensionality would be pertinent. In some embodiments, microfluidic or nanofluidic devices have one or more chambers, ports, and channels that are interconnected and in fluid communication and that are designed for carrying out one or more analytical reactions or processes, either alone or in cooperation with an appliance or instrument that provides support functions, such as sample introduction, fluid and/or reagent driving means, such as positive or negative pressure, acoustical energy, or the like, temperature control, detection systems, data collection and/or integration systems, and the like. In some embodiments, microfluidics and nanofluidics devices may further include valves, pumps, filters and specialized functional coatings on interior walls, e.g. to prevent adsorption of sample components or reactants, facilitate reagent movement by electroosmosis, or the like. Such devices may be fabricated as an integrated device in a solid substrate, which may be glass, plastic, or other solid polymeric materials, and may have a planar format for ease of detecting and monitoring sample and reagent movement, especially via optical or electrochemical methods. In some embodiments, such devices are disposable after a single use. In some embodiments, microfluidic and nanofluidic devices include devices that form and control the movement, mixing, dispensing and analysis of droplets, such as, aqueous droplets immersed in an immiscible fluid, such as a light oil. The fabrication and operation of microfluidics and nanofluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437; Cao, "Nanostructures & Nanomaterials: Synthesis, Properties & Applications," (Imperial College Press, London, 2004); Haeberle et al, LabChip, 7: 1094-1110 (2007); Cheng et al, Biochip Technology (CRC Press, 2001); and the like.

"Mutant" or "variant," which are used interchangeably, refer to polypeptides derived from a natural or reference TdT polypeptide described herein, and comprising a modification or an alteration, i.e., a substitution, insertion, and/or deletion, at one or more positions. Variants may be obtained by various techniques well known in the art. In particular, examples of techniques for altering the DNA sequence encoding the wild-type protein, include, but are not limited to, site-directed mutagenesis, random mutagenesis, sequence shuffling and synthetic oligonucleotide construction. Mutagenesis activities consist in deleting, inserting or substituting one or several amino-acids in the sequence of a protein or in the case of the invention of a polymerase. The following terminology is used to designate a substitution: L238A denotes that amino acid residue (Leucine, L) at position 238 of a reference, or wild type, sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

"Polymerase chain reaction" or "PCR" means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. Reaction volumes typically range from a few hundred nanoliters, e.g. 200 nL, to a few hundred µL, e.g. 200 µL.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

"Polynucleotide" and "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing. Such monomers and their internucleosidic linkages may be naturally occurring or may be analogs thereof, e.g. naturally occurring or non-naturally occurring analogs. Non-naturally occurring analogs may include phosphorothioate internucleosidic linkages, locked nucleic acids, bases containing linking groups permitting the attachment of labels, such as fluorophores, or haptens, or other oligonucleotides, and the like. Whenever the use of an oligonucleotide or polynucleotide requires enzymatic processing, such as extension by a polymerase, ligation by a ligase, or the like, one of ordinary skill in the art would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. Those skilled in the art would recognize when an enzyme has specific oligonucleotide or polynucleotide substrate requirements for activity, e.g. single stranded DNA, RNA/DNA duplex, or the like, and would be capable of selecting the appropriate compositions, especially with guidance from treatises, such as Sambrook et al, Molecular Cloning, Second Edition (Cold Spring Harbor Laboratory, New York, 1989), and like references. As used herein, "native polynucleotide" means a polymer of ribonucleotides or deoxyribonucleotides, without non-natural phosphate linkages, sugars, or bases. In some embodiments, native polynucleotides excludes polynucleotides having protection groups (such as exocyclic amine protection groups), linkers (including groups for attaching labels to bases), or labels, capture moieties, or the like. In some embodiments, a native polynucleotide may be a polynucleotide extracted from nature, a chemically or enzymatically synthesized polynucleotide without protection groups, or either of the foregoing attached to a support or with a label, linker or reactive moiety attached.

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as blast.ncbi.nlm.nih.gov/or www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

"Sequence tag" (or "tag") or "barcode" means an oligonucleotide that is attached to a polynucleotide or template molecule and is used to identify and/or track the polynucleotide or template in a reaction or a series of reactions. A sequence tag may be attached to the 3'- or 5'-end of a polynucleotide or template or it may be inserted into the interior of such polynucleotide or template to form a linear conjugate, sometime referred to herein as a "tagged polynucleotide," or "tagged template," or "tag-polynucleotide conjugate," "tag-molecule conjugate," or the like. Sequence tags may vary widely in size and compositions; the following references, which are incorporated herein by reference, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g. via a hybridization reaction or via an enzymatic reaction, such as sequencing; whether they are labeled, e.g. with a fluorescent dye or the like; the number of distinguishable oligonucleotide tags required to unambiguously identify a set of polynucleotides, and the like, and how different must tags of a set be in order to ensure reliable identification, e.g. freedom from cross hybridization or misidentification from sequencing errors. In one aspect, sequence tags can each have a length within a range of from 2 to 36 nucleotides, or from 4 to 30 nucleotides, or from 8 to 20 nucleotides, or from 6 to 10 nucleotides, respectively. In one aspect, sets of sequence tags are used wherein each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions. The amino acids are herein represented by their one-letter or three-letters code according to the following nomenclature: A: alanine (Ala); C: cysteine (Cys); D: aspartic acid (Asp); E. glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Tip) and Y: tyrosine (Tyr). In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

"Transcriptome" means a collection of all (or nearly all) gene transcripts produced in a particular cell, collection of cells, sample or tissue type. In some embodiments, a transcriptiome comprises all or nearly all of the polyA messenger RNA (mRNA) of a cell, collection of cells, sample or tissue type.

"Viable" in reference to cells, tissues or organisms, in some embodiments, means that the cells, tissues or organisms are capable of being grown, cultured, or further propagated. In some embodiments, viable cells are alive and capable of mitotic or meiotic division and further growth after being subjected to at least one cycle of template-free enzymatic elongation of an attached initiator oligonucleotide. The term "viable cell" may include viable eurkaryotic cells, prokaryotic cells, or viruses. In some embodiments, "viable cell" means viable eurkaryotic cell; and in other embodiments, "viable cell" means viable mammalian cell. "Viable conditions" as the term is used herein are physiochemical reaction conditions (e.g. temperature, salt concentration, solvent, and the like) that have no substantial deleterious effect on cell viability. In some embodiments, it is understood that additional reaction mixture components would be required for particular cell types, e.g. vitamins, amino acids, or the like, for viability; that is, as used herein, 'viable conditions" refers to necessary conditions for cell viability but not sufficient conditions for viability of every cell type. In some embodiments, viable conditions comprise an aqueous reaction mixture with physiological salts, especially, sodium, calcium and/or potassium, at a concentration in the range of 0.8 to 1.0 percent (w/v), pH in the range of 6.8-7.8, and temperature in the range of 15°–41° C.

The invention claimed is:

1. A method of generating cDNA libraries each having an oligonucleotide label, the method comprising the steps of:
   (a) capturing an mRNA by hybridizing the mRNA to capture oligonucleotides attached to one or more solid supports, wherein
      the capture oligonucleotides are complementary to segments of the mRNA, and the capture oligonucleotides are attached to the one or more solid supports by 5'-ends and have 3'-ends with free 3'-O-hydroxyls;
   (b) extending the 3'-ends of the capture oligonucleotides with a reverse transcriptase using the captured mRNAs as templates to form the cDNA libraries on the one or more solid supports; and
   (c) synthesizing oligonucleotide labels on cDNAs of the one or more solid supports by template-free enzymatic synthesis;
   wherein:
      said step (a) of capturing includes capturing the mRNA of a single cell or single tissue on the one or more solid supports to form said cDNA libraries that are cell-specific or tissue-specific cDNA libraries, respectively;
      said oligonucleotide labels are unique cell-specific or tissue-specific oligonucleotide barcodes; and
      said one or more solid supports include binding compounds attached thereto for capturing predetermined non-nucleic acid ligands.

2. The method of claim 1, wherein said step of synthesizing comprises synthesizing said unique cell-specific oligonucleotide barcodes by a split and mix synthesis method.

3. The method of claim 1, wherein said binding compounds comprise one or more species of antibody each with a predetermined specificity for one of said predetermined non-nucleic acid ligands, each different species of antibody having attached a releasable oligonucleotide barcode from which the antibody can be identified.

4. The method of claim 3 wherein the method is used for uniquely barcoding cells, either living cells, fixed cells, or fixed and permeabilized cells.

5. The method of claim 3 wherein protein expression may be monitored using one or more protein-specific antibodies each linked to a distinct initiator that may be extended by enzymatic synthesis.

6. The method of claim 3 wherein mRNA expression may be monitored using mRNA-specific primers to generate cDNAs that may be extended.

7. The method of claim 3, the method comprising:
   (a) disposing on a tissue section under binding conditions a plurality of different types of antibodies, each different type of antibody being capable of specifically binding to a different one of a plurality of proteins, each different type of antibody having a releasably attached antibody barcode, each antibody barcode comprising an initiator with a free 3'-hydroxyl;
   (b) repeating for a plurality of cycles at predetermined positions on the tissue section the steps of:
      (i) contacting the antibody barcodes having free 3'-O-hydroxyls with a 3'-O-blocked nucleoside triphosphate and a template-independent DNA polymerase so that the antibody barcodes are elongated by incorporation of a 3'-O-blocked nucleoside triphosphate to form 3'-O-blocked elongated fragments, and (ii) enzymatically deblocking the elongated fragments to form elongated fragments having free 3'-hydroxyls, thereby synthesizing a different position tag onto the releasably attached antibody barcodes at each different position to form position tag-antibody barcode conjugates;

(c) releasing the position tag-antibody barcode conjugates; and (d) sequencing the released position tag-antibody barcode conjugates to determine a spatial distribution of the plurality of proteins in the tissue section.

\* \* \* \* \*